(12) United States Patent
Tanaka et al.

(10) Patent No.: US 10,336,810 B2
(45) Date of Patent: Jul. 2, 2019

(54) CHIMERIC ANTIGEN RECEPTORS, ENCODING NUCLEIC ACIDS AND METHODS OF USE THEREOF

(71) Applicants: University Health Network, Toronto (CA); Takara Bio Inc., Shiga (JP)

(72) Inventors: Shinya Tanaka, Shiga (JP); Naoto Hirano, Toronto (CA); Yuki Kagoya, Toronto (CA)

(73) Assignees: University Health Network, Toronto (CA); Takara Bio Inc., Shiga (JP)

(*) Notice: Subject to any disclaimer, the term of this patent is extended or adjusted under 35 U.S.C. 154(b) by 0 days.

(21) Appl. No.: 15/550,645

(22) PCT Filed: Feb. 11, 2016

(86) PCT No.: PCT/CA2016/050126
§ 371 (c)(1),
(2) Date: Aug. 11, 2017

(87) PCT Pub. No.: WO2016/127257
PCT Pub. Date: Aug. 18, 2016

(65) Prior Publication Data
US 2018/0037630 A1 Feb. 8, 2018

Related U.S. Application Data

(60) Provisional application No. 62/115,527, filed on Feb. 12, 2015.

(51) Int. Cl.
| | | |
|---|---|---|
| *A61K 35/00* | (2006.01) | |
| *A61K 38/00* | (2006.01) | |
| *C07K 16/28* | (2006.01) | |
| *C12N 15/62* | (2006.01) | |
| *C07K 14/705* | (2006.01) | |
| *C07K 14/715* | (2006.01) | |
| *C07K 14/725* | (2006.01) | |

(52) U.S. Cl.
CPC ...... *C07K 14/7155* (2013.01); *C07K 14/7051* (2013.01); *C07K 14/70517* (2013.01); *C07K 14/70521* (2013.01); *C07K 16/2803* (2013.01); *C12N 15/62* (2013.01); *A61K 35/00* (2013.01); *A61K 38/00* (2013.01); *C07K 2317/622* (2013.01); *C07K 2319/00* (2013.01); *C07K 2319/03* (2013.01)

(58) Field of Classification Search
CPC ......... C07K 14/70517; C07K 14/7051; C07K 14/70521; C07K 14/7155; C07K 16/2803; C07K 2317/622; C07K 2319/00; C07K 2319/03; C12N 15/62; A61K 38/00; A61K 35/00
See application file for complete search history.

(56) References Cited

U.S. PATENT DOCUMENTS

| | | |
|---|---|---|
| 4,694,778 A | 9/1987 | Learn et al. |
| 8,119,772 B2 | 2/2012 | Yang et al. |
| 2009/0226404 A1 | 9/2009 | Schuler et al. |
| 2013/0266551 A1 | 10/2013 | Campana et al. |

FOREIGN PATENT DOCUMENTS

| | | |
|---|---|---|
| WO | 1996/023881 A1 | 8/1996 |
| WO | 2010/089412 A1 | 8/2010 |
| WO | 2012/154858 A1 | 11/2012 |
| WO | 2014/100385 A1 | 6/2014 |
| WO | 2014/190273 A1 | 11/2014 |

OTHER PUBLICATIONS

Friedrich K, et al. (Aug. 1, 1999). International Immunology. 11(8):1283-1293. https://doi.org/10.1093/intimm/11.8.1283.*
Kiu H and Nicholson SE. (Apr. 2012). Growth Factors. 30(2): 88-106. doi:10.3109/08977194.2012.660936.*
O'Brien KB, et al. (Apr. 4, 2003). Journal of Biological Chemistry. 278(14):11970-11978. DOI 10.1074/jbc.M210765200.*
Kowolik, C.M. et al. "CD28 Costimulation Provided through a CD19-Specific Chimeric Antigen Receptor Enhances In Vivo Persistence and Antitumor Efficacy of Adoptively Transferred T Cells", Cancer Research, vol. 66, No. 22, Nov. 15, 2006 (Nov. 15, 2006), pp. 10995-11004 (abstract; p. 10996, col. 1).
Kagoya, Yuki et al. "A novel chimeric antigen receptor containing a JAK-STAT signaling domain mediates superior antitumor effects", Nature Medicine, vol. 24, No. 3, Feb. 5, 2018 (Feb. 5, 2018), pp. 352-359.
Abe, Koji, et al., "The YXXQ motif in gp 130 is crucial for STAT3 phosphotylation at Ser727 through an H7-sensitive kinase pathway." Oncogene, 2001, vol. 20, pp. 3464-3474.
Fujii, Hodaka, et al., "Activation of Stat5 by interleukin 2 requires a carboxyl-terminal region of the interleukin 2 receptor beta chain but is not essential for the proliferative signal transmission." Proceedings of the National Academy of Sciences USA, Jun. 1995, vol. 92, pp. 5482-5486.
Mahmud, Shawn A., et al., "Interleukin-2 and STAT5 in regulatory T cell development and function." JAK-STAT, Jan. 1, 2013, vol. 2, No. 1, pp. e23154-1 to e23154-6, www.landesbioscience.com.
Johnson, Laura, et al., "Gene transfer of tumor-reactive TCR Confers Both High Avidity and Tumor Reactivity to Nonreactive Peripheral Blood Mononuclear Cells and Tumor-Infiltrating Lymphocytes." The Journal of Immunology, Nov. 2006, vol. 177, No. 9, pp. 6548-6559.
Nakatsugawa, Munehide, et al., "Specific Roles of Each TCR Hemichain in Generating Functional Chain-Centric TCR." The Journal of Immunology, 2015, vol. 194, pp. 3487-3500.

(Continued)

*Primary Examiner* — Robert S Landsman
(74) *Attorney, Agent, or Firm* — Fitch, Even, Tabin & Flannery LLP

(57) ABSTRACT

Disclosed herein are chimeric antigen receptors (CARs) comprising an intracellular segment comprising an interleukin receptor chain, a JAK-binding motif, a Signal Transducer and Activator of Transcription (STAT) 5 association motif and/or a CD3ζ intracellular signaling domain comprising an exogenous STAT3 association motif, as well as cells and 5 compositions comprising said CARs and uses thereof.

14 Claims, 22 Drawing Sheets

Specification includes a Sequence Listing.

(56) References Cited

OTHER PUBLICATIONS

Ochi, Toshiki, et al., "Molecular Separation of Antigen Reactivity and Allogeneic Reactivity in Human T Cells." Immune Therapy Program, 2014, Abstract, 1 page.

Kisseleva, T. et al., "Signaling through the JAK/STAT pathway, recent advances and future challenges." Gene, 2002, vol. 285, pp. 1-24.

Themeli, Maria et al., "Generation of tumor-targeted human T lymphocytes from induced pluripotent stem cells for cancer therapy." Nature Biotechnology, Oct. 2013, vol. 31, No. 10, pp. 928-935.

Finney, Helene M. et al., "Activation of Resting Human Primary T Cells with Chimeric Receptors: Costimulation from CD28, Inducible Costimulator, CD134, and CD137 in Series with Signals from the TCR Chain." The Journal of Immunology, 2004, vol. 172, pp. 104-113.

Markley John C. et al., "IL-7 and IL-21 are superior to IL-2 and IL-15 in promoting human T cell-mediated rejection of systemic lymphoma in immunodeficient mice." Blood, Apr. 29, 2010, vol. 115, No. 17, pp. 3508-3519.

Zeng, Rong, et al., "Synergy of IL-21 and IL-15 in regulating CD8+ T cell expansion and function." The Journal of Experimental Medicine, Jan. 3, 2005, vol. 201, No. 1, pp. 139-148.

Sadelain, Michel, et al., "The promise and potential pitfalls of chimeric antigen receptors." Current Opinion in Immunology, 2009, vol. 21, pp. 215-223.

Cui, Weiguo, et al., "An Interleukin-21-Interleukin-10-STAT3 Pathway is Critical for Functional Maturation of Memory CD8+ T Cells." Immunity, Nov. 23, 2011, vol. 35, pp. 792-805.

Siegel, Andrea, et al., "A Critical Role for STAT3 Transcription Factor Signaling in the Development and Maintenance of Human T Cell Memory." Immunity, Nov. 23, 2011, vol. 35, pp. 806-818.

Kochenderfer, James N., et al., "Construction and Preclinical Evaluation of an Anti-CD19 Chimeric Antigen Receptor." Journal of Immunotherapy, Sep. 2009, vol. 32, No. 7, pp. 689-702.

Nicholson, Ian, C., et al., "Construction and Characterisation of a Functional CD19 Specific Single Chain Fv Fragment for Immunotherapy of B Lineage Leukaemia and Lymphoma." Molecular Immunology, 1997, vol. 34, pp. 1157-1165.

Butler, Marcus O., et al., "Ex Vivo Expansion of Human CD8+ T Cells Using Autologous CD4+ T Cell Help." PLoS One, Jan. 2012, vol. 7, No. 1, pp. 1-11.

Milone, Michael, et al., "Chimeric Receptors Containing CD137 Signal Transduction Domains Mediate Enhanced Survival of T Cells and Increased Antileukemic Efficacy In Vivo." Molecular Therapy, Aug. 2009, vol. 17, No. 8, pp. 1453-1464.

Love, Paul E., et al., "ITAM-mediated Signaling by the T-Cell Antigen Receptor." Cold Spring Harbor Perspectives in Biology, 2010, vol. 2, pp. 1-11.

Irving, Bryan A., et al., "Functional Characterization of a Signal Transducing Motif Present in the T cell Antigen Receptor Zeta Chain." Journal of Experimental Medicine, Apr. 1993, vol. 177, No. 4, pp. 1093-1103.

Shores, Elizabeth W., et al., "Role of the Multiple T Cell Receptor (TCR)-zeta Chain Signaling Motifs in Selection of the T Cell Repertoire." Journal of Experimental Medicine, Mar. 3, 1997, vol. 185, No. 5, pp. 893-900.

Shao, Huang, et al., "Structural Requirements for Signal Transducer and Activator of Transcription 3 Binding to Phosphotyrosine Ligands Containing the YXXQ Motif." Journal of Biological Chemistry, Apr. 30, 2004, vol. 279, No. 18, pp. 18967-18973.

Friedmann, Michael C., et al., "Different interleukin 2 receptor beta-chain tyrosines couple to at least two signaling pathways and synergistically mediate interleukin 2-induced proliferation." Proceedings of the National Academy of Sciences USA, Mar. 1996, vol. 93, No. 5, pp. 2077-2082.

Klingmuller, Ursula, et al., "Multiple tyrosine residues in the cytosolic domain of the erythropoietin receptor promote activation of STAT5." Proceedings of the National Academy of Sciences USA, Aug. 1996, vol. 93, No. 16, pp. 8324-8328.

Klock, Heath E., et al., "Combining the polymerase incomplete primer extension method for cloning and mutagenesis with microscreening to accelerate structural genomics efforts." Proteins, 2008, vol. 71, pp. 982-994.

Li, Mamie Z., et al., "Harnessing homologous recombination in vitro to generate recombinant DNA via SLIC." Nature Methods, 2007, vol. 4, No. 3, pp. 251-256.

Bryskin, Anton V., et al., "Overlap extension PCR cloning: a simple and reliable way to create recombinant plasmids." BioTechniques, 2010, vol. 48, No. 6, pp. 463-465.

Unger, Tamar, et al., "Applications of the Restriction Free (RF) cloning procedure for molecular manipulations and protein expression." Journal of Structural Biology, 2010, vol. 172, pp. 34-44.

Schmitz, Jochen, et al. "The Cytoplasmic Tyrosine Motifs in Full-Length Glycoprotein 130 Have Different Roles in IL-6 Signal Transduction." The Journal of Immunology, 2000, vol. 164, pp. 848-854.

Tomida, Mikio, et al., "Cytoplasmic Domains of the Leukemia Inhibitory Factor Receptor Required for STAT3 Activation, Differentiation, and Growth Arrest of Myeloid Leukemic Cells." Blood, Mar. 15, 1999, vol. 93, pp. 1934-1941.

Ochi, Toshiki, et al., "Optimization of T-cell Reactivity by Exploiting TCR Chain Centricity for the Purpose of Safe and Effective Antitumor TCR Gene Therapy." Cancer Immunology Research, Sep. 2015, vol. 3, No. 9, pp. 1070-1081.

Nakatsugawa, Munehide, et al., "Specific Roles of Each TCR Hemichain in Generating Functional Chain-Centric TCR." The Journal of Immunology, 2015, vol. 194, No. 7, pp. 3487-3500.

International Search Report, International Patent Application No. PCT/CA2016/050126, dated May 17, 2016, 7 pages.

Written Opinion, International Patent Application No. PCT/CA2016/050126, dated May 17, 2016, 8 pages.

Anonymous, "A Next-Generation Chimeric Antigen Receptor Induces JAK-STAT Signaling", Cancer Discovery, vol. 8, No. 4, Feb. 16, 2018 (Feb. 16, 2018), p. 384.

* cited by examiner

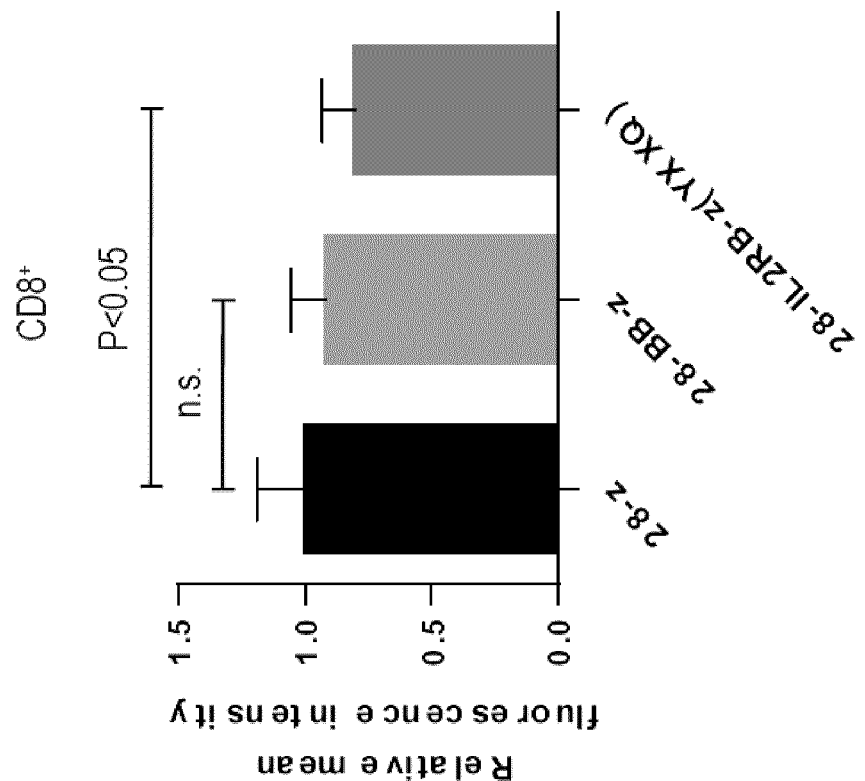
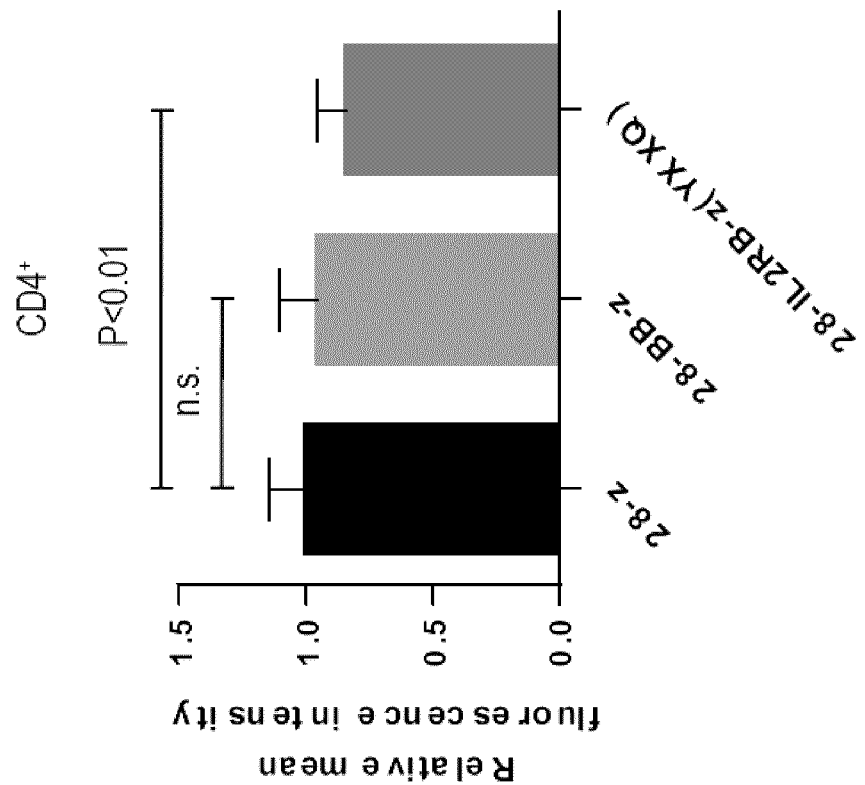
Fig. 3

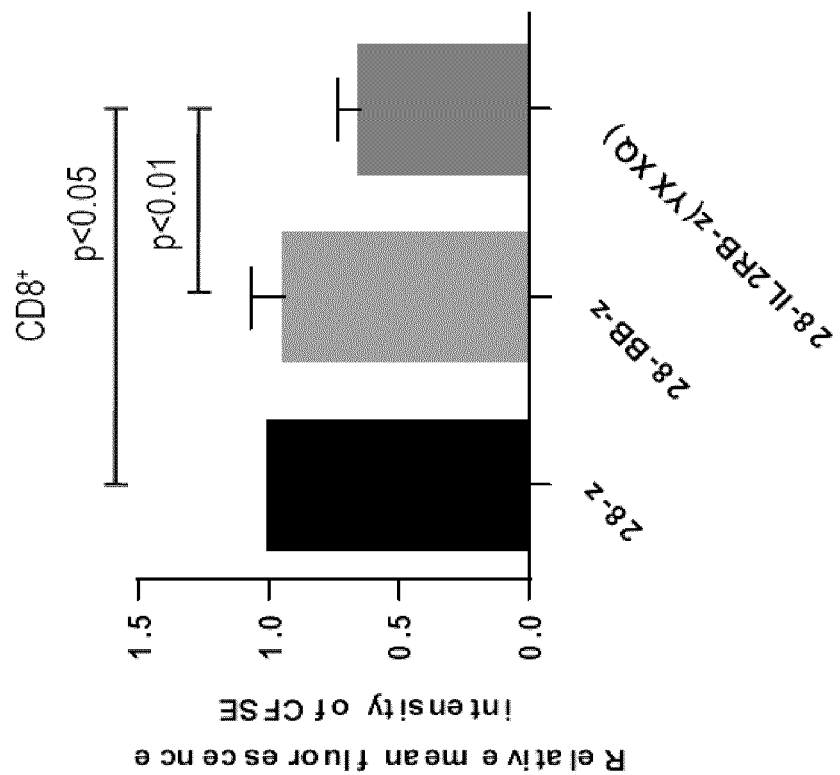
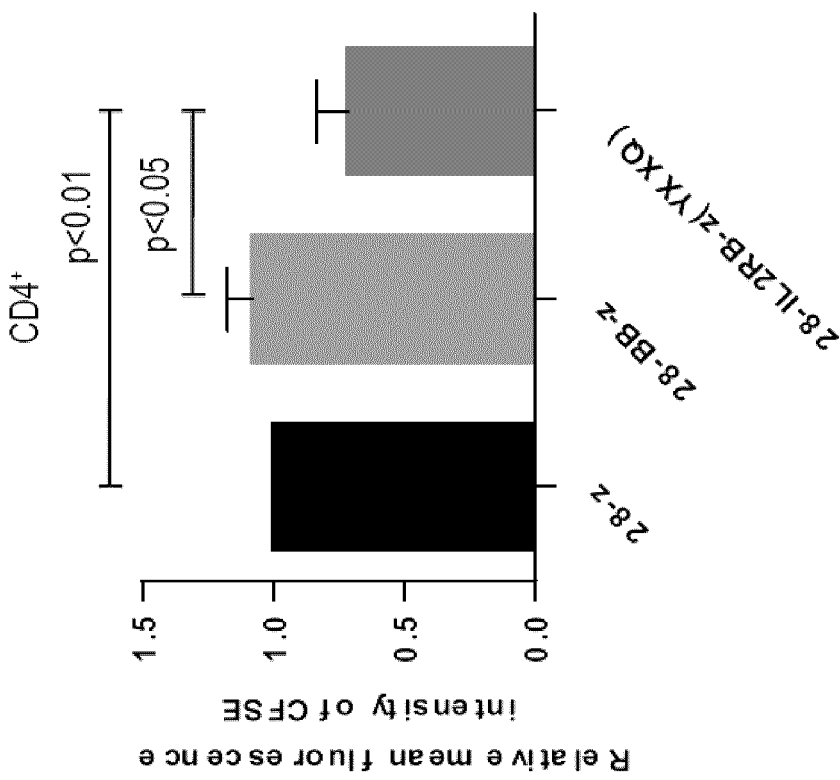
Fig. 11

SEQUENCE LISTING

<160> NUMBER OF SEQ ID NOS: 45

<210> SEQ ID NO 1

```
<211> LENGTH: 492
<212> TYPE: PRT
<213> ORGANISM: Artificial Sequence
<220> FEATURE:
<223> OTHER INFORMATION: Synthetic Construct NFMC63-28Z

<400> SEQUENCE: 1

Met Gly Val Leu Leu Thr Gln Arg Thr Leu Leu Ser Leu Val Leu Ala
1               5                   10                  15

Leu Leu Phe Pro Ser Met Ala Ser Met Asp Ile Gln Met Thr Gln Thr
            20                  25                  30

Thr Ser Ser Leu Ser Ala Ser Leu Gly Asp Arg Val Thr Ile Ser Cys
        35                  40                  45

Arg Ala Ser Gln Asp Ile Ser Lys Tyr Leu Asn Trp Tyr Gln Gln Lys
    50                  55                  60

Pro Asp Gly Thr Val Lys Leu Leu Ile Tyr His Thr Ser Arg Leu His
65                  70                  75                  80

Ser Gly Val Pro Ser Arg Phe Ser Gly Ser Gly Ser Gly Thr Asp Tyr
                85                  90                  95

Ser Leu Thr Ile Ser Asn Leu Glu Gln Glu Asp Ile Ala Thr Tyr Phe
            100                 105                 110

Cys Gln Gln Gly Asn Thr Leu Pro Tyr Thr Phe Gly Gly Gly Thr Lys
        115                 120                 125

Leu Glu Ile Thr Gly Ser Thr Ser Gly Ser Gly Lys Pro Gly Ser Gly
130                 135                 140

Glu Gly Ser Thr Lys Gly Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Ala Ala
            260                 265                 270

Ala Ile Glu Val Met Tyr Pro Pro Pro Tyr Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
    370                 375                 380
```

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 2
<211> LENGTH: 610
<212> TYPE: PRT
<213> ORGANISM: Artificial Sequence
<220> FEATURE:
<223> OTHER INFORMATION: Synthetic Construct NFMC63-28-d2RbZ

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Asp Ile Gln Met Thr Gln Thr
                20                  25                  30

Thr Ser Ser Leu Ser Ala Ser Leu Gly Asp Arg Val Thr Ile Ser Cys
            35                  40                  45

Arg Ala Ser Gln Asp Ile Ser Lys Tyr Leu Asn Trp Tyr Gln Gln Lys
        50                  55                  60

Pro Asp Gly Thr Val Lys Leu Leu Ile Tyr His Thr Ser Arg Leu His
65                  70                  75                  80

Ser Gly Val Pro Ser Arg Phe Ser Gly Ser Gly Ser Gly Thr Asp Tyr
                85                  90                  95

Ser Leu Thr Ile Ser Asn Leu Glu Gln Glu Asp Ile Ala Thr Tyr Phe
                100                 105                 110

Cys Gln Gln Gly Asn Thr Leu Pro Tyr Thr Phe Gly Gly Gly Thr Lys
            115                 120                 125

Leu Glu Ile Thr Gly Ser Thr Ser Gly Ser Gly Lys Pro Gly Ser Gly
130                 135                 140

Glu Gly Ser Thr Lys Gly Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
                180                 185                 190

Lys Gly Leu Glu Trp Leu Gly Val Ile Trp Gly Ser Glu Thr Thr Tyr
            195                 200                 205

Tyr Asn Ser Ala Leu Lys Ser Arg Leu Thr Ile Ile Lys Asp Asn Ser
        210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Tyr Gly Gly Ser Tyr Ala
                245                 250                 255

```
Met Asp Tyr Trp Gly Gln Gly Thr Ser Val Thr Val Ser Ser Ala Ala
            260                 265                 270

Ala Ile Glu Val Met Tyr Pro Pro Tyr Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Ile Asp Gly Gly
        370                 375                 380

Gly Gly Ser Gly Gly Gly Ser Gly Gly Gly Ser Asn Cys Arg
385                 390                 395                 400

Asn Thr Gly Pro Trp Leu Lys Lys Val Leu Lys Cys Asn Thr Pro Asp
            405                 410                 415

Pro Ser Lys Phe Phe Ser Gln Leu Ser Ser Glu His Gly Gly Asp Val
            420                 425                 430

Gln Lys Trp Leu Ser Ser Pro Phe Pro Ser Ser Ser Phe Ser Pro Gly
            435                 440                 445

Gly Leu Ala Pro Glu Ile Ser Pro Leu Glu Val Leu Glu Arg Asp Lys
    450                 455                 460

Val Thr Gln Leu Leu Pro Leu Asn Thr Asp Ala Tyr Leu Ser Leu Gln
465                 470                 475                 480

Glu Leu Gln Gly Gln Asp Pro Thr His Leu Val Lys Leu Gly Ser
                485                 490                 495

Gly Pro Arg Val Lys Phe Ser Arg Ser Ala Asp Ala Pro Ala Tyr Gln
            500                 505                 510

Gln Gly Gln Asn Gln Leu Tyr Asn Glu Leu Asn Leu Gly Arg Arg Glu
            515                 520                 525

Glu Tyr Asp Val Leu Asp Lys Arg Arg Gly Arg Asp Pro Glu Met Gly
        530                 535                 540

Gly Lys Pro Arg Arg Lys Asn Pro Gln Glu Gly Leu Tyr Asn Glu Leu
545                 550                 555                 560

Gln Lys Asp Lys Met Ala Glu Ala Tyr Ser Glu Ile Gly Met Lys Gly
                565                 570                 575

Glu Arg Arg Arg Gly Lys Gly His Asp Gly Leu Tyr Gln Gly Leu Ser
            580                 585                 590

Thr Ala Thr Lys Asp Thr Tyr Asp Ala Leu His Met Gln Ala Leu Pro
            595                 600                 605

Pro Arg
    610

<210> SEQ ID NO 3
<211> LENGTH: 782
<212> TYPE: PRT
<213> ORGANISM: Artificial Sequence
<220> FEATURE:
<223> OTHER INFORMATION: Synthetic Construct NFMC63-28-21RaZ

<400> SEQUENCE: 3
```

-continued

```
Met Gly Val Leu Leu Thr Gln Arg Thr Leu Leu Ser Leu Val Leu Ala
1               5                   10                  15

Leu Leu Phe Pro Ser Met Ala Ser Met Asp Ile Gln Met Thr Gln Thr
            20                  25                  30

Thr Ser Ser Leu Ser Ala Ser Leu Gly Asp Arg Val Thr Ile Ser Cys
        35                  40                  45

Arg Ala Ser Gln Asp Ile Ser Lys Tyr Leu Asn Trp Tyr Gln Gln Lys
    50                  55                  60

Pro Asp Gly Thr Val Lys Leu Leu Ile Tyr His Thr Ser Arg Leu His
65                  70                  75                  80

Ser Gly Val Pro Ser Arg Phe Ser Gly Ser Gly Ser Gly Thr Asp Tyr
                85                  90                  95

Ser Leu Thr Ile Ser Asn Leu Glu Gln Glu Asp Ile Ala Thr Tyr Phe
            100                 105                 110

Cys Gln Gln Gly Asn Thr Leu Pro Tyr Thr Phe Gly Gly Gly Thr Lys
        115                 120                 125

Leu Glu Ile Thr Gly Ser Thr Ser Gly Ser Gly Lys Pro Gly Ser Gly
    130                 135                 140

Glu Gly Ser Thr Lys Gly Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Tyr Gly Gly Ser Tyr Ala
                245                 250                 255

Met Asp Tyr Trp Gly Gln Gly Thr Ser Val Thr Val Ser Ser Ala Ala
            260                 265                 270

Ala Ile Glu Val Met Tyr Pro Pro Pro Tyr Leu Asp Asn Glu Lys Ser
        275                 280                 285

Asn Gly Thr Ile Ile His Val Lys Gly Lys His Leu Cys Pro Ser Pro
290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Lys Thr His Pro
370                 375                 380

Leu Trp Arg Leu Trp Lys Lys Ile Trp Ala Val Pro Ser Pro Glu Arg
385                 390                 395                 400

Phe Phe Met Pro Leu Tyr Lys Gly Cys Ser Gly Asp Phe Lys Lys Trp
                405                 410                 415
```

```
Val Gly Ala Pro Phe Thr Gly Ser Ser Leu Glu Leu Gly Pro Trp Ser
            420                 425                 430

Pro Glu Val Pro Ser Thr Leu Glu Val Tyr Ser Cys His Pro Pro Arg
        435                 440                 445

Ser Pro Ala Lys Arg Leu Gln Leu Thr Glu Leu Gln Glu Pro Ala Glu
    450                 455                 460

Leu Val Glu Ser Asp Gly Val Pro Lys Pro Ser Phe Trp Pro Thr Ala
465                 470                 475                 480

Gln Asn Ser Gly Gly Ser Ala Tyr Ser Glu Glu Arg Asp Arg Pro Tyr
                485                 490                 495

Gly Leu Val Ser Ile Asp Thr Val Thr Val Leu Asp Ala Glu Gly Pro
            500                 505                 510

Cys Thr Trp Pro Cys Ser Cys Glu Asp Asp Gly Tyr Pro Ala Leu Asp
        515                 520                 525

Leu Asp Ala Gly Leu Glu Pro Ser Pro Gly Leu Glu Asp Pro Leu Leu
    530                 535                 540

Asp Ala Gly Thr Thr Val Leu Ser Cys Gly Cys Val Ser Ala Gly Ser
545                 550                 555                 560

Pro Gly Leu Gly Gly Pro Leu Gly Ser Leu Leu Asp Arg Leu Lys Pro
                565                 570                 575

Pro Leu Ala Asp Gly Glu Asp Trp Ala Gly Gly Leu Pro Trp Gly Gly
            580                 585                 590

Arg Ser Pro Gly Gly Val Ser Glu Ser Glu Ala Gly Ser Pro Leu Ala
        595                 600                 605

Gly Leu Asp Met Asp Thr Phe Asp Ser Gly Phe Val Gly Ser Asp Cys
    610                 615                 620

Ser Ser Pro Val Glu Cys Asp Phe Thr Ser Pro Gly Asp Glu Gly Pro
625                 630                 635                 640

Pro Arg Ser Tyr Leu Arg Gln Trp Val Val Ile Pro Pro Pro Leu Ser
                645                 650                 655

Ser Pro Gly Pro Gln Ala Ser Lys Leu Gly Gly Ser Gly Pro Arg Val
            660                 665                 670

Lys Phe Ser Arg Ser Ala Asp Ala Pro Ala Tyr Gln Gln Gly Gln Asn
        675                 680                 685

Gln Leu Tyr Asn Glu Leu Asn Leu Gly Arg Arg Glu Glu Tyr Asp Val
    690                 695                 700

Leu Asp Lys Arg Arg Gly Arg Asp Pro Glu Met Gly Gly Lys Pro Arg
705                 710                 715                 720

Arg Lys Asn Pro Gln Glu Gly Leu Tyr Asn Glu Leu Gln Lys Asp Lys
                725                 730                 735

Met Ala Glu Ala Tyr Ser Glu Ile Gly Met Lys Gly Glu Arg Arg Arg
            740                 745                 750

Gly Lys Gly His Asp Gly Leu Tyr Gln Gly Leu Ser Thr Ala Thr Lys
        755                 760                 765

Asp Thr Tyr Asp Ala Leu His Met Gln Ala Leu Pro Pro Arg
    770                 775                 780

<210> SEQ ID NO 4
<211> LENGTH: 790
<212> TYPE: PRT
<213> ORGANISM: Artificial Sequence
<220> FEATURE:
<223> OTHER INFORMATION: Synthetic Construct NFMC63-28Z-21Ra

<400> SEQUENCE: 4
```

-continued

```
Met Gly Val Leu Leu Thr Gln Arg Thr Leu Ser Leu Val Leu Ala
1               5                   10                  15

Leu Leu Phe Pro Ser Met Ala Ser Met Asp Ile Gln Met Thr Gln Thr
            20              25                  30

Thr Ser Ser Leu Ser Ala Ser Leu Gly Asp Arg Val Thr Ile Ser Cys
        35                  40                  45

Arg Ala Ser Gln Asp Ile Ser Lys Tyr Leu Asn Trp Tyr Gln Gln Lys
50                      55                  60

Pro Asp Gly Thr Val Lys Leu Leu Ile Tyr His Thr Ser Arg Leu His
65                  70                  75                  80

Ser Gly Val Pro Ser Arg Phe Ser Gly Ser Gly Ser Gly Thr Asp Tyr
                85                  90                  95

Ser Leu Thr Ile Ser Asn Leu Glu Gln Glu Asp Ile Ala Thr Tyr Phe
            100                 105                 110

Cys Gln Gln Gly Asn Thr Leu Pro Tyr Thr Phe Gly Gly Gly Thr Lys
        115                 120                 125

Leu Glu Ile Thr Gly Ser Thr Gly Ser Gly Lys Pro Gly Ser Gly
    130                 135                 140

Glu Gly Ser Thr Lys Gly Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Ala Ala
            260                 265                 270

Ala Ile Glu Val Met Tyr Pro Pro Pro Tyr Leu Asp Asn Glu Lys Ser
    275                 280                 285

Asn Gly Thr Ile Ile His Val Lys Gly Lys His Leu Cys Pro Ser Pro
        290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
```

```
                420             425             430
Asn Pro Gln Glu Gly Leu Tyr Asn Glu Leu Gln Lys Asp Lys Met Ala
        435                 440                 445
Glu Ala Tyr Ser Glu Ile Gly Met Lys Gly Glu Arg Arg Arg Gly Lys
        450                 455                 460
Gly His Asp Gly Leu Tyr Gln Gly Leu Ser Thr Ala Thr Lys Asp Thr
465                 470                 475                 480
Tyr Asp Ala Leu His Met Gln Ala Leu Pro Pro Arg Gly Gly Gly Gly
                485                 490                 495
Ser Gly Gly Gly Ser Gly Gly Gly Ser Lys Thr His Pro Leu
                500                 505             510
Trp Arg Leu Trp Lys Lys Ile Trp Ala Val Pro Ser Pro Glu Arg Phe
        515                 520                 525
Phe Met Pro Leu Tyr Lys Gly Cys Ser Gly Asp Phe Lys Lys Trp Val
        530                 535                 540
Gly Ala Pro Phe Thr Gly Ser Ser Leu Glu Leu Gly Pro Trp Ser Pro
545                 550                 555                 560
Glu Val Pro Ser Thr Leu Glu Val Tyr Ser Cys His Pro Pro Arg Ser
                565                 570                 575
Pro Ala Lys Arg Leu Gln Leu Thr Glu Leu Gln Glu Pro Ala Glu Leu
                580                 585                 590
Val Glu Ser Asp Gly Val Pro Lys Pro Ser Phe Trp Pro Thr Ala Gln
        595                 600                 605
Asn Ser Gly Gly Ser Ala Tyr Ser Glu Glu Arg Asp Arg Pro Tyr Gly
        610                 615                 620
Leu Val Ser Ile Asp Thr Val Thr Val Leu Asp Ala Glu Gly Pro Cys
625                 630                 635                 640
Thr Trp Pro Cys Ser Cys Glu Asp Asp Gly Tyr Pro Ala Leu Asp Leu
                645                 650                 655
Asp Ala Gly Leu Glu Pro Ser Pro Gly Leu Glu Asp Pro Leu Leu Asp
                660                 665                 670
Ala Gly Thr Thr Val Leu Ser Cys Gly Cys Val Ser Ala Gly Ser Pro
                675                 680                 685
Gly Leu Gly Gly Pro Leu Gly Ser Leu Leu Asp Arg Leu Lys Pro Pro
        690                 695                 700
Leu Ala Asp Gly Glu Asp Trp Ala Gly Gly Leu Pro Trp Gly Gly Arg
705                 710                 715                 720
Ser Pro Gly Gly Val Ser Glu Ser Glu Ala Gly Ser Pro Leu Ala Gly
                725                 730                 735
Leu Asp Met Asp Thr Phe Asp Ser Gly Phe Val Gly Ser Asp Cys Ser
                740                 745                 750
Ser Pro Val Glu Cys Asp Phe Thr Ser Pro Gly Asp Glu Gly Pro Pro
        755                 760                 765
Arg Ser Tyr Leu Arg Gln Trp Val Val Ile Pro Pro Pro Leu Ser Ser
        770                 775                 780
Pro Gly Pro Gln Ala Ser
785                 790

<210> SEQ ID NO 5
<211> LENGTH: 94
<212> TYPE: PRT
<213> ORGANISM: Homo Sapiens

<400> SEQUENCE: 5
```

```
Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
            35                  40                  45

Ser Pro Gly Gly Leu Ala Pro Glu Ile Ser Pro Leu Glu Val Leu Glu
    50                  55                  60

Arg Asp Lys Val Thr Gln Leu Leu Pro Leu Asn Thr Asp Ala Tyr Leu
65                  70                  75                  80

Ser Leu Gln Glu Leu Gln Gly Gln Asp Pro Thr His Leu Val
                85                  90
```

<210> SEQ ID NO 6
<211> LENGTH: 283
<212> TYPE: PRT
<213> ORGANISM: Homo Sapiens

<400> SEQUENCE: 6

```
Lys Thr His Pro Leu Trp Arg Leu Trp Lys Lys Ile Trp Ala Val Pro
1               5                   10                  15

Ser Pro Glu Arg Phe Phe Met Pro Leu Tyr Lys Gly Cys Ser Gly Asp
            20                  25                  30

Phe Lys Lys Trp Val Gly Ala Pro Phe Thr Gly Ser Ser Leu Glu Leu
            35                  40                  45

Gly Pro Trp Ser Pro Glu Val Pro Ser Thr Leu Glu Val Tyr Ser Cys
    50                  55                  60

His Pro Pro Arg Ser Pro Ala Lys Arg Leu Gln Leu Thr Glu Leu Gln
65                  70                  75                  80

Glu Pro Ala Glu Leu Val Glu Ser Asp Gly Val Pro Lys Pro Ser Phe
                85                  90                  95

Trp Pro Thr Ala Gln Asn Ser Gly Gly Ser Ala Tyr Ser Glu Glu Arg
            100                 105                 110

Asp Arg Pro Tyr Gly Leu Val Ser Ile Asp Thr Val Thr Val Leu Asp
            115                 120                 125

Ala Glu Gly Pro Cys Thr Trp Pro Cys Ser Cys Glu Asp Asp Gly Tyr
    130                 135                 140

Pro Ala Leu Asp Leu Asp Ala Gly Leu Glu Pro Ser Pro Gly Leu Glu
145                 150                 155                 160

Asp Pro Leu Leu Asp Ala Gly Thr Thr Val Leu Ser Cys Gly Cys Val
                165                 170                 175

Ser Ala Gly Ser Pro Gly Leu Gly Gly Pro Leu Gly Ser Leu Leu Asp
            180                 185                 190

Arg Leu Lys Pro Pro Leu Ala Asp Gly Glu Asp Trp Ala Gly Gly Leu
            195                 200                 205

Pro Trp Gly Gly Arg Ser Pro Gly Gly Val Ser Glu Ser Glu Ala Gly
    210                 215                 220

Ser Pro Leu Ala Gly Leu Asp Met Asp Thr Phe Asp Ser Gly Phe Val
225                 230                 235                 240

Gly Ser Asp Cys Ser Ser Pro Val Glu Cys Asp Phe Thr Ser Pro Gly
                245                 250                 255

Asp Glu Gly Pro Pro Arg Ser Tyr Leu Arg Gln Trp Val Val Ile Pro
            260                 265                 270

Pro Pro Leu Ser Ser Pro Gly Pro Gln Ala Ser
            275                 280
```

```
<210> SEQ ID NO 7
<211> LENGTH: 112
<212> TYPE: PRT
<213> ORGANISM: Homo Sapiens

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 41
<212> TYPE: PRT
<213> ORGANISM: Homo Sapiens

<400> SEQUENCE: 8

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 9
<211> LENGTH: 27
<212> TYPE: PRT
<213> ORGANISM: Homo Sapiens

<400> SEQUENCE: 9

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 10
<211> LENGTH: 39
<212> TYPE: PRT
<213> ORGANISM: Homo Sapiens

<400> SEQUENCE: 10

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 11
<211> LENGTH: 286
<212> TYPE: PRT
<213> ORGANISM: Homo Sapiens

<400> SEQUENCE: 11

```
Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
50                  55                  60

Arg Asp Lys Val Thr Gln Leu Leu Gln Gln Asp Lys Val Pro Glu
65                  70                  75                  80

Pro Ala Ser Leu Ser Ser Asn His Ser Leu Thr Ser Cys Phe Thr Asn
                85                  90                  95

Gln Gly Tyr Phe Phe His Leu Pro Asp Ala Leu Glu Ile Glu Ala
            100                 105                 110

Cys Gln Val Tyr Phe Thr Tyr Asp Pro Tyr Ser Glu Glu Asp Pro Asp
        115                 120                 125

Glu Gly Val Ala Gly Ala Pro Thr Gly Ser Ser Pro Gln Pro Leu Gln
130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
            180                 185                 190

Ser Leu Gln Glu Arg Val Pro Arg Asp Trp Asp Pro Gln Pro Leu Gly
        195                 200                 205

Pro Pro Thr Pro Gly Val Pro Asp Leu Val Asp Phe Gln Pro Pro Pro
210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
            260                 265                 270

Ser Leu Gln Glu Leu Gln Gly Gln Asp Pro Thr His Leu Val
        275                 280                 285
```

<210> SEQ ID NO 12
<211> LENGTH: 5
<212> TYPE: PRT
<213> ORGANISM: Homo Sapiens

<400> SEQUENCE: 12

```
Tyr Leu Ser Leu Gln
1               5
```

<210> SEQ ID NO 13
<211> LENGTH: 4
<212> TYPE: PRT
<213> ORGANISM: Homo Sapiens
<220> FEATURE:
<221> NAME/KEY: misc_feature

```
<222> LOCATION: (2)..(3)
<223> OTHER INFORMATION: Xaa can be any naturally occurring amino acid

<400> SEQUENCE: 13

Tyr Xaa Xaa Gln
1

<210> SEQ ID NO 14
<211> LENGTH: 7
<212> TYPE: PRT
<213> ORGANISM: Homo Sapiens

<400> SEQUENCE: 14

Tyr Leu Pro Ser Asn Ile Asp
1               5

<210> SEQ ID NO 15
<211> LENGTH: 5
<212> TYPE: PRT
<213> ORGANISM: Homo Sapiens

<400> SEQUENCE: 15

Tyr Cys Thr Phe Pro
1               5

<210> SEQ ID NO 16
<211> LENGTH: 5
<212> TYPE: PRT
<213> ORGANISM: Homo Sapiens

<400> SEQUENCE: 16

Tyr Phe Phe Phe His
1               5

<210> SEQ ID NO 17
<211> LENGTH: 5
<212> TYPE: PRT
<213> ORGANISM: Homo Sapiens

<400> SEQUENCE: 17

Tyr Val Thr Met Ser
1               5

<210> SEQ ID NO 18
<211> LENGTH: 5
<212> TYPE: PRT
<213> ORGANISM: Homo Sapiens

<400> SEQUENCE: 18

Tyr Leu Pro Gln Glu
1               5

<210> SEQ ID NO 19
<211> LENGTH: 7
<212> TYPE: PRT
<213> ORGANISM: Artificial Sequence
<220> FEATURE:
<223> OTHER INFORMATION: Linker

<400> SEQUENCE: 19

Lys Leu Gly Gly Ser Gly Pro
1               5

<210> SEQ ID NO 20
<211> LENGTH: 5
```

-continued

```
<212> TYPE: PRT
<213> ORGANISM: Homo Sapiens

<400> SEQUENCE: 20

Tyr Lys Ala Phe Ser
1               5

<210> SEQ ID NO 21
<211> LENGTH: 5
<212> TYPE: PRT
<213> ORGANISM: Homo Sapiens

<400> SEQUENCE: 21

Tyr Lys Pro Phe Gln
1               5

<210> SEQ ID NO 22
<211> LENGTH: 4
<212> TYPE: PRT
<213> ORGANISM: Homo Sapiens

<400> SEQUENCE: 22

Tyr Arg His Gln
1

<210> SEQ ID NO 23
<211> LENGTH: 4
<212> TYPE: PRT
<213> ORGANISM: Homo Sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 23

Tyr Xaa Pro Gln
1

<210> SEQ ID NO 24
<211> LENGTH: 586
<212> TYPE: PRT
<213> ORGANISM: Artificial Sequence
<220> FEATURE:
<223> OTHER INFORMATION: Synthetic Construct 28-IL2RB-z(YXXQ)
<220> FEATURE:
<221> NAME/KEY: misc_feature
<222> LOCATION: (579)..(580)
<223> OTHER INFORMATION: Xaa can be any naturally occurring amino acid

<400> SEQUENCE: 24

Met Gly Val Leu Leu Thr Gln Arg Thr Leu Leu Ser Leu Val Leu Ala
1               5                   10                  15

Leu Leu Phe Pro Ser Met Ala Ser Met Asp Ile Gln Met Thr Gln Thr
                20                  25                  30

Thr Ser Ser Leu Ser Ala Ser Leu Gly Asp Arg Val Thr Ile Ser Cys
            35                  40                  45

Arg Ala Ser Gln Asp Ile Ser Lys Tyr Leu Asn Trp Tyr Gln Gln Lys
        50                  55                  60

Pro Asp Gly Thr Val Lys Leu Leu Ile Tyr His Thr Ser Arg Leu His
65                  70                  75                  80

Ser Gly Val Pro Ser Arg Phe Ser Gly Ser Gly Ser Gly Thr Asp Tyr
                85                  90                  95

Ser Leu Thr Ile Ser Asn Leu Glu Gln Glu Asp Ile Ala Thr Tyr Phe
                100                 105                 110
```

```
Cys Gln Gln Gly Asn Thr Leu Pro Tyr Thr Phe Gly Gly Gly Thr Lys
        115                 120                 125

Leu Glu Ile Thr Gly Ser Thr Ser Gly Ser Gly Lys Pro Gly Ser Gly
    130                 135                 140

Glu Gly Ser Thr Lys Gly Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
                180                 185                 190

Lys Gly Leu Glu Trp Leu Gly Val Ile Trp Gly Ser Glu Thr Thr Tyr
            195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Ala Ala
            260                 265                 270

Ala Ile Glu Val Met Tyr Pro Pro Pro Tyr Leu Asp Asn Glu Lys Ser
    275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
                340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Asn Cys Arg Asn
    370                 375                 380

Thr Gly Pro Trp Leu Lys Lys Val Leu Lys Cys Asn Thr Pro Asp Pro
385                 390                 395                 400

Ser Lys Phe Phe Ser Gln Leu Ser Ser Glu His Gly Gly Asp Val Gln
                405                 410                 415

Lys Trp Leu Ser Ser Pro Phe Pro Ser Ser Phe Ser Pro Gly Gly
            420                 425                 430

Leu Ala Pro Glu Ile Ser Pro Leu Glu Val Leu Glu Arg Asp Lys Val
                435                 440                 445

Thr Gln Leu Leu Pro Leu Asn Thr Asp Ala Tyr Leu Ser Leu Gln Glu
    450                 455                 460

Leu Gln Gly Gln Asp Pro Thr His Leu Val Arg Val Lys Phe Ser Arg
465                 470                 475                 480

Ser Ala Asp Ala Pro Ala Tyr Gln Gln Gly Gln Asn Gln Leu Tyr Asn
                485                 490                 495

Glu Leu Asn Leu Gly Arg Arg Glu Glu Tyr Asp Val Leu Asp Lys Arg
                500                 505                 510

Arg Gly Arg Asp Pro Glu Met Gly Gly Lys Pro Arg Arg Lys Asn Pro
            515                 520                 525
```

-continued

```
Gln Glu Gly Leu Tyr Asn Glu Leu Gln Lys Asp Lys Met Ala Glu Ala
            530                 535                 540

Tyr Ser Glu Ile Gly Met Lys Gly Glu Arg Arg Arg Gly Lys Gly His
545                 550                 555                 560

Asp Gly Leu Tyr Gln Gly Leu Ser Thr Ala Thr Lys Asp Thr Tyr Asp
                565                 570                 575

Ala Tyr Xaa Xaa Gln Ala Leu Pro Pro Arg
            580                 585

<210> SEQ ID NO 25
<211> LENGTH: 586
<212> TYPE: PRT
<213> ORGANISM: Artificial Sequence
<220> FEATURE:
<223> OTHER INFORMATION: Synthetic Construct 28-IL2RB-z(YRHQ)

<400> SEQUENCE: 25

Met Gly Val Leu Leu Thr Gln Arg Thr Leu Leu Ser Leu Val Leu Ala
1               5                   10                  15

Leu Leu Phe Pro Ser Met Ala Ser Met Asp Ile Gln Met Thr Gln Thr
            20                  25                  30

Thr Ser Ser Leu Ser Ala Ser Leu Gly Asp Arg Val Thr Ile Ser Cys
        35                  40                  45

Arg Ala Ser Gln Asp Ile Ser Lys Tyr Leu Asn Trp Tyr Gln Gln Lys
50                  55                  60

Pro Asp Gly Thr Val Lys Leu Leu Ile Tyr His Thr Ser Arg Leu His
65                  70                  75                  80

Ser Gly Val Pro Ser Arg Phe Ser Gly Ser Gly Ser Gly Thr Asp Tyr
                85                  90                  95

Ser Leu Thr Ile Ser Asn Leu Glu Gln Glu Asp Ile Ala Thr Tyr Phe
            100                 105                 110

Cys Gln Gln Gly Asn Thr Leu Pro Tyr Thr Phe Gly Gly Gly Thr Lys
        115                 120                 125

Leu Glu Ile Thr Gly Ser Thr Ser Gly Ser Gly Lys Pro Gly Ser Gly
130                 135                 140

Glu Gly Ser Thr Lys Gly Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Ala Ala
            260                 265                 270

Ala Ile Glu Val Met Tyr Pro Pro Pro Tyr Leu Asp Asn Glu Lys Ser
        275                 280                 285

Asn Gly Thr Ile Ile His Val Lys Gly Lys His Leu Cys Pro Ser Pro
290                 295                 300
```

```
Leu Phe Pro Gly Pro Ser Lys Pro Phe Trp Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Asn Cys Arg Asn
370                 375                 380

Thr Gly Pro Trp Leu Lys Lys Val Leu Lys Cys Asn Thr Pro Asp Pro
385                 390                 395                 400

Ser Lys Phe Phe Ser Gln Leu Ser Ser Glu His Gly Gly Asp Val Gln
                405                 410                 415

Lys Trp Leu Ser Ser Pro Phe Pro Ser Ser Ser Phe Ser Pro Gly Gly
            420                 425                 430

Leu Ala Pro Glu Ile Ser Pro Leu Glu Val Leu Glu Arg Asp Lys Val
        435                 440                 445

Thr Gln Leu Leu Pro Leu Asn Thr Asp Ala Tyr Leu Ser Leu Gln Glu
450                 455                 460

Leu Gln Gly Gln Asp Pro Thr His Leu Val Arg Val Lys Phe Ser Arg
465                 470                 475                 480

Ser Ala Asp Ala Pro Ala Tyr Gln Gln Gly Gln Asn Gln Leu Tyr Asn
                485                 490                 495

Glu Leu Asn Leu Gly Arg Arg Glu Glu Tyr Asp Val Leu Asp Lys Arg
            500                 505                 510

Arg Gly Arg Asp Pro Glu Met Gly Gly Lys Pro Arg Arg Lys Asn Pro
        515                 520                 525

Gln Glu Gly Leu Tyr Asn Glu Leu Gln Lys Asp Lys Met Ala Glu Ala
530                 535                 540

Tyr Ser Glu Ile Gly Met Lys Gly Glu Arg Arg Arg Gly Lys Gly His
545                 550                 555                 560

Asp Gly Leu Tyr Gln Gly Leu Ser Thr Ala Thr Lys Asp Thr Tyr Asp
                565                 570                 575

Ala Tyr Arg His Gln Ala Leu Pro Pro Arg
            580                 585

<210> SEQ ID NO 26
<211> LENGTH: 24
<212> TYPE: DNA
<213> ORGANISM: Homo Sapiens

<400> SEQUENCE: 26
acgcctatcg ccatcaggcc ctgc                                              24

<210> SEQ ID NO 27
<211> LENGTH: 26
<212> TYPE: DNA
<213> ORGANISM: Homo Sapiens

<400> SEQUENCE: 27
ctgatggcga taggcgtcgt aggtgt                                            26

<210> SEQ ID NO 28
<211> LENGTH: 4
<212> TYPE: PRT
<213> ORGANISM: Homo Sapiens
```

```
<400> SEQUENCE: 28

Tyr Phe Phe Phe
1

<210> SEQ ID NO 29
<211> LENGTH: 4
<212> TYPE: PRT
<213> ORGANISM: Homo Sapiens

<400> SEQUENCE: 29

Tyr Cys Thr Phe
1

<210> SEQ ID NO 30
<211> LENGTH: 4
<212> TYPE: PRT
<213> ORGANISM: Homo Sapiens

<400> SEQUENCE: 30

Tyr Leu Arg Gln
1

<210> SEQ ID NO 31
<211> LENGTH: 4
<212> TYPE: PRT
<213> ORGANISM: Homo Sapiens

<400> SEQUENCE: 31

Tyr Phe Lys Gln
1

<210> SEQ ID NO 32
<211> LENGTH: 4
<212> TYPE: PRT
<213> ORGANISM: Homo Sapiens

<400> SEQUENCE: 32

Tyr Leu Pro Gln
1

<210> SEQ ID NO 33
<211> LENGTH: 4
<212> TYPE: PRT
<213> ORGANISM: Homo Sapiens

<400> SEQUENCE: 33

Tyr Met Pro Gln
1

<210> SEQ ID NO 34
<211> LENGTH: 4
<212> TYPE: PRT
<213> ORGANISM: Homo Sapiens

<400> SEQUENCE: 34

Tyr Val Leu Gln
1

<210> SEQ ID NO 35
<211> LENGTH: 4
<212> TYPE: PRT
<213> ORGANISM: Homo Sapiens

<400> SEQUENCE: 35
```

Tyr Gln Pro Gln
1

<210> SEQ ID NO 36
<211> LENGTH: 4
<212> TYPE: PRT
<213> ORGANISM: Homo Sapiens

<400> SEQUENCE: 36

Tyr Lys Pro Gln
1

<210> SEQ ID NO 37
<211> LENGTH: 4
<212> TYPE: PRT
<213> ORGANISM: Homo Sapiens

<400> SEQUENCE: 37

Tyr Arg Pro Gln
1

<210> SEQ ID NO 38
<211> LENGTH: 4
<212> TYPE: PRT
<213> ORGANISM: Homo Sapiens

<400> SEQUENCE: 38

Tyr Thr His Gln
1

<210> SEQ ID NO 39
<211> LENGTH: 4
<212> TYPE: PRT
<213> ORGANISM: Homo Sapiens

<400> SEQUENCE: 39

Tyr Leu Lys Gln
1

<210> SEQ ID NO 40
<211> LENGTH: 4
<212> TYPE: PRT
<213> ORGANISM: Homo Sapiens

<400> SEQUENCE: 40

Tyr His Asn Gln
1

<210> SEQ ID NO 41
<211> LENGTH: 4
<212> TYPE: PRT
<213> ORGANISM: Homo Sapiens
<220> FEATURE:
<221> NAME/KEY: misc_feature
<222> LOCATION: (2)..(3)
<223> OTHER INFORMATION: Xaa can be any naturally occurring amino acid

<400> SEQUENCE: 41

Tyr Xaa Xaa Leu
1

<210> SEQ ID NO 42
<211> LENGTH: 17
<212> TYPE: PRT
<213> ORGANISM: Artificial Sequence

```
<220> FEATURE:
<223> OTHER INFORMATION: Linker

<400> SEQUENCE: 42

Ile Asp Gly Gly Gly Gly Ser Gly Gly Gly Gly Ser Gly Gly Gly
1               5                   10                  15

Ser

<210> SEQ ID NO 43
<211> LENGTH: 4
<212> TYPE: PRT
<213> ORGANISM: Homo Sapiens

<400> SEQUENCE: 43

Tyr Leu Ser Leu
1

<210> SEQ ID NO 44
<211> LENGTH: 14
<212> TYPE: PRT
<213> ORGANISM: Homo Sapiens

<400> SEQUENCE: 44

Asp Thr Tyr Asp Ala Leu His Met Gln Ala Leu Pro Pro Arg
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Asp Thr Tyr Asp Ala Tyr Arg His Gln Ala Leu Pro Pro Arg
1               5                   10
```

CHIMERIC ANTIGEN RECEPTORS, ENCODING NUCLEIC ACIDS AND METHODS OF USE THEREOF

RELATED APPLICATION

This application is a national phase entry of PCT/CA2016/050126 filed Feb. 11, 2016, which claims the benefit under 35 U.S.C. § 119 of U.S. Provisional Application No. 62/115,527 filed Feb. 12, 2015, which is incorporated herein in its entirety by reference.

INCORPORATION OF SEQUENCE LISTING

A computer readable form of the Sequence Listing "P47312US01_ST25.txt" (46,200 bytes) created on Dec. 27, 2018 is hereby incorporated by reference.

TECHNICAL FIELD

The present disclosure relates to improved chimeric antigen receptors (CARs) and particularly to CARs comprising an intracellular segment comprising a cytoplasmic domain of an interleukin receptor chain, and/or a cytoplasmic co-stimulatory domain, the intracellular segment comprising a JAK-binding motif and a Signal Transducer and Activator of Transcription (STAT) 5 association motif, and/or a CD3ζ intracellular signaling domain comprising an exogenous STAT3 association motif. Also provided are nucleic acids encoding said CARs, a cell expressing said CARs, as well as methods of making and use thereof.

INTRODUCTION

A therapeutic strategy for treating tumors, can involve introducing a T cell receptor (TCR) capable of binding to a specific antigen into a T cell to prepare a T cell targeting the antigen of interest. Based on this strategy, adoptive immunity gene therapies using TCR genes targeting many tumor antigens, for example, WT1, MART1, gp100, CEA, CD19 and mHAG HA-2 antigens have been attempted.

Another gene-modified T cell therapy involves using a chimeric antigen receptor (CAR). CARs combine antigen specificity and T cell activating properties in a single fusion molecule. The CAR has specificity for a surface antigen of a tumor cell and the ability to activate T cell growth ex vivo. This therapy may have a stronger and longer-lasting anti-tumor effect than a therapeutic antibody targeting the tumour surface antigen and therefore the clinical effect thereof may also be greater.

A representative structure of CAR comprises a single chain variable fragment (scFv) recognizing a surface antigen of a tumor cell, a transmembrane domain, and an intracellular signaling domain of a TCR complex—such as CD3ζ—that activates a T cell. A CAR having such a constitution is called a first generation CAR. A nucleic acid sequence encoding a single chain variable fragment portion can be isolated from, for example, a hybridoma producing a monoclonal antibody that recognizes a target antigen, such as a target tumour antigen. A CAR is produced and expressed in a cell such as a T cell. A T cell expressing a CAR directly recognizes a surface antigen of a tumor cell independently of the expression of major histocompatibility antigen class I on the tumor cell, and at the same time, activates the T cell, and thereby the CAR-expressing T cell can efficiently kill the tumor cell.

In order to attempt to enhance the ability of first generation CARs to activate T cells, a second generation CAR has been developed, wherein an intracellular signaling domain of CD28 which is a co-stimulatory molecule of a T cell, is linked to a first generation CAR. As a further improved version, a third generation CAR has also been developed, wherein an intracellular signaling domain derived from CD137 (4-1BB) or CD134 (OX40), both which are tumor necrosis factor (TNF) receptor superfamily members, is tandemly linked to a second generation CAR. Thus, many CAR molecules targeting a variety of tumor antigens have been reported (see for example Sadelain et al, 2009). However, signal transducing proteins used as the co-stimulatory intracellular signaling domain for the second generation and third generation CARs which are currently reported are limited. It is known that when linked to a CAR, not all intracellular signaling domains derived from every T cell signal transducing protein will sufficiently stimulate a T cell to damage and/or kill a target tumor cell. Therefore, finding intracellular signaling domains of signal transducing proteins that are effective when linked to a CAR is desirable.

SUMMARY

An aspect of the present disclosure is a CAR which specifically binds to a target antigen and imparts a cytotoxic activity against a target cell expressing the target antigen.

A further aspect is a cell expressing the CAR that can be used to target a cell expressing the target antigen of interest.

An aspect provides a CAR comprising i) an extracellular domain capable of binding to a predetermined antigen, ii) a transmembrane domain and iii) an intracellular segment comprising a) one or more intracellular signaling domains selected from a cytoplasmic domain of an interleukin receptor chain and/or a cytoplasmic co-stimulatory domain and b) a CD3ζ intracellular signaling domain comprising an exogenous STAT3 association motif, wherein the intracellular segment comprises an endogenous or exogenous JAK-binding motif and STAT5 association motif.

In an embodiment, the exogenous STAT3 association motif is YXXQ (SEQ ID NO: 13).

In an embodiment, the exogenous STAT3 association motif is YRHQ (SEQ ID NO: 22).

In an embodiment, the exogenous STAT3 association motif is less than 100 amino acid residues from the C terminus of the CAR.

In one embodiment, the exogenous STAT3 association motif replaces amino acids 156-158 of CD3ζ.

In an embodiment, the one or more intracellular signaling domains is or comprises a cytoplasmic domain of an interleukin receptor chain.

In another embodiment, the cytoplasmic domain of an interleukin receptor chain is a truncated fragment minimally comprising a JAK-binding motif and STAT5 association motif.

In an embodiment, the one or more intracellular signaling domains is or comprises a cytoplasmic co-stimulatory domain.

In another embodiment, the cytoplasmic co-stimulatory domain is a cytoplasmic domain of CD28, CD2, CD4, CD5, CD8α, CD8β, CD134 or CD137.

Another aspect is a CAR comprising i) an extracellular domain capable of binding to a predetermined antigen, ii) a transmembrane domain and iii) an intracellular segment comprising one or more intracellular signaling domains including a cytoplasmic domain of an interleukin receptor chain and optionally at least one supplementary cytoplasmic domain.

In an embodiment, the cytoplasmic domain of an interleukin receptor chain is a truncated fragment comprising a tyrosine kinase association motif and a STAT association motif.

In an embodiment, the at least one supplementary cytoplasmic domain is i) an intracellular signaling domain of CD3ζ, optionally wherein the CD3ζ intracellular signaling domain comprises an exogenous STAT3 association motif ii) and/or a cytoplasmic co-stimulatory domain of CD28.

In an embodiment, the interleukin receptor chain is selected from the group consisting of interleukin 2 receptor (IL-2R) β chain and interleukin 21 receptor (IL-21R) α chain.

In yet another embodiment, the extracellular domain is and/or comprises an antigen binding region of an antibody capable of binding to the predetermined antigen.

In another embodiment, the antigen binding region of the antibody is or comprises a single chain variable fragment of said antibody.

In another embodiment, the transmembrane domain is selected from the group consisting of CD28 transmembrane domain and CD8 transmembrane domain.

In another embodiment, the CAR further comprises a signal peptide, optionally at the N terminus.

Another aspect includes a nucleic acid encoding a CAR described herein.

In an embodiment, the nucleic acid encodes a CAR conjugated to a signal peptide optionally wherein the signal peptide is at the N terminus of the CAR.

A further aspect includes a vector comprising a nucleic acid described herein.

Yet a further aspect includes a cell which expresses the CAR herein described, and/or is transfected or transduced with the nucleic acid or the vector described herein.

Yet a further aspect includes a composition comprising a CAR nucleic acid or vector described herein, optionally a microsomal preparation comprising a CAR described herein.

In an embodiment, the composition comprises a diluent or pharmaceutically acceptable excipient.

According to the present disclosure, there are provided chimeric antigen receptors, nucleic acids encoding said chimeric antigen receptors, cells expressing said chimeric antigen receptors and compositions comprising any of the foregoing. In an embodiment, one or more of the foregoing may be used in the field of adoptive immunity gene therapy targeting an antigen such as a tumor antigen and/or in screening or other in vitro assays. The chimeric antigen receptor of the present disclosure can be introduced into a cell, resulting for example in an increased or elevated expression amount of the chimeric antigen receptor in the cell. Such cell may exhibit cytotoxic activity against cells expressing the target antigen.

In one aspect, there is provided a method of making the cell expressing a CAR herein disclosed, the method comprising:

a) isolating immune cells from a mammal, optionally wherein the immune cells are T cells;

b) transfecting or transducing the isolated immune cells, optionally T cells, with a nucleic acid encoding a CAR disclosed herein; and c) optionally isolating and/or expanding the CAR-expressing cells, optionally CAR-expressing T cells following transfection or transduction.

Another aspect is a use of a CAR, a nucleic acid, a vector, a cell or a composition described herein for example for reducing the number of cells expressing a predetermined antigen, treating a disease, preventing a disease and/or providing anti-tumor immunity.

Another aspect includes a method of decreasing in a subject the number of cells expressing a predetermined antigen, the method comprising administering to the subject in need thereof an effective amount of cells expressing a CAR described herein, wherein the CAR specifically binds to the predetermined antigen.

Another aspect is a method of treating or preventing a disease in a mammal, the method comprising administering to the mammal in need thereof an effective amount of cells expressing a CAR described herein or a composition described herein.

A further aspect is a method of providing an anti-tumor immunity in a mammal, the method comprising administering to the mammal in need thereof an effective amount of cells expressing a CAR described herein or a composition described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF DRAWINGS

An embodiment of the present disclosure will now be described in relation to the drawings in which:

FIG. 3 is a series of graphs showing anti-CD19-CAR surface expression of various constructs.

FIG. 11 is a series of graphs showing cell division rate in CAR-transduced T cells.

DETAILED DESCRIPTION

Figure 1:
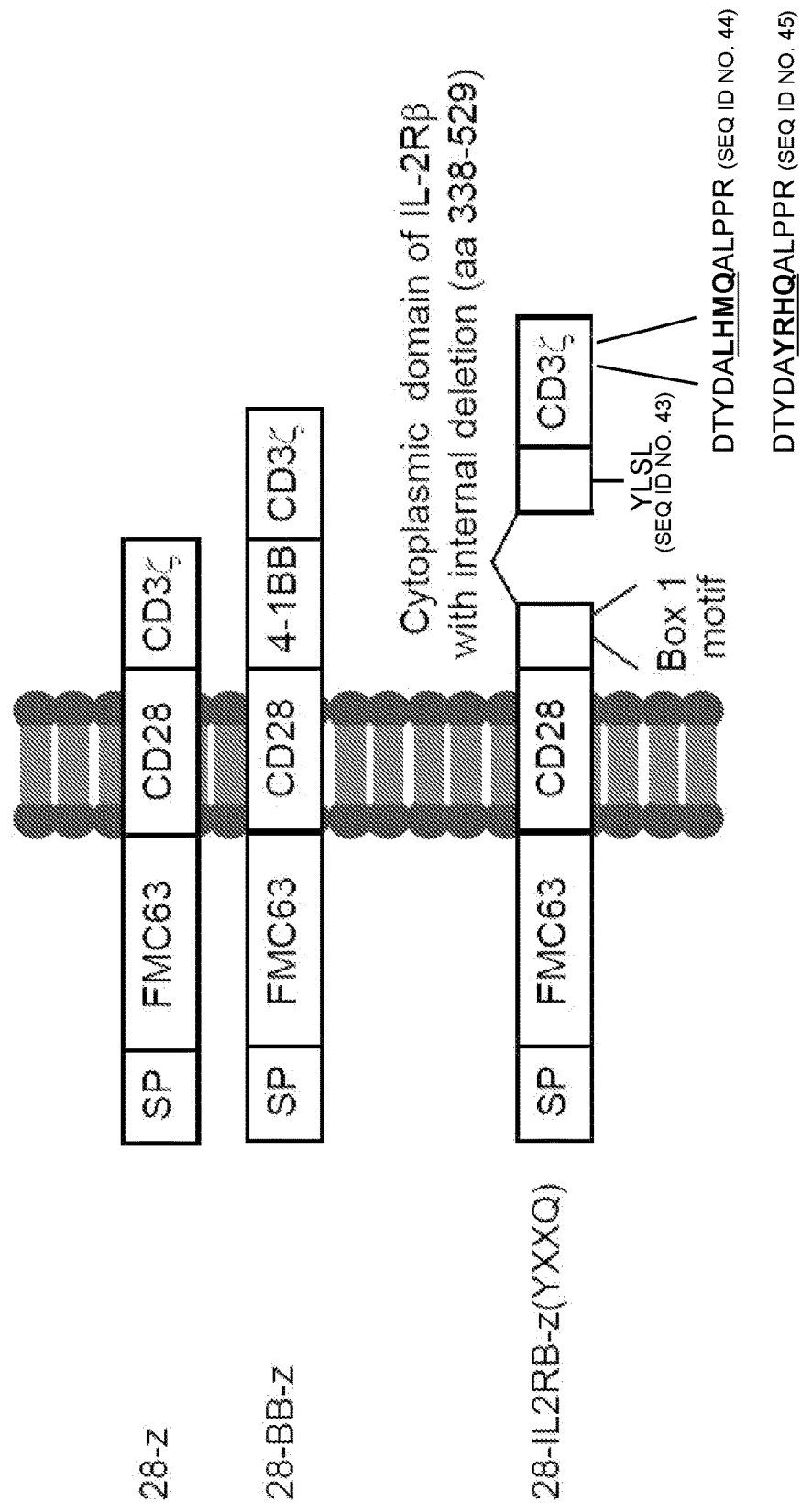
FIG. 1 is a schematic diagram of anti-CD19 chimeric antigen receptor (CAR) constructs.

As used herein, a "chimeric antigen receptor (CAR)" means a fused protein comprising an extracellular domain capable of binding to a predetermined antigen, an intracellular segment comprising one or more cytoplasmic domains derived from signal transducing proteins different from the polypeptide from which the extracellular domain is derived, and a transmembrane domain. The "chimeric antigen receptor (CAR)" is sometimes called a "chimeric receptor", a "T-body", or a "chimeric immune receptor (CIR)." The phrase "extracellular domain capable of binding to a predetermined antigen" means any proteinaceous molecule or part thereof that can specifically bind to the predetermined antigen. The "intracellular signaling domain" means any oligopeptide or polypeptide domain known to function to transmit a signal causing activation or inhibition of a biological process in a cell, for example, activation of an immune cell such as a T cell or a NK cell. Examples include ILR chain, CD28 and/or CD3ζ.

As used herein, "STAT3" or "Signal Transducer and Activator of Transcription 3" refers to a transcription factor belonging to the STAT protein family. STAT3 is also referred to as "acute-phase response factor", "APRF", "APRF Transcription Factor", DNA-binding protein APRF", FLJ20882", hypothetical protein MGC16063", "IL-6-Response Factor", "LIF (leukemia inhibitory factor)-Response Factor" or "STAT3_HUMAN". The STAT3 protein is involved in regulating genes that are involved in cell growth and division, cell movement and cell apoptosis. In the immune system, STAT3 is a signal transducer for the maturation of immune system cells such as T cells and B cells. Siegel et al. have shown that STAT3 plays a role for the development and maintenance of human T cell memory (Siegel et al. 2011).

As used herein a "Signal Transducer and Activator of Transcription 3 association motif" or a "STAT3 association motif" refers to amino acid sequence (or a polynucleotide encoding said amino acid sequence according to the context) YXXQ (SEQ ID NO: 13) and which binds STAT3 (for example in the context of a longer polypeptide/protein). The STAT3 association motif is present in signaling proteins, for example IL-6 and IL-10. The STAT3 association motif can also be introduced into signaling domains which do not endogenously comprise the STAT3 association motif (i.e. exogenous STAT3 association motif). The term "exogenous STAT3 association motif" means a STAT3 association motif that is recombinantly introduced into a domain, for example a CD3ζ intracellular signaling domain, but that does not exist natively in said domain or at the introduced location in the domain. For example, a YXXQ (SEQ ID NO: 13) exogenous STAT3 association motif can be introduced into CD3ζ. The exogenous STAT3 association motif can, for example, be YRHQ (SEQ ID NO: 22). A person skilled in the art will appreciate that the exogenous STAT3 association motif can be introduced into CD3ζ using various techniques understood in the art.

As used herein a "Signal Transducer and Activator of Transcription 5 association motif" or a "STAT5 association motif" refers to an amino acid sequence (or a polynucleotide encoding said amino acid sequence according to the context) that comprises a tyrosine residue and which binds STAT5. For example, the STAT5 association motif of the IL-2R β chain comprises tyrosine residue-510 (tyrosine residue 510 which is amino acid number 536 of NCBI RefSeq: NP_000869.1, e.g. 271 of SEQ ID NO: 11). For example, the STAT5 association motif comprises amino acid residues YXXL (SEQ ID NO: 41). For example, the STAT5 association motif comprises amino acid residues YLSL (SEQ ID NO: 43).

The term "exogenous association motif" means any association motif that is recombinantly introduced into a domain, for example an intracellular signaling domain such as a cytoplasmic domain of an interleukin receptor chain, a cytoplasmic co-stimulatory domain or a CD3ζ intracellular signaling domain, but that does not exist natively in said domain or at the introduced location in the domain. For example, an exogenous JAK-binding motif can be inserted into an intracellular signaling domain, for example a cytoplasmic domain of an interleukin receptor chain.

The "JAK-binding motif" used herein refers to a BOX-1 motif which allows for tyrosine kinase JAK association, for example JAK1. The JAK-binding motif can be for example amino acid numbers 278 to 286 of NCBI RefSeq: NP_000869.1 (amino acids 13 to 21 SEQ ID NO: 11).

As used herein, a "domain" means one region in a polypeptide, for example which is folded into a particular structure independently of other regions and/or has a particular function. The domain can for example be the cytoplasmic portion of a molecule or a part thereof. As used herein, the "cytoplasmic domain" of a molecule can refer to the full cytoplasmic domain or a part thereof that induces an intracellular signal when activated.

The term "variant" means a molecule comprising substitution, deletion or addition of one or a few to a plurality of amino acids, and includes particularly conservatively substituted molecules, provided that the variant substantially retains the same function as the original sequence. For example, IL receptor variants may comprise substitutions, deletions or additions outside the JAK-binding motif and the STAT association motif. For example, a IL receptor chain variant can comprise up to 50, up to 40, up to 30, up to 20 or up to 10 amino acid deletion and/or conservative substitutions, in a region outside of the JAK-binding and STAT association motifs. Similarly variants of other molecules can comprise up to 50, up to 40, up to 30, up to 20 or up to 10 amino acid deletion and/or conservative substitutions, in a region outside of a region identified specifically herein.

As used herein, the phrase "wherein the intracellular segment comprises an endogenous or exogenous JAK-binding motif and a STAT5 association motif" means in the case wherein the intracellular segment comprises more than one cytoplasmic domain, that the JAK binding motif and the STAT5 association motif may be in the same cytoplasmic domain or may be in separate cytoplasmic domains.

The term "supplementary cytoplasmic domain" as used herein in the context of a CAR comprising a cytoplasmic domain of an interleukin receptor (ILR) chain is a cytoplasmic domain of a signal transducing protein that is not comprised in the ILR chain.

As used herein, a "tumor antigen" means a biological molecule having antigenicity, the expression of which comes to be recognized in association with malignant alteration of a cell. The tumor antigen in the present disclosure includes a tumor specific antigen (an antigen which is present only in tumor cells and is not found in other normal cells), and a tumor-associated antigen (an antigen which is also present in other organs and tissues or heterogeneous and allogeneic normal cells, or an antigen which is expressed during development and/or differentiation).

As used herein, an "interleukin (IL) receptor" means a cytokine receptor for an interleukin. There are two main families of IL receptors, type 1 and type 2 cytokine receptors. Type 1 interleukin receptors include IL-2 receptor, IL-3 receptor, IL-4 receptor, IL-5 receptor, IL-6 receptor, IL-7 receptor, IL-9 receptor, IL-11 receptor, IL-12 receptor, IL-13 receptor, IL-15 receptor, IL-21 receptor, IL-23 receptor and IL-27 receptor. Type 2 IL receptors include IL-10 receptor, IL-20 receptor, IL-22 receptor and IL-28 receptor. The IL receptor is composed of multiple polypeptide chains. In the present specification, for example, the IL-2 receptor β chain is sometimes abbreviated as IL2Rb or IL-2Rb.

The term "antibody" as used herein is intended to include monoclonal antibodies, polyclonal antibodies, and mouse-human chimeric antibodies, humanized antibodies as well as murine, bovine, rabbit, rat, goat, human antibodies and other organism-derived antibodies. The antibody may be from recombinant sources and/or produced in transgenic animals. The antibody may also be synthetic. The term "antibody fragment" as used herein is intended to include without limitations Fab, Fab', F(ab')2, scFv, dsFv, ds-scFv, dimers, heterodimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Methods for making antibodies are known in the art. To produce human monoclonal antibodies and/or binding fragments thereof, antibody producing cells (lymphocytes) can be harvested from a human having cancer and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121:140-67 (1986)), and screening of combinatorial antibody libraries (Huse et al., *Science* 246:1275 (1989)). Hybridoma cells can be screened immunochemically for production of antibodies specifically reactive with cancer cells and the monoclonal antibodies can be isolated.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known, and include methods described in U.S. Pat. No. 4,694,778, Science, vol. 242, pp. 423-442 (1988), Nature, vol. 334, p. 54454 (1989), and Science, vol. 242, pp. 1038-1041 (1988).

The term "CD3ζ" as used herein refers to all mammalian species, preferably human, of the cluster of differentiation 3 (CD3) T-cell co-receptor. In mammals, CD3 comprises a CD3 ζ chain, a CD3 delta chain and two CD3 epsilon chains. The CD3ζ chain (e.g. NCBI RefSeq: NP_932170.1) comprises an intracellular signaling domain (e.g. SEQ ID NO: 7) which can be used to engineer the CAR of the present disclosure.

The term "28-z" as used herein refers to a CAR construct generated by linking a FMC63-derived single-chain variable fragment (scFv) to a CD28 transmembrane domain and a CD3ζ intracellular domain.

The term "28-BB-z" as used herein refers to a CAR construct generated by linking a FMC63-derived single-chain variable fragment (scFv) to a CD28 transmembrane domain and further to a 4-1BB intracellular signaling domain and a CD3ζ intracellular signaling domain.

The term "28-IL2RB-z (YXXQ)" as used herein refers to a CAR construct generated by linking a FMC63-derived single-chain variable fragment (scFv) to a CD28 transmembrane domain, to an IL-2Rβ cytoplasmic domain comprising a BOX 1 motif involved in JAK signaling (e.g. comprises a JAK-binding motif) and a tyrosine residue at position 510 for STAT5 association, and further to a CD3ζ intracellular signaling domain comprising an exogenous YXXQ (SEQ ID NO: 13) motif involved in STAT3 association.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "isolated nucleic acid" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences, for example cDNA.

The term "isolated polypeptide", also referred to as "isolated protein" refers to a polypeptide substantially free of cellular material or culture medium when produced by recombinant DNA techniques, or chemical precursors or other chemicals when chemically synthesized.

The term "amino acid" includes all of the naturally occurring amino acids as well as modified amino acids.

A "conservative amino acid variation" as used herein, is one in which one amino acid residue is replaced with another amino acid residue without abolishing the protein's desired properties.

The term "subject" as used herein includes all members of the animal kingdom including a human.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment. "Palliating" a disease or disorder, means that the extent and/or undesirable clinical manifestations of a disorder or a disease state are lessened and/or time course of the progression is slowed or lengthened, as compared to not treating the disorder.

As used herein, the phrase "treating or preventing cancer" refers to inhibiting of cancer cell replication, providing anti-tumor immunity, inhibiting cancer spread (metastasis), inhibiting tumor growth, reducing cancer cell number or tumor growth, or improving cancer-related symptoms.

The term "administered" as used herein means administration of a therapeutically effective amount for example of cells expressing a CAR to reduce and/or inhibit spread of cells expressing the predetermined antigen or a composition of the application to a patient.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

(1) CARs of the Present Disclosure

Disclosed herein is a CAR comprising i) an extracellular domain capable of binding to a predetermined antigen, ii) a transmembrane domain and iii) an intracellular segment comprising one or more intracellular signaling domains selected from a cytoplasmic co-stimulatory domain and/or a cytoplasmic domain of interleukin receptor chain, and a CD3ζ intracellular signaling domain comprising an exogenous STAT3 association motif, wherein the intracellular segment comprises an endogenous or exogenous JAK-binding motif and STAT5 association motif. In an embodiment, the domains are fused directly or indirectly optionally in the foregoing order starting from the N-terminus. In an embodiment, the domains in the intracellular segment are fused in a reversed order.

Also disclosed herein is a CAR comprising i) a extracellular domain capable of binding to a predetermined antigen, ii) a transmembrane domain and iii) an intracellular segment comprising one or more intracellular signaling domains including a cytoplasmic domain of an IL receptor chain and optionally at least one supplementary cytoplasmic domain. In an embodiment, the domains are fused directly or indirectly optionally in the foregoing order starting from the N-terminus. In one embodiment, the domains in the intracellular segment are fused in a reversed order.

In some embodiments, the IL receptor chain is proximal to the transmembrane domain and/or is towards or forms the N-terminus of the CAR intracellular segment. In other embodiments, the IL receptor chain is towards or forms the C-terminus of the intracellular segment in the CAR. In some embodiments, the IL receptor chain is upstream or N-terminal to the CD3ζ intracellular signaling domain comprising an exogenous STAT3 association motif YXXQ (SEQ ID NO: 13) in the CAR.

In embodiments where the CAR intracellular segment comprises only signaling domains of the IL receptor chain, cells expressing the CAR can be activated by predetermined antigen presented in a MHC complex via endogenous TCRs and/or by CD80/86 molecules via endogenous CD28, for example by B cells.

Also provided is a cell expressing a CAR of the present disclosure. Such a cell may for example have an increased proliferation rate and/or increased survivability, may produce increased amounts of cytokines, and/or can have increased cytotoxic activity against a cell having, on the surface, the predetermined/preselected antigen to which the CAR binds relative to a parent cell not expressing the CAR. For example, as shown in the Examples, the 28-IL2RBz (YXXQ) CAR-transduced T cells have increased cell division, proliferation and viability, provide anti-tumor effects and improve overall survival in mice receiving said cells as treatment.

(a) Extracellular Domain

The "extracellular domain capable of binding to a predetermined antigen" used for the CAR of the present disclosure is a domain comprising a proteinaceous molecule or part thereof that can bind to a target antigen, and includes, for example, an antigen-binding domain of an antibody and a ligand-binding domain of a receptor. This domain binds to and interacts with an antigen present on a cell surface, and thereby imparts specificity to a cell expressing a CAR. For example, the extracellular domain used for the CAR of the present disclosure comprises and/or is derived from variable regions of an antibody (e.g. H chain and L chain), single chains and binding fragments thereof or a TCR (TCRα, TCRβ, TCRγ, TCRδ), or is derived from CD4 ectodomain, CD8α, CD8β, CD11A, CD11B, CD11C, CD18, CD29, CD49A, CD49B, CD49D, CD49E, CD49F, CD61, CD41, and/or CD51. The entire region of these proteins may be used. On the other hand, a domain capable of binding to an antigen or a ligand, for example, an antibody Fab fragment, an antibody variable region [V region of H chain (VH) and V region of L chain (VL)] or an extracellular ligand binding domain of a receptor can be used. Particularly, in an embodiment, a single chain variable fragment (scFv) can be used. For example, the CD4 ectodomain can recognize HIV-infected cells.

The extracellular domain for the CAR of the present disclosure may bind to only one antigen or ligand, or bind to two or more antigens or ligands. In addition, the present disclosure includes both a CAR comprising one extracellular domain and a CAR comprising two or more extracellular domains.

The extracellular domain for the CAR of the present disclosure can be selected from antibodies recognizing a target antigen, optionally a cell surface antigen or soluble antigen, or molecules interacting with the antigen. Examples of the antigen include a viral antigen, a bacterial (particularly, infectious bacteria) antigen, a parasite antigen, a cell surface marker on a target cell related to a certain condition (e.g. a tumor antigen), and a surface molecule of an immunocyte.

The present disclosure in one aspect provides a CAR capable of binding to an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

The present disclosure in another aspect provides a CAR capable of binding to an antigen derived from a bacterial strain of Staphylococci, *Streptococcus*, *Escherichia coli*, *Pseudomonas*, or *Salmonella*. Particularly, the present disclosure provides a CAR capable of binding to an antigen derived from an infectious bacterium, for example, *Helicobacter pyloris*, *Legionella pneumophilia*, a bacterial strain of Mycobacteria sps. (e.g. *M. tuberculosis*, *M. avium*, *M. intracellulare*, *M. kansaii*, or *M. gordonea*), *Staphylococcus aureus*, *Neisseria gonorrhoeae*, *Neisseria meningitides*, *Listeria monocytogenes*, *Streptococcus pyogenes*, Group A *Streptococcus*, Group B *Streptococcus* (*Streptococcus agalactiae*), *Streptococcus pneumoniae*, or *Clostridium tetani*.

The present disclosure in another aspect provides a CAR capable of binding to a tumor antigen such as 5T4, α 5β1-integrin, 707-AP, AFP, ART-4, B7H4, BAGE, β-catenin/m, Bcr-abl, MN/C IX antibody, CA125, CAMEL, CAP-1, CASP-8, CD4, CD19, CD20, CD22, CD25, CDC27/m, CD30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HST-2, hTERT (or hTRT), iCE, IGF-1R, IL-2R, IL-5, KIAA0205, LAGE, LDLR/FUT, MAGE, MART-1/melan-A, MART-2/Ski, MC1R, myosin/m, MUC1, MUM-1, MUM-2, MUM-3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TEL/AML1, TGFβ, TPI/m, TRP-1, TRP-2, TRP-2/INT2, VEGF, WT1, NY-Eso-1 or NY-Eso-B. The present disclosure also provides a CAR capable of binding to a cell surface adhesion molecule, a surface molecule of an inflammatory cell that appears in an autoimmune disease, or a TCR causing autoimmunity.

(b) Intracellular Segment

The intracellular segment of the CAR according to the present disclosure is a proteinacious molecule that can comprise one or more intracellular signaling domains and that can transduce a signal into a cell when the extracellular domain present within the same molecule binds to (interacts with) its cognate antigen/ligand.

In an aspect, the CAR intracellular segment comprises a CD3ζ intracellular signaling domain comprising an exogenous STAT3 association motif. In addition, the CAR intracellular segment comprises one or more intracellular signaling domains selected from a cytoplasmic domain of an IL receptor chain and/or a cytoplasmic co-stimulatory domain, wherein the intracellular segment comprises an endogenous or exogenous JAK-binding motif and STAT5 association motif.

A primary cytoplasmic signaling sequence can regulate primary activation of a TCR complex. For example, the CD3ζ intracellular signaling domain provides a primary cytoplasmic signal. The primary cytoplasmic signaling sequence may comprise a signal transduction motif known as an immunoreceptor tyrosine-based activation motif (ITAM) [Nature, vol. 338, pp. 383-384 (1989)]. On the other hand, a primary cytoplasmic signaling sequence that acts in an inhibitory way comprises a signal transduction motif known as an immunoreceptor tyrosine-based inhibition motif (ITIM) [J Immunol., vol. 162, No. 2, pp. 897-902 (1999)]. In the present disclosure, an intracellular signaling domain having an ITAM and/or an ITIM can be used.

Examples of intracellular signaling domains having an ITAM that can be used, for example instead of or to replace CD3ζ, include intracellular signaling domains having ITAM derived from CD3ζ, FcRγ, FcRβ, CD3γ, CD3δ, CD3ε, CD5, CD22, CD79a, CD79b, and CD66d. Specifically, examples of intracellular domains comprising one or more ITAM include peptides having sequences of amino acid numbers 52 to 164 (SEQ ID No.: 7) of CD3ζ (NCBI RefSeq: NP_932170.1), amino acid numbers 45 to 86 of FcεRIγ (NCBI RefSeq: NP_004097.1), amino acid numbers 201 to 244 of FcεRIβ (NCBI RefSeq: NP_000130.1), amino acid numbers 139 to 182 of CD3γ (NCBI RefSeq: NP_000064.1), amino acid numbers 128 to 171 of CD3δ (NCBI RefSeq: NP_000723.1), amino acid numbers 153 to 207 of CD3ε (NCBI RefSeq: NP_000724.1), amino acid numbers 402 to 495 of CD5 (NCBI RefSeq: NP_055022.2), amino acid numbers 707 to 847 of CD22 (NCBI RefSeq: NP_001762.2), amino acid numbers 166 to 226 of CD79a (NCBI RefSeq: NP_001774.1), amino acid numbers 182 to 229 of CD79b (NCBI RefSeq: NP_000617.1), and amino acid numbers 177 to 252 of CD66d (NCBI RefSeq: NP_001806.2), and their variants having the same function as these peptides. The amino acid numbering based on amino acid sequence information of NCBI RefSeq ID or GenBank described herein is numbered based on the full length of the precursor (comprising a signal peptide sequence etc.) of each protein.

In embodiments where CD3ζ is replaced with one of the foregoing, the exogenous STAT3 association motif is introduced in the CD3ζ replacement.

STAT3 transcription factor signaling plays an important role in the development and maintenance of human T cell memory (Siegel et al. 2011). STAT3 signaling may also in T cells enhance in vivo anti-tumor effects (Blood. 2010 and J Exp Med. 2005).

In an embodiment, the exogenous STAT3 association motif is YXXQ (SEQ ID NO: 13). As demonstrated, the exogenous STAT3 association motif YXXQ (SEQ ID NO: 13) comprised in the intracellular signaling domain of a CD3ζ signal transducing peptide is capable of STAT3 binding. In an embodiment, the intracellular domain of CD3ζ is the sequence in SEQ ID NO: 7.

In an embodiment, the amino acid residues represented by "X" in the STAT3 association motif YXXQ (SEQ ID NO: 13) can be any naturally occurring amino acid, including any modified naturally occurring amino acid that retains STAT3 binding. In one embodiment, the amino acid X is independently chosen from leucine, arginine, histidine, phenylalanine, lysine, proline, methionine, valine, glutamine, threonine an aspartate. For example, the amino acid X is arginine. For example, the amino acid X is histidine.

In an embodiment, the two amino acid residues flanking the tyrosine residue are arginine-histidine. In yet another embodiment, the exogenous STAT3 association motif is YRHQ (SEQ ID NO: 22).

Although the exogenous STAT3 association motif YXXQ (SEQ ID NO: 13) may be introduced in any portion of the intracellular domain of CD3ζ, in an embodiment the YXXQ association motif in inserted near the C-terminus region. Without wishing to be bound by theory, many endogenous YXXQ motifs are located near or within 100 aa from the C-terminus. Also a YXXQ motif located near the C-terminus region has been shown to be more functional than that in a more proximal site in GP130 and LIFR studies (Schmitz J et al. J Immunol. 2000; 164:848-54; Tomida M et al. Blood. 1999; 93:1934-41).

In an embodiment, the exogenous STAT3 association motif YXXQ (SEQ ID NO: 13) is introduced in any portion of the intracellular domain of CD3ζ that is located within 200 amino acid residues from the C terminus of the CAR. For example, the STAT3 association motif is introduced less than 200, less than 150, less than 100, less than 90, less than 80, less than 70, less than 60, less than 50, less than 40, less than 30, less than 20 or less than 10 amino acid residues from the C terminus of the CAR.

As discussed herein, the intracellular domain of CD3ζ comprises immunoreceptor tyrosine-based activation motifs (ITAM). In one embodiment, the exogenous STAT3 association motif is introduced elsewhere than in an ITAM.

ITAMs are functionally redundant; however they have additive effects with respect to the strength of signaling responses. For example, the intracellular domain of CD3ζ comprises three ITAMs for intracellular signaling. Therefore in one embodiment the ITAM motifs in the CD3ζ intracellular domain of the CAR herein disclosed are maintained.

In an embodiment, the CD3ζ intracellular domain comprising an exogenous STAT3 association motif comprises at least one ITAM motif. In one embodiment, the CD3 ζ intracellular domain comprising an exogenous STAT3 association motif comprises two ITAM motifs. In a further embodiment, the CD3ζ intracellular domain comprising an exogenous STAT3 association motif comprises three ITAM motifs.

The person of skill in the art will appreciate that several methods may be used to introduce a STAT3 association motif into the intracellular signaling domain of CD3ζ. For example, as shown in FIG. 1, an exogenous STAT3 association motif can be introduced by substituting amino acid residues Leu-His-Met at position 104-106 with a tyrosine at residue 104 and any other two amino acid residues flanking the tyrosine residue at positions 105 and 106, thereby forming the YXXQ (SEQ ID NO: 13) association motif. Amino acid residues 104-105-106 of the intracellular signaling domain of CD3ζ correspond to amino acid residues 156-157-158 of the full length CD3ζ (e.g. NCBI RefSeq: NP_932170.1). The sequence of 28-IL2RB-z (YXXQ) comprising a YXXQ motif at residues 104-107 of the CD3ζ intracellular domain is provided in SEQ ID NO: 24. The sequence of 28-IL2RB-z (YRHQ) comprising a YRHQ (SEQ ID NO: 22) motif at residues 104-107 of the CD3ζ intracellular domain (a CD3 ζ intracellular domain is shown at residues 475-586 of SEQ ID NO: 25).

For example, the STAT3 motif can be introduced by site-directed mutagenesis using for example the Gibson Assembly Method. The following primers can be used for the Gibson Assembly: forward, ACGCCTATCGCCATCA-GGCCCTGC (SEQ ID NO: 26); and reverse, CTGATGGC-GATAGGCGTCGTAGGTGT (SEQ ID NO: 27). Other methods that can be used include for example, PCR-based technologies, for example polymerase incomplete primer extension (PIPE) cloning, sequence and ligation-independent cloning (SLIC) and overlap extension cloning (OEC) (Klock et al., 2008; Li et al., 2007; Bryskin et al., 2010; Unger et al., 2010).

As mentioned, the CAR in an embodiment comprises an intracellular segment comprising one or more intracellular signaling domains selected from a cytoplasmic domain of an ILR chain and a cytoplasmic co-stimulatory domain.

The cytoplasmic domain of an IL receptor chain used for the present disclosure may be selected from any chain of the IL receptor, for example, the cytoplasmic domain comprising amino acid numbers 266 to 551 of IL-2 receptor β chain (NCBI REFSEQ: NP_000869.1)(SEQ ID NO: 11, amino acid numbers 256 to 538 of IL-21 receptor α chain (NCBI REFSEQ: NP_068570.1; SEQ ID NO: 6) amino acid numbers 284 to 369 of common IL-2 receptor γ chain (NCBI REFSEQ: NP_000197.1), amino acid numbers 265 to 459 of IL-7Rα (NCBI REFSEQ: NP_002176.2), amino acid numbers 292 to 521 of IL-9Rα (NCBI REFSEQ: NP_002177.2) or amino acid numbers 257 to 825 of IL-4Rα (NCBI REFSEQ: NP_000409.1) may be used. The entire region of the cytoplasmic domain of IL receptor chain may be used (e.g. sequences provided herein).

Alternatively, a truncated fragment of said cytoplasmic domain of IL receptor chain also may be used. For example, the truncated fragment comprises up to 250 amino acids, or is 50 to 200 amino acids or 80 to 150 amino acids of the ILR cytoplasmic domain.

In an embodiment, the cytoplasmic domain of IL receptor chain, optionally a truncated fragment of said cytoplasmic domain of IL receptor chain comprises at least a STAT association motif, optionally a STAT5 association motif, and a JAK-binding motif (also known as a box-1 motif). In an embodiment, the cytoplasmic domain of IL receptor chain or truncated fragment thereof comprises a STAT5 association motif and a JAK-binding motif.

In an embodiment, the cytoplasmic domain and/or truncated fragments of IL receptor chain includes variants having the same function, e.g. variants that induce STAT signaling, optionally STAT5 signaling and/or JAK signaling.

In one aspect of the present disclosure, the cytoplasmic domain of IL-2 receptor (IL-2R) β chain may be used. An example of a cytoplasmic domain of IL-2R β chain that can be used in the present disclosure includes amino acid numbers 266 to 551 of IL-2R β chain (NCBI RefSeq: NP_000869.1, SEQ ID NO: 11). In one aspect of the present disclosure, a truncated fragment of the cytoplasmic domain of IL-2R β chain may be used. The truncated fragment may comprise i) a JAK-binding motif (e.g. amino acid numbers 278 to 286 of NCBI RefSeq:NP_000869.1), also referred to as the BOX-1 motif, which allows for association with the tyrosine kinase JAK1, and ii) a STAT association motif, optionally a STAT5 or STAT3 association motif. Other portions of the IL receptor chain can be varied, for example with conservative amino acid variations.

In an embodiment, the intracellular segment can comprise an exogenous JAK binding motif, or a signaling molecule comprising a JAK binding motif. For example, the JAK-binding motif is from IL2Rgamma (IL2RG), Erythropoietin receptor (EpoR), thrombopoietin receptor (TpoR), granulocyte macrophage colony stimulating factor receptor (GM-CSFR), and growth hormone receptor (GHR).

The IL-2R β chain comprises three functional STAT5 binding motifs, YFFF (SEQ ID NO: 28), YCTF (SEQ ID NO: 29) and YLSL (SEQ ID NO: 43), used for STAT5 association. Mutations of these tyrosine residues can abolish IL-2 responsiveness of IL-2R β chain (Friedmann et al., 1996). It has been described that the erythropoietin receptor (EpoR) comprises two tyrosine residues that mediate STAT5 activation, namely Y343 and Y401 and both have YXXL motifs (SEQ ID NO: 41) (Klingmüller et al., 1996). Therefore YXXL (SEQ ID NO: 41) may be a preferred motif for STAT5 recruitment. Other amino acid residues are also functional, as shown for example with the IL-2R β chain STAT5 binding motifs. In one embodiment, the STAT5 association motif is the IL-2R β chain STAT5 association motif and comprises tyrosine residue-510 (tyrosine residue 510 is amino acid number 536 of NCBI RefSeq: NP_000869.1).

In an embodiment, a STAT5 association motif can be derived from IL2Rgamma, EpoR, TpoR, GM-CSFR and GHR.

In an embodiment, the STAT5 association motif of the IL-2R β chain comprises amino acid residues YXXL (SEQ ID NO: 41). In an embodiment, the amino acid residues represented by "X" in the STAT5 association motif can be any naturally occurring amino acid, including any modified naturally occurring amino acid that retains STAT5 binding.

In an embodiment, the STAT5 association motif comprises tyrosine residue 510 and the flanking 4 residues on at the C-terminal side of tyrosine residue 510, i.e. YLSLQ (SEQ ID NO:12).

The STAT5 association motif can exist endogenously in a cytoplasmic domain. For example, the cytoplasmic domain of the IL-2R beta chain comprises a STAT5 association motif. The STAT5 association motif can also be introduced in a cytoplasmic domain that does not naturally express this motif. For example, the STAT5 association can be introduced for example by amino acid residue replacement or insertion, using known methods including those described herein.

Other STAT3 association motifs are also known and include for example YLRQ (SEQ ID NO: 30) for IL21R; YRHQ (SEQ ID NO: 22), YFKQ (SEQ ID NO: 31), YLPQ (SEQ ID NO: 32) and YMPQ (SEQ ID NO: 33) for IL6ST; YVLQ (SEQ ID NO: 34) for GCSFR, YQPQ (SEQ ID NO: 35), YKPQ (SEQ ID NO: 36) and YRPQ (SEQ ID NO: 37) for LIFR; YTHQ (SEQ ID NO: 38) for FGFR1; YLRQ (SEQ ID NO: 30) and YLKQ (SEQ ID NO: 39) for IL10RA and YHNQ (SEQ ID NO: 40) for EGFR (Shao et al., 2004).

In an embodiment, the intracellular segment comprises STAT3 and STAT5 association motifs, including multiple STAT3 and/or multiple STAT5 association motifs.

The STAT3 and STAT5 association motifs can for example be located or introduced into any of the intracellular signaling domains.

Similarly, the intracellular segment comprises one or more JAK-binding motifs, which can be located or introduced into any of the intracellular signaling domains.

A BOX-1 MOTIF is also shown in amino acids 13-21 of SEQ ID NO: 5 and the tyrosine residue-510 is also shown as amino acid number 79 of SEQ ID NO: 5 (and the motif flanking the tyrosine residue is amino acids 80-83). In an embodiment, the interleukin receptor cytoplasmic domain fragment comprises amino acids 22-78 of SEQ ID NO: 5. Examples of the truncated fragment of the cytoplasmic domain of IL-2R β chain (SEQ ID No.: 5) include peptides having sequences of amino acid numbers 266 to 337 and 530 to 551 of NCBI RefSeq: NP_000869.1.

In one aspect of the present disclosure, the cytoplasmic domain of IL-21 receptor (IL-21R) α chain may be used. An example of the cytoplasmic domain of IL-21R α chain used in the present disclosure includes an intracellular signaling domain comprising amino acid numbers 256 to 538 of IL-21R α chain (NCBI RefSeq: NP_068570.1, SEQ ID No.: 6). In one aspect of the present disclosure, a truncated fragment of the cytoplasmic domain of IL-21R α chain may be used. The truncated fragment includes a box-1 motif (amino acid numbers 266 to 274 of NCBI RefSeq: NP_068570.1) required for association with the tyrosine kinase JAK1, and includes a STAT association motif. In an embodiment, the STAT association motif comprises tyrosine residue-500 (amino acid number 519 of NCBI RefSeq: NP_000869.1) and flanking 3 residues at the C-terminal side of tyrosine residue 500, i.e. YLRQ (SEQ ID NO: 30), required for STAT1/3 association.

Other examples of intracellular signaling domains include cytoplasmic regions from a TCR complex and/or a costimulatory molecule, and any variant having the same function as those sequences. Other examples include cytoplasmic signaling domains listed in Table 2 of Sadelain et al 2009, which is incorporated herein by reference.

Natural T cell-activation is transduced by two different kinds of intracellular signaling domains, that is, a domain for initiating antigen-dependent primary activation via a TCR complex (primary cytoplasmic signal e.g. provided for example by CD3ζ) and a domain for acting antigen-independently to provide a secondary or costimulating signal (secondary cytoplasmic signal).

In an aspect, the CAR intracellular segment of the present disclosure comprises a CD3ζ intracellular cytoplasmic signaling domain comprising an exogenous STAT3 association motif and optionally a secondary cytoplasmic signaling sequence.

As used herein, the terms "secondary cytoplasmic signaling" and "co-stimulatory" are used interchangeably.

Examples of intracellular domains comprising a secondary or co-stimulatory cytoplasmic signaling domain that can be used in the present disclosure include sequences from CD2, CD4, CD5, CD8α, CD8β, CD28, CD134, CD137 (4-1BB), ICOS, and CD154 such as truncated fragments thereof comprising signaling motifs. Specific examples thereof include peptides having sequences of amino acid numbers 236 to 351 of CD2 (NCBI RefSeq: NP_001758.2), amino acid numbers 421 to 458 of CD4 (NCBI RefSeq: NP_000607.1), amino acid numbers 402 to 495 of CD5 (NCBI RefSeq: NP_055022.2), amino acid numbers 207 to 235 of CD8α (NCBI RefSeq: NP_001759.3), amino acid numbers 196 to 210 of CD8β (GenBank: AAA35664.1), amino acid numbers 180 to 220 (SEQ ID No.: 8) of CD28 (NCBI RefSeq: NP_006130.1), amino acid numbers 214 to 255 of CD137 (4-1BB, NCBI RefSeq: NP_001552.2), amino acid numbers 241 to 277 of CD134 (OX40, NCBI RefSeq: NP_003318.1), and amino acid numbers 166 to 199 of ICOS (NCBI RefSeq: NP_036224.1), and their variants having the same function as these peptides have.

In one embodiment, the CAR intracellular segment herein disclosed further comprises cytoplasmic co-stimulatory domain selected from CD28, CD2, CD4, CD5, CD8α, CD8β, CD134 and CD137.

The present disclosure includes in an aspect a CAR comprising an intracellular segment with one or more, for example, 2 or 3 intracellular signaling domains in addition to the intracellular signaling domain of CD3ζ comprising an exogenous STAT3 association motif.

The present disclosure also includes a CAR comprising an intracellular segment with two or more same intracellular signaling domains which are linked tandemly. In one aspect, the present disclosure provides a CAR in which a cytoplasmic domain of IL receptor is on a N-terminal side relative to an intracellular signaling domain of CD3ζ, that is, a CAR comprising a cytoplasmic domain of IL receptor and an intracellular signaling domain of CD3ζ which are linked in this order from the N-terminal side. The present disclosure also includes CARs obtained by further adding an intracellular domain of CD28 (e.g. cytoplasmic co-stimulatory domain of CD28) to the aforementioned CAR, that is, a CAR comprising an intracellular signaling domain of CD28, a cytoplasmic domain of IL receptor, and an intracellular signaling domain of CD3ζ comprising an exogenous STAT3 motif which are linked in this order from the N-terminal side.

In an embodiment, the CAR comprises an intracellular segment comprising a CD3ζ intracellular signaling domain comprising an exogenous STAT3 association motif and intracellular signaling domains selected from a cytoplasmic domain of interleukin receptor chain and a cytoplasmic co-stimulatory domain, wherein at least one of the intracellular signaling domains comprises an endogenous or exogenous JAK-binding motif and a STAT5 association motif.

In one embodiment, the CAR comprises a CD3ζ intracellular signaling domain with an exogenous STAT3 association motif, a cytoplasmic domain of IL receptor chain fragment comprising an endogenous or exogenous JAK-binding motif and STAT5 association motif, and a cytoplasmic co-stimulatory domain of CD28.

In a CAR of the present disclosure, an oligopeptide linker or a polypeptide linker can be inserted between the domains of the intracellular segment to link the domains therein and/or to link them to other domains. For example, a linker having a length of 2 to 10 amino acids can be used. Particularly, a linker having a glycine-serine continuous sequence can be used. For example, the linker IDGGGGSGGGGSGGGGS (SEQ ID NO: 42) can be introduced between the CD28 cytoplasmic domain and the partial cytoplasmic IL-2 receptor beta domain. For example, the linker KLGGSGP (SEQ ID NO: 19) can be introduced between the partial cytoplasmic IL-2 receptor beta domain and the intracellular domain of the CD3ζ chain.

In a specific embodiment, the CAR comprises an signal peptide, an FMC63 single chain variable fragment extracellular domain, a CD28 transmembrane, a CD28 cytoplasmic domain, a partial cytoplasmic IL-2 receptor beta domain comprising a JAK-binding motif and an endogenous STAT5 association motif and an intracellular signaling domain of CD3ζ comprising an exogenous STAT3 association motif, which are linked in this order from the N-terminal side, as shown for example in SEQ ID NO: 24.

In another aspect there is provided CAR comprising i) an extracellular domain capable of binding to a predetermined antigen, ii) a transmembrane domain and iii) an intracellular segment comprising one or more intracellular signaling domains including a cytoplasmic domain of an interleukin receptor chain and optionally a supplementary cytoplasmic domain.

The cytoplasmic domain of an IL receptor chain may be selected from any chain of the IL receptor herein described. The entire region of the cytoplasmic domain of IL receptor chain may be used. Alternatively, a truncated fragment of said cytoplasmic domain of IL receptor chain also may be used. Examples of full length and truncated fragments thereof are provided herein.

In an embodiment, the truncated fragment may comprise at least one tyrosine kinase association motif (also known as a box-1 motif) and a STAT (Signal Transducer and Activator of Transcription) association motif herein described. For example, the truncated fragment comprises up to 250 amino acids, or is 50 to 200 amino acids or 80 to 150 amino acids of the ILR cytoplasmic domain.

As described herein, the STAT association motif of the IL-2R β chain comprises tyrosine residue-510 (tyrosine residue 510 is amino acid number 536 of NCBI RefSeq: NP_000869.1). In an embodiment, the STAT association motif comprises tyrosine residue 510 and the flanking 4 residues on at the C-terminal side of tyrosine residue 510, i.e. YLSLQ (SEQ ID NO:12).

Other STAT association motifs are also known and include YXXQ (SEQ ID NO:13), optionally YXPQ, for IL-6, YXXQ (SEQ ID NO:13) for IL-10, YLPSNID (SEQ ID NO:14) for IL-12, YLSLQ (SEQ ID NO:12), YCTFP (SEQ ID NO:15), YFFFH (SEQ ID NO:16) for IL-2, YVTMS (SEQ ID NO:17) for IL-7, YLPQE (SEQ ID NO:18) for IL-9 and YKAFS (SEQ ID NO:20) and YKPFQ (SEQ ID NO:21) for IL-4 as indicated for example in Table 2 of Kisseleva et al 2002. Any STAT signaling domain can be used and/or introduced into the ILR chain.

In an embodiment, in addition to the cytoplasmic domain of IL receptor, the CAR intracellular segment comprises at least one supplementary signaling domain that is other than present in IL receptor. Examples of intracellular signaling domains include cytoplasmic regions from a TCR complex and/or a co-stimulatory molecule, and any variant having the same function as those sequences. Other examples include cytoplasmic signaling domains listed in Table 2 of Sadelain et al 2009, incorporated herein by reference.

In an embodiment, the CAR intracellular segment comprises a primary cytoplasmic signaling sequence and/or a secondary (e.g. co-stimulatory) cytoplasmic signaling sequence herein described as the intracellular signaling domains.

In an embodiment, the intracellular segment comprises an intracellular signaling domain having an ITAM and/or an ITIM described herein.

The present disclosure includes a CAR comprising an intracellular segment comprising one or more, for example, 2 or 3 intracellular signaling domains in addition to the cytoplasmic domain of IL receptor. For example, the CAR comprises a cytoplasmic domain of IL receptor and an intracellular signaling domain of CD3ζ. For example, the CAR comprises a cytoplasmic domain of IL receptor, an intracellular signaling domain of CD3 ζ and a cytoplasmic co-stimulatory domain of CD28.

The present disclosure also includes a CAR comprising an intracellular segment comprising two or more intracellular signaling domains which are linked tandemly. For example, the CAR comprises a cytoplasmic domain of IL receptor on a N-terminal side relative to an intracellular signaling domain of CD3ζ that is, it comprises a cytoplasmic domain of IL receptor and an intracellular signaling domain of CD3ζ which are linked in this order from the N-terminal side.

The present disclosure also includes CARs further comprising an intracellular domain of CD28 introduced into to the aforementioned CAR, that is, a CAR comprising a cytoplasmic co-stimulatory domain of CD28, a cytoplasmic domain of IL receptor, and an intracellular signaling domain of CD3ζ which are optionally linked in this order from the N-terminal side. For example, the CAR intracellular segment can comprise a cytoplasmic domain of IL receptor on a C-terminal side relative to an intracellular signaling domain of CD3ζ that is, it comprises an intracellular signaling domain of CD3ζ and a cytoplasmic domain of IL receptor which are linked in this order from the N-terminal side.

Accordingly, in an embodiment, the CAR comprises an intracellular segment comprising a CD3ζ intracellular signaling domain, one or more cytoplasmic co-stimulatory domains, wherein the intracellular segment comprises a JAK-binding motif, a STAT5 and/or STAT3 association motifs.

(c) Transmembrane Domain and Spacer Domain

The CAR of the present disclosure comprises a transmembrane domain. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3ζ chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. For example, a triplet of phenylalanine, tryptophan and valine can be found at each end of the synthetic transmembrane domain. Optionally, a short oligopeptide linker or a polypeptide linker, for example, a linker having a length of 2 to 10 amino acids can be arranged between the transmembrane domain and the intracellular segment as described herein. Particularly, a linker sequence having a glycine-serine continuous sequence can be used.

For example, a transmembrane domain having a sequence of amino acid numbers 153 to 179 (SEQ ID No.: 9) of CD28 (NCBI RefSeq: NP_006130.1) can be used as the transmembrane domain.

In the CAR of the present disclosure, a spacer domain can be arranged between the extracellular domain and the transmembrane domain, or between the intracellular segment and the transmembrane domain. The spacer domain means any oligopeptide or polypeptide that serves to link the transmembrane domain with the extracellular domain and/or the transmembrane domain with the intracellular segment. The spacer domain comprises up to 300 amino acids, for example about 10 to 100 amino acids, or about 25 to 50 amino acids.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

In an embodiment, the spacer domain is a polypeptide comprising or consisting of amino acid numbers 118 to 178 of CD8α (NCBI RefSeq: NP_001759.3) which is a hinge region of CD8α, amino acid numbers 135 to 195 of CD8β (GenBank: AAA35664.1), amino acid numbers 315 to 396 of CD4 (NCBI RefSeq: NP_000607.1), amino acid numbers 114 to 152 (SEQ ID No.: 10) of CD28 (NCBI RefSeq: NP_006130.1), or a part thereof. Further, the spacer domain may be an artificially synthesized sequence.

The CAR of the present disclosure can be designed so as to form a polymer, particularly, a dimer. For example, cysteine is inserted into the spacer domain and/or the transmembrane domain to polymerize (dimerize) the CAR, for example through a disulphide bridge.

Further, in the CAR of the present disclosure, a signal peptide sequence can be linked to the N-terminus. A signal peptide sequence exists at the N-terminus of many secretory proteins and membrane proteins, and has a length of 15 to 30 amino acids. Many of the protein molecules having an intracellular domain mentioned herein are membrane proteins, and have signal peptide sequences. The signal peptides derived from such secretory proteins and membrane proteins can be used as a signal peptide for the CAR of the present disclosure. Any signal peptide can be used. For example the signal peptide can be an Oncostatin M. signal peptide. Signal peptides can be from humans and can also be derived from non-humans, for example from insect cells or from viruses. In an embodiment, the signal peptide is a human signal peptide.

(2) Nucleic Acid Encoding CARs

The present disclosure provides a nucleic acid encoding the CAR described herein. The nucleic acid encoding the CAR can be easily prepared from an amino acid sequence of the specified CAR by a conventional method. A nucleotide sequence encoding an amino acid sequence can be obtained from the aforementioned NCBI RefSeq IDs or accession numbers of GenBank for an amino acid sequence of each domain, and the nucleic acid of the present disclosure can be prepared using a standard molecular biological and/or chemical procedure. For example, based on the nucleotide sequence, a nucleic acid can be synthesized, and the nucleic acid of the present disclosure can be prepared by combining DNA fragments which are obtained from a cDNA library using a polymerase chain reaction (PCR).

The nucleic acid of the present disclosure can be linked to another nucleic acid so as to be expressed under control of a suitable promoter. Examples of the promoter include a promoter that constitutively promotes the expression of a gene or operatively linked construct, a promoter that induces the expression of a gene or operatively linked construct by the action of a drug or the like (e.g. tetracycline or doxorubicin). The nucleic acid of the present disclosure can be also linked to, in order to attain efficient transcription of the nucleic acid, other regulatory elements that cooperate with a promoter or a transcription initiation site, for example, a nucleic acid comprising an enhancer sequence or a terminator sequence. In addition to the nucleic acid of the present disclosure, a gene that can be a marker for confirming expression of the nucleic acid (e.g. a drug resistance gene, a gene encoding a reporter enzyme, or a gene encoding a fluorescent protein) may be incorporated.

In an embodiment, the nucleic acid is codon optimized nucleic acid for expression in a particular host.

The present disclosure provides a composition comprising the nucleic acid of the present disclosure as an active ingredient, together with a pharmaceutically acceptable excipient. Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. As the pharmaceutically acceptable excipients, excipients described in Remington's Pharmaceutical Sciences (Mack Pub. Co., N.J. 1991) (which is incorporated herein by reference) can be appropriately used. The composition of the present disclosure can be formulated into a known form suitable for parenteral administration, for example, injection or infusion. Further, the composition of the present disclosure may comprise formulation additives such as a suspending agent, a preservative, a stabilizer and/or a dispersant, and a preservation agent for extending a validity term during storage. The composition may be in a dry form for reconstitution with an appropriate sterile liquid prior to use. For fine particle-mediated administration, a particle such as a gold particle of a microscopic size can be coated with a DNA.

When the nucleic acid of the present disclosure is introduced into a cell ex vivo, the nucleic acid of the present disclosure may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present disclosure is also useful as described later. Particularly, a composition in a form suitable for administration to a living body which contains the nucleic acid of present disclosure carried by a suitable vector is suitable for in vivo gene therapy.

A composition comprising the nucleic acid of the present disclosure as an active ingredient can be administered for treatment of, for example, a cancer [blood cancer (leukemia), solid tumor etc.], an inflammatory disease/autoimmune disease (asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR encoded by the nucleic acid binds. A composition comprising the nucleic acid of the present disclosure as an active ingredient can be administered or suitably formulated for administration intradermally, intramuscularly, subcutaneously, intraperitoneally, intranasally, intraarterially, intravenously, intratumorally, or into an afferent lymph vessel, by parenteral administration, for example, by injection or infusion, although the administration route is not particularly limited.

(3) Process for Producing Cell Expressing CAR

A process for producing a cell expressing the CAR of the present disclosure includes a step of introducing the nucleic acid encoding a CAR described herein into a cell. The step is carried out ex vivo. For example, a cell can be transformed ex vivo with a virus vector or a non-virus vector carrying the nucleic acid of the present disclosure to produce a cell expressing the CAR of the present disclosure.

In the process of the present disclosure, a cell derived from a mammal, for example, a human cell, or a cell derived from a non-human mammal such as a monkey, a mouse, a rat, a pig, a horse, or a dog can be used.

In one embodiment, the mammal is a human.

The cell used in the process of the present disclosure is not particularly limited, and any cell can be used. For example, a cell collected, isolated, or purified from a body fluid, a tissue or an organ such as blood (peripheral blood, umbilical cord blood etc.) or bone marrow or a cell obtained by differentiating or reprogramming the aforementioned cell to produce an induce pluripotent stem cell (iPSC) can be used (see for example Themeli et al 2013). A peripheral blood mononuclear cell (PBMC), an immune cell [including for example a T cell, a dendritic cell, a B cell, a hematopoietic stem cell, a macrophage, a monocyte, a NK cell or a hematopoietic cell (a neutrophil, a basophil)], an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. For example, a NK cell or a T cell, a precursor cell of a T cell (a hematopoietic stem cell, a lymphocyte precursor cell etc.) or a cell population containing them can be used. Examples of the T cell include a CD8-positive T cell, a CD4-positive T cell, a regulatory T cell, a cytotoxic T cell, and a tumor infiltrating lymphocyte. The cell population containing a T cell and a precursor cell of a T cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, the nucleic acid can be introduced into a cell collected from the living body itself or a conspecific living body thereof.

The nucleic acid encoding the CAR of the present disclosure can be inserted into a vector, and the vector can be introduced into a cell. For example, a virus vector such as a retrovirus vector (including an oncoretrovirus vector, a lentivirus vector, and a pseudotyped vector), an adenovirus vector, an adeno-associated virus (AAV) vector, a simian virus vector, a vaccinia virus vector or a sendai virus vector, an Epstein-Barr virus (EBV) vector, and a HSV vector can be used. For example, a virus vector lacking the replicating ability so as not to self-replicate in an infected cell can be used.

In addition, a non-virus vector can also be used in the present disclosure in combination with a liposome or a condensing agent such as a cationic lipid as described in WO 96/10038, WO 97/18185, WO 97/25329, WO 97/30170 and WO 97/31934 (which are incorporated herein by reference). The nucleic acid of the present disclosure can be also introduced into a cell by calcium phosphate transduction, DEAE-dextran, electroporation, or particle bombardment.

For example, when a retrovirus vector is used, the process of the present disclosure can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056), and Psi-Crip [Proceedings of the National Academy of Sciences of the United States of America, vol. 85, pp. 6460-6464 (1988)]. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

One aspect is a method of making a cell herein disclosed, comprising transfecting or transducing a cell with a nucleic acid or a vector described herein.

Another aspect is a method of making a cell herein disclosed, comprising:
a) isolating immune cells from a mammal;
b) transfecting or transducing the isolated immune cells, optionally isolated T cells, with a nucleic acid encoding a CAR herein disclosed or a vector comprising said nucleic acid; and
c) optionally isolating and/or expanding CAR-expressing cells, optionally CAR-expressing T cells.

In one embodiment, the isolated immune cells are isolated T cells.

In an embodiment, the isolated cells are CD3+, and optionally stimulated with an anti-CD3 antibody, optionally in a soluble or membrane-bound form, e.g. OKT3 or mOKT3, and/or APC prior to transduction or transfection. In one embodiment, the APC are artificial APC (aAPC). In another embodiment, the aAPC express a membranous form of anti-CD3 monoclonal antibody.

In one embodiment, the transfecting or transducing step is repeated. For example, the transfecting or transducing step can be carried out twice, or three times, or four times or until for example adequate level of expression is achieved. For example, the transfecting or transducing step is can be carried out five times.

In one embodiment, the cells are transfected or transduced on more than one consecutive day. For example, the cells are transfected or transduced for two consecutive days, three consecutive days or four consecutive days.

In one embodiment, the CAR-transduced cells are stimulated with irradiated cells expressing a predetermined antigen. For example, the CAR-transduced T cells are stimulated with irradiated cells at an effector to target ratio of 100:1, 75:1, 50:1, 25:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:25, 1:50 or 1:100.

(4) Cell Expressing CAR and Uses Thereof

The cell expressing the CAR of the present disclosure is a cell in which the nucleic acid encoding a CAR described herein is introduced and expressed by the production process described herein.

The cell of the present disclosure binds to a specific antigen via the CAR, thereby a signal is transmitted into the cell, and as a result, the cell is activated. The activation of the cell expressing the CAR is varied depending on the type of host cell and the intracellular domains of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

Figure 12:
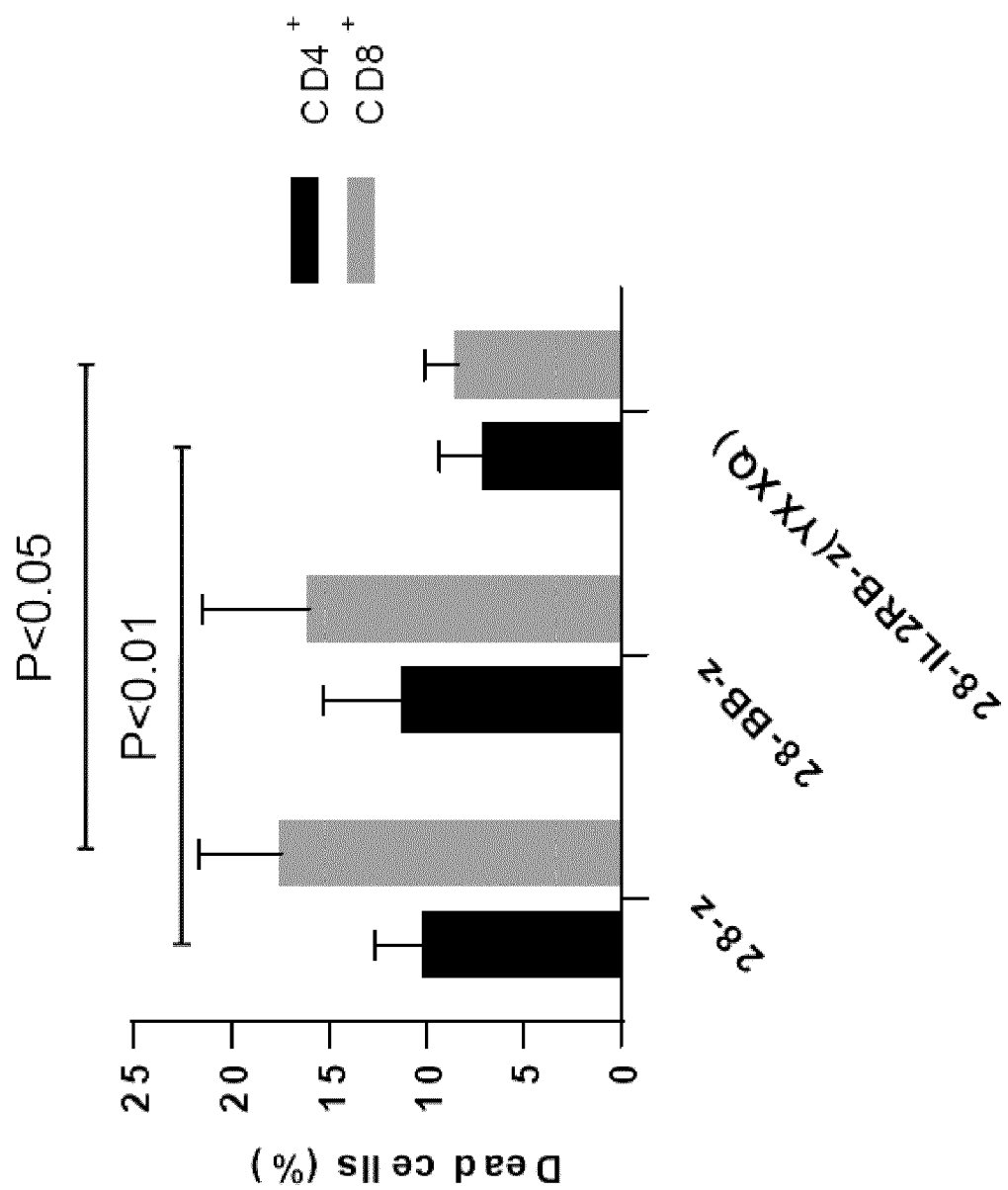
FIG. 12 is a graph showing viability of the CAR-transduced T cells.
Figure 14:
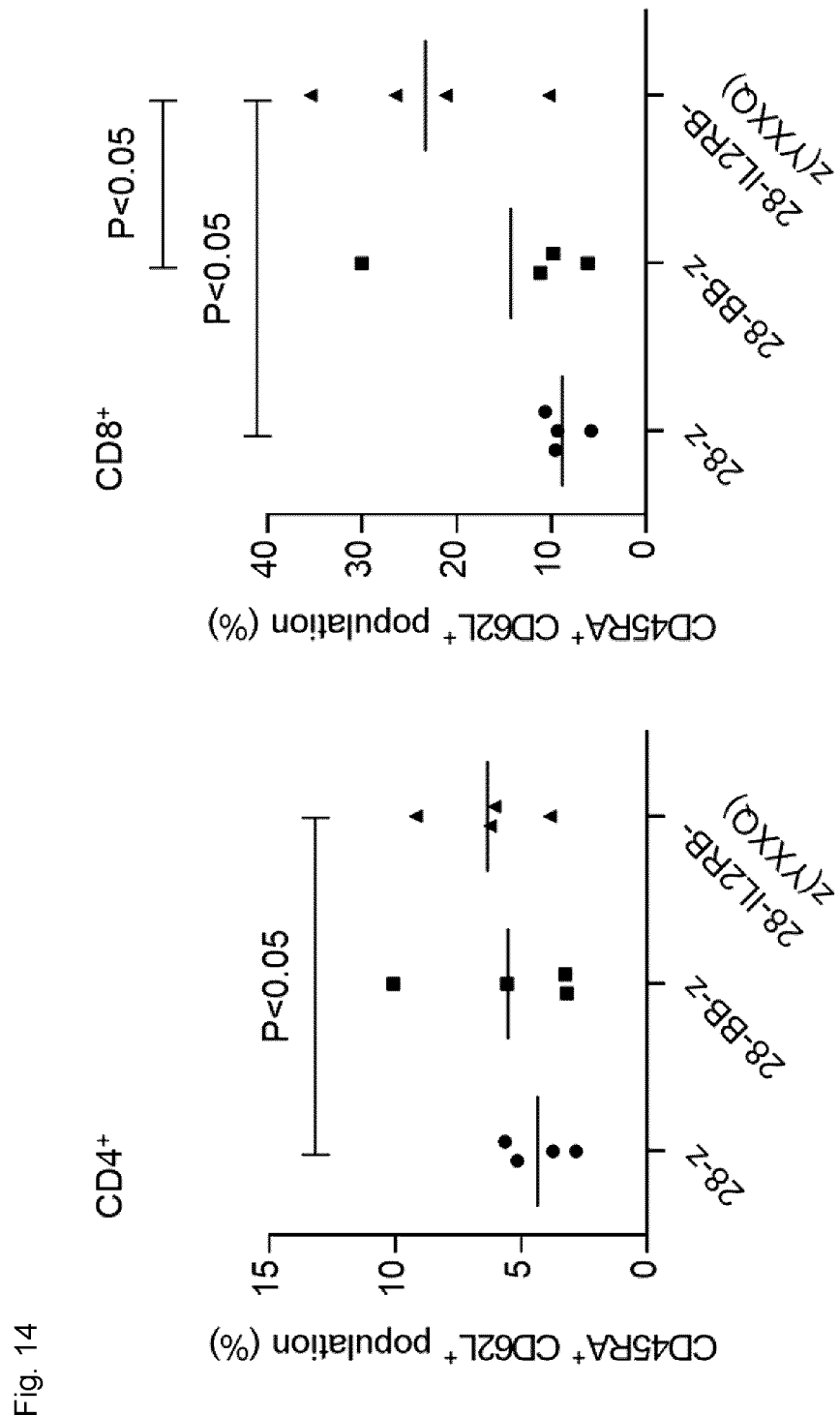
FIG. 14 is a series of graphs showing the frequency of CAR-transduced T cells with a stem cell-like memory T cell marker phenotype (CD45RA+ CD62L+ CD95+).

It is demonstrated herein that the 28-IL2RB-z (YXXQ) CAR-engineered T cells have superior proliferation through higher cell division rate and reduced apoptosis compared to T cells comprising first (28-z) and second (28-BB-z) generation CARS (see FIG. 12). In addition, the 28-IL2RB-z (YXXQ) CAR-engineered T cells also maintain stem cell-like memory phenotypes after repeated antigen stimulation (FIG. 14).

Accordingly, the cell expressing the CAR may be used as a therapeutic agent for a disease. As shown in Example 4 as well as in FIG. 18-20, mice injected with leukemic cells and treated with 28-IL2RB-z (YXXQ) anti-CD19 CAR showed decreased tumor activity as well as increased overall survival compared to untreated mice and mice treated with previous generation CARs.

In one aspect, there is provided a use of a CAR, a nucleic acid, a vector, a cell or a composition described herein for treating a disease.

Another aspect is a method of treating or preventing a disease in a mammal, the method comprising administering to the mammal in need thereof an effective amount of cells or a composition herein disclosed.

A further aspect is a method of providing an anti-tumor immunity in a mammal, the method comprising administering to the mammal in need thereof an effective amount of a cell or a composition herein disclosed.

The therapeutic agent comprises the cell expressing the CAR as an active ingredient, and may further comprise a suitable excipient. Examples of the excipient include the aforementioned pharmaceutically acceptable excipients for the composition comprising the nucleic acid of the present disclosure as an active ingredient, various cell culture media, and isotonic sodium chloride.

The disease against which the cell expressing the CAR is administered is not particularly limited as long as the disease shows sensitivity to the cell. In one embodiment, the disease is a cancer.

For example, the cancer is a blood cancer or a solid tumor. For example, the blood cancer is a leukemia, lymphoma or myeloma. For example, the solid tumor is breast cancer, ovarian cancer, glioblastoma, osteosarcoma, or medulloblastoma.

In an embodiment, the disease is an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis.

The cell expressing the CAR of the present disclosure that binds to an antigen possessed by a cell that is desired to be decreased or eliminated for treatment of the aforementioned diseases, that is, a tumor antigen, a viral antigen, a bacterial antigen or the like is administered for treatment of these diseases.

Accordingly, an aspect includes a method of decreasing in a subject the number of cells expressing a predetermined antigen, the method comprising administering to the subject in need thereof an effective amount of cells expressing a CAR as described herein, wherein the CAR specifically binds to the predetermined antigen.

The cell of the present disclosure can also be utilized for prevention of an infectious disease after bone marrow transplantation or exposure to radiation, donor lymphocyte transfusion for the purpose of remission of recurrent leukemia, and the like.

The therapeutic agent comprising the cell expressing the CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In one embodiment, the subject is suspected of having or has cancer. In one embodiment, the subject is suspected of having or has an inflammatory disease.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

The present disclosure will be further explained in more detail by way of Examples, which the present disclosure is not limited to.

Example 1

Anti-CD19 Chimeric Antigen Receptor (CAR) Constructs

A FMC63-derived single-chain variable fragment (scFv) (Nicholson et al., 1997) has been linked to CD28 and CD3ζ chain (28-z, $2^{nd}$ generation), CD28, 4-1BB and CD3ζ chain (28-BB-z, $3^{rd}$ generation), or CD28, cytoplasmic domain of IL-2 receptor β chain with internal deletion, and CD3ζ chain with an exogenous YXXQ motif (SEQ ID NO: 13) has been introduced for STAT3 binding (28-IL2RB-z (YXXQ)), as shown in FIG. 1. The YXXQ (SEQ ID NO: 13) motif was generated by substituting Leu-His-Met residue at position 156-158 encoded by CD3ζ chain for Tyr-Arg-His. FMC63 is an IgG2a mouse monoclonal antibody belonging to the CD19 cluster. Oncostatin M was used as a signal peptide. Gibson Assembly Method was used for site-directed mutagenesis. The following primers were used: ACGCCTATCGCCATCAGGCCCTGC (SEQ ID NO: 26), and CTGATGGCGATAGGCGTCGTAGGTGT (SEQ ID NO: 27).

Transduction Efficiency of Primary T Cells with Anti-CD19 CAR Constructs

Figure 2:
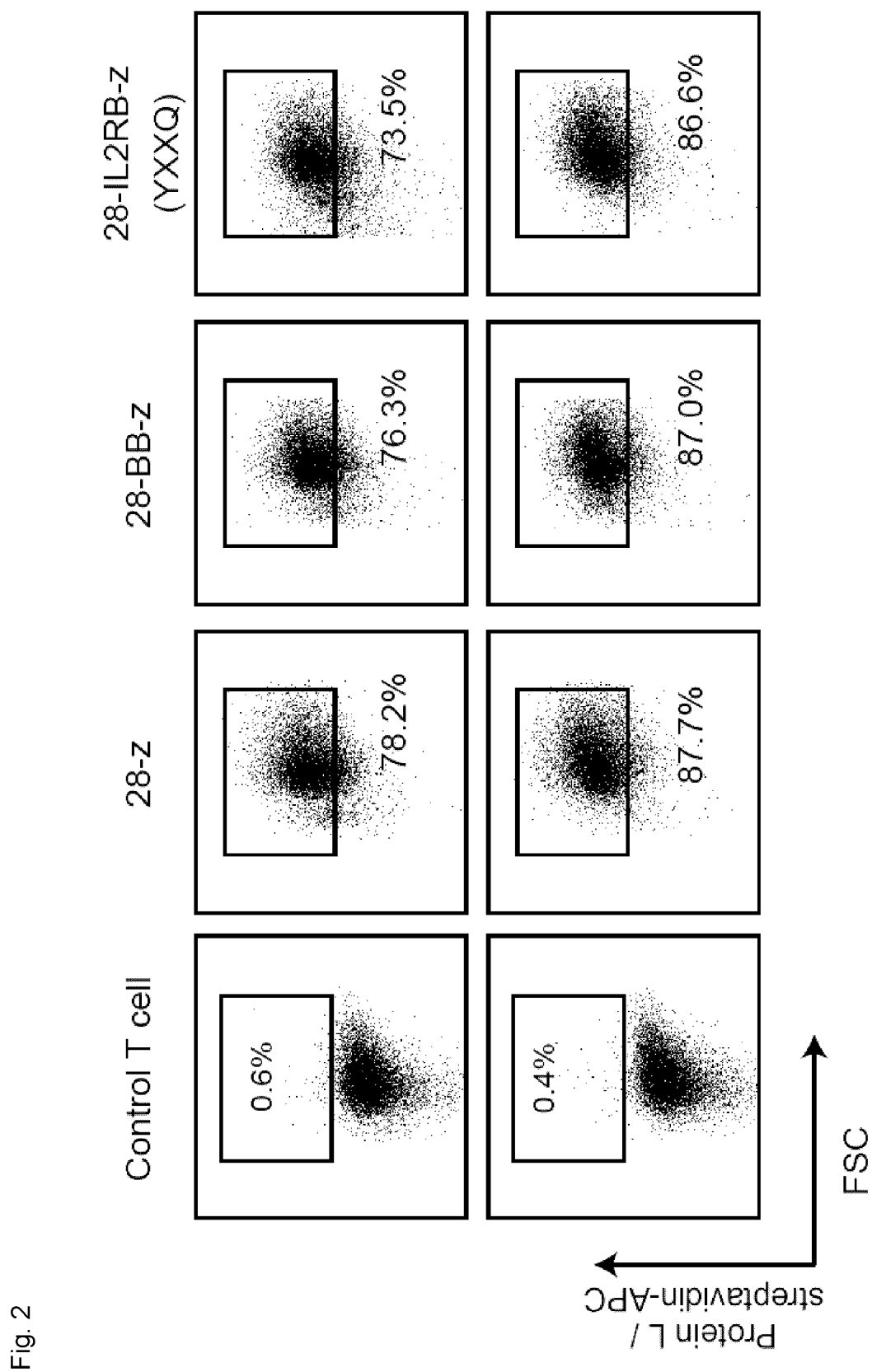
FIG. 2 is a series of plots of a flow cytometry analysis showing transduction efficiency of primary T cells with anti-CD19 CAR constructs.

To determine the transduction efficiency of primary T cells with anti-CD19 CAR constructs, peripheral blood CD3+ T cells were stimulated with artificial antigen presenting cells expressing a membranous form of anti-CD3 mAb (clone OKT3), CD80, and CD83 (mOKT3/aAPC) (Butler et al., 2012), and subsequently transduced with individual CAR constructs suing retrovirus. The transduction was repeated for three consecutive days. Seven days following initial stimulation with mOKT3/aAPC, the CAR transduced T cells were stained with biotin-labeled protein L followed by streptavidin-APC. The stained T cells were analyzed by flow cytometry, as shown in FIG. 2. Transduction efficiency was comparable in the T cells transduced with various CAR constructs. Representative data of four independent experiments are shown.

Anti-CD19-CAR Surface Expression

Anti-CD19-CAR surface expression was compared by measuring mean fluorescence intensity (MFI) of CAR constructs expressed in primary T cells (n=4) (FIG. 3). The CAR surface expression was slightly lower in the 28-BB-z and the 28-IL2RB-z (YXXQ) CAR T cells compared with the 28-z CAR T cells. Statistical significance was evaluated with the paired t test. Error bars indicate S.D.

Figure 4:
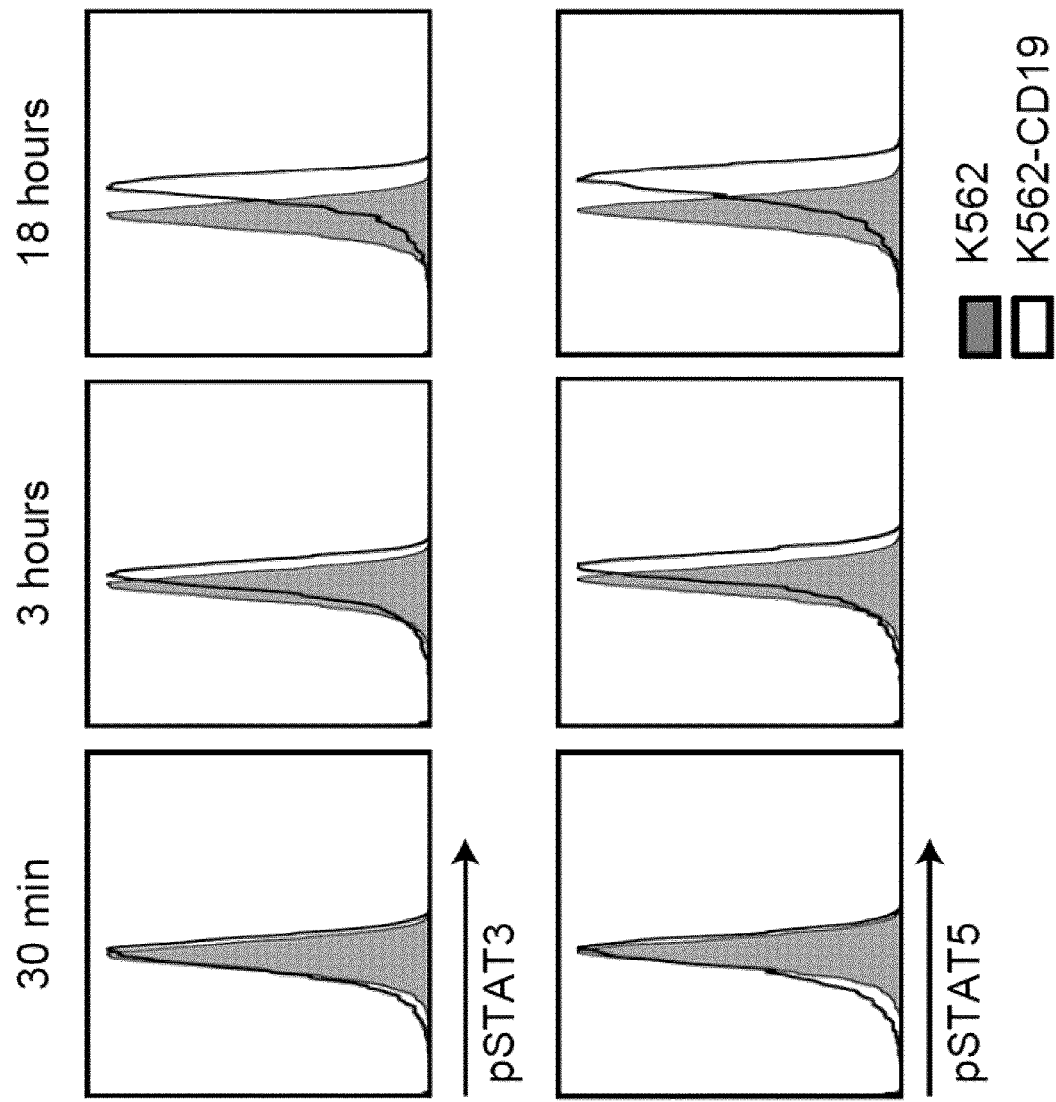
FIG. 4 is a series of graphs showing phosphorylation of STAT3 and STAT5 in the 28-IL2RB-z (YXXQ) anti-CD19 CAR-transduced T cells.

Phosphorylation of STAT3 and STAT5 in the 28-IL2RB-z (YXXQ) CAR-Transduced T Cells The 28-IL2RB-z (YXXQ) CAR-transduced T cells were rested in cytokine-free media for one day, and stimulated with K562-CD19 cells at an effector to target (E:T) ratio of 2:1. Phosphorylated STAT3 and STAT5 CD8+ T cells were fixed/permeabilized, stained with specific mAbs, and analyzed by intracellular flow cytometry analysis, as shown in FIG. 4. The 28-IL2RB-z (YXXQ) CAR-engineered T cells showed gradual increase in phosphorylation of both STAT3 and STAT5. Representative data of three experiments are shown.

Comparison of JAK-STAT Pathway Activity in CAR-Transduced T Cells

Figure 5:
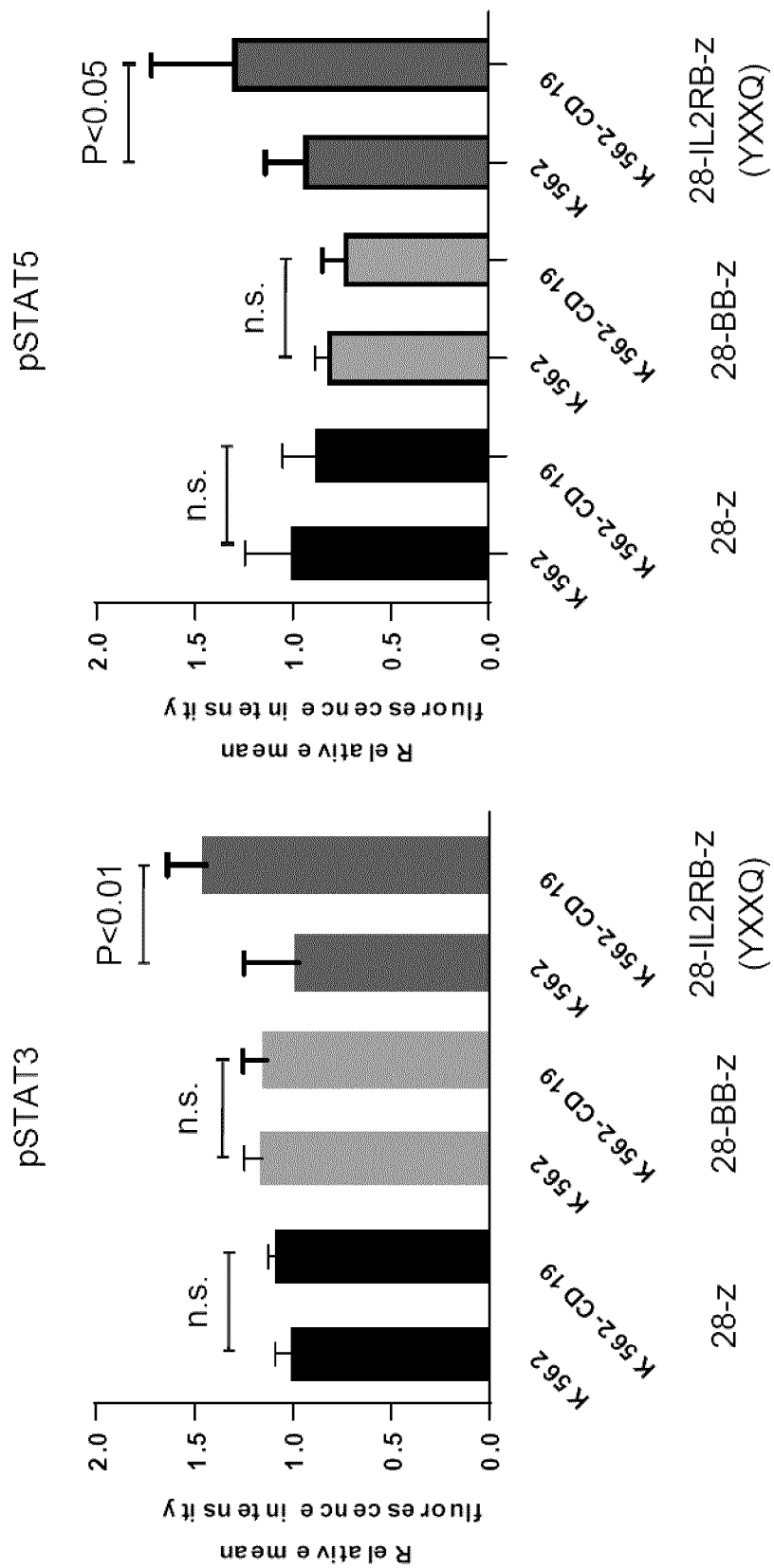
FIG. 5 is a graphical comparison of JAK-STAT pathway activity in CAR-transduced T cells.

CAR-transduced T cells were stimulated with K562 cells or K562 cells stably expressing CD19 (K562-CD19) under the same conditions as in FIG. 4, and phosphorylated STAT3 and STAT5 expression was measured 18 hours following stimulation. Relative mean fluorescence intensity (MFI) was calculated by dividing each MFI by the average MFI value of the 28-z CAR-transduced T cells cocultured with K562 cells (n=4). As shown in FIG. 5, the 28-IL2RB-z (YXXQ) CAR+ T cells showed significantly higher phosphorylation of STAT3 ($P<0.01$) and STAT5 ($P<0.05$; paired t test) when they were cocultured with K562-CD19 cells, indicating that the CAR induced CD19-specific JAK-STAT pathway activation.

Example 2

Protocol for Anti-CD19 CAR Construct T Cell Transduction and Expansion

Figure 6:
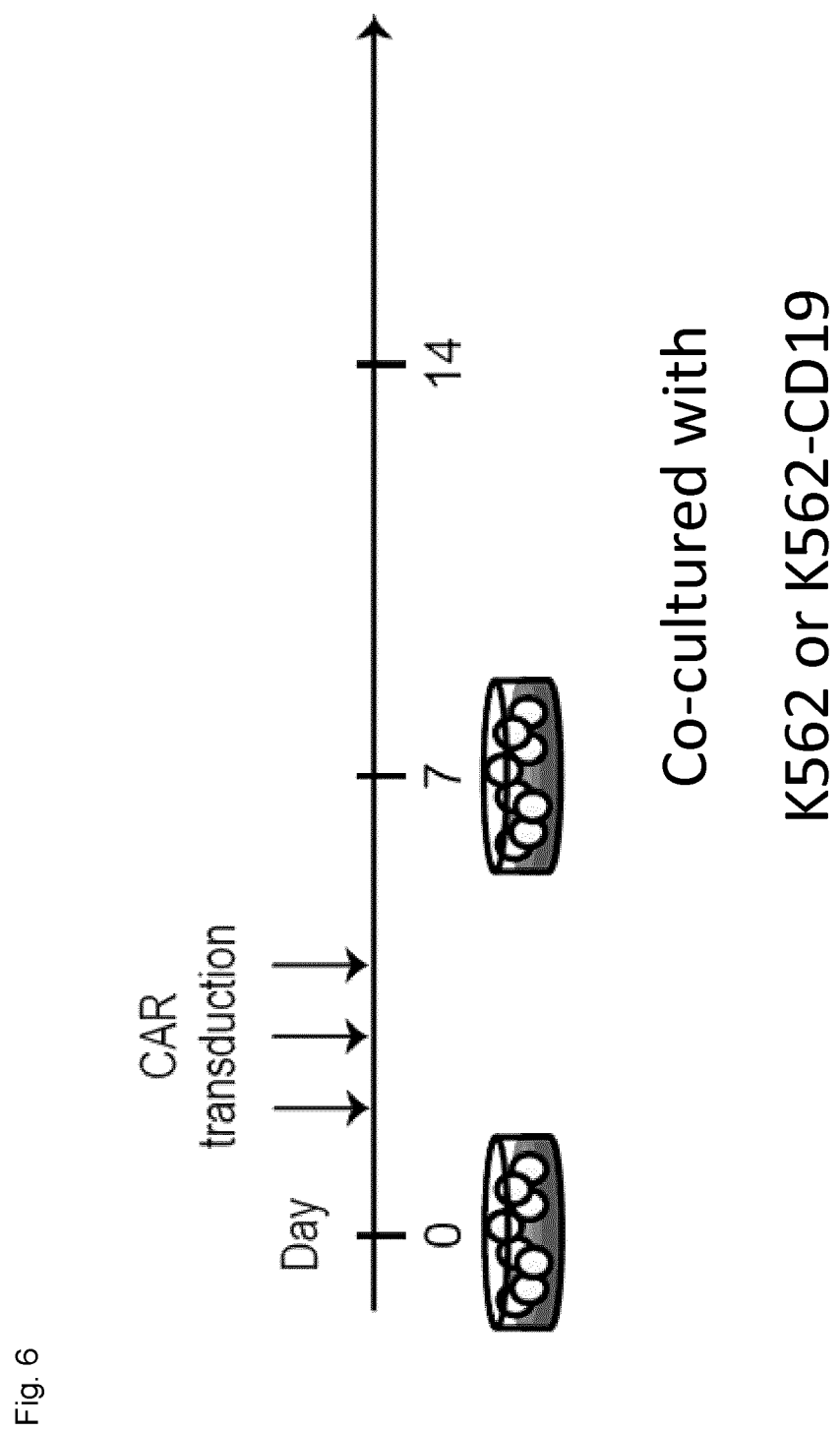
FIG. 6 is a schematic illustrating a protocol for anti-CD19 CAR construct T cell transduction and expansion.

Peripheral CD3+ T cells were stimulated with mOKT3/aAPC, and retrovirally transduced with individual CD19 CARs for three consecutive days. The CAR-transduced T cells were stimulated with irradiated K562-CD19 cells or K562 cells in the presence of IL-2 100 IU/mL and IL-15 10 ng/mL at an E:T ratio of 2:1 in a weekly manner where indicated (see FIG. 6). Variations of E:T ratio and duration of transduction can be envisaged. For example, the CD3+ T cells stimulated with mOKT3/aAPC can be transduced for three consecutive days at an E:T ratio of 10:1.

Expansion of CAR-Transduced T Cells Following Transduction

Figure 7:
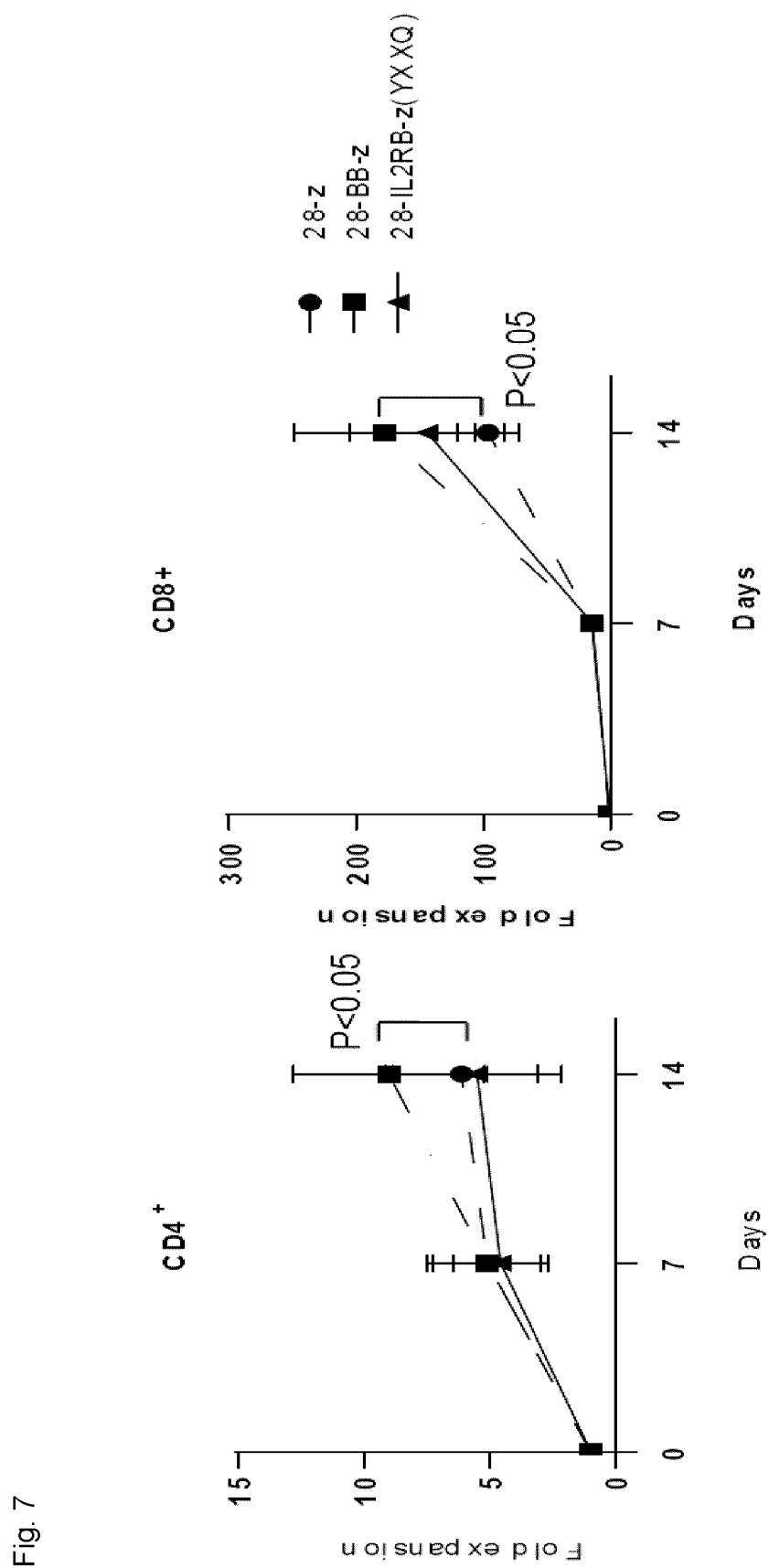
FIG. 7 is a series of graphs showing expansion of CAR-transduced T cells following transduction.

Fold expansion of CAR-transduced T cells is shown (n=4) in FIG. 7. Greater than 100-fold expansion of CD8$^+$ T cells was obtained in 2 weeks in all the CAR-transduced T cells. The 28-BB-z CAR-transduced T cells showed significantly superior proliferation compared to the 28-z CAR-transduced T cells following transduction (P<0.05 by the paired t test), while there was no difference between the 28-z and 28-IL2RB-z (YXXQ) CAR-transduced T cells.

Figure 8:
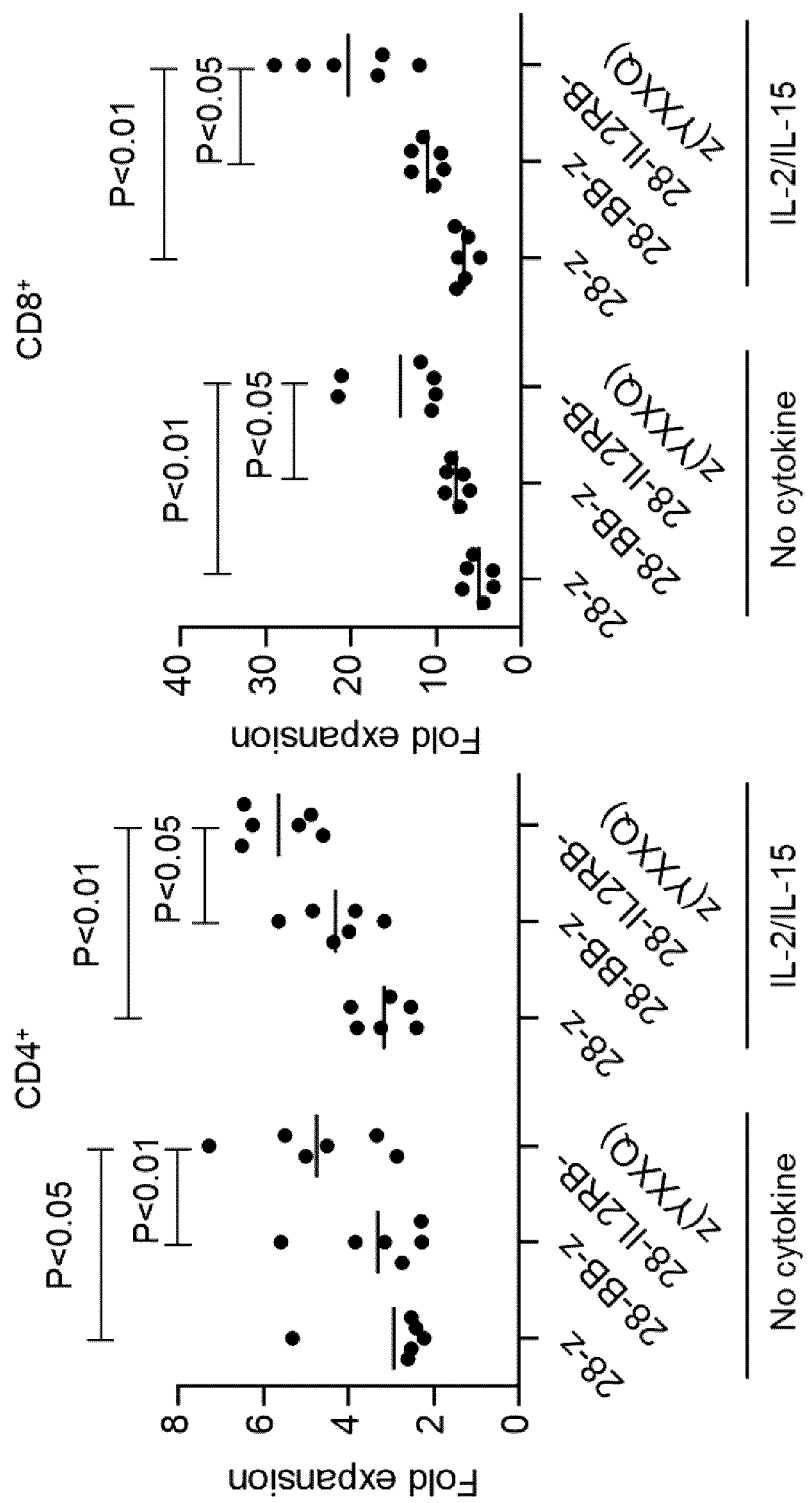
FIG. 8 is a series of graphs showing expansion of CAR-transduced T cells following CD19-specific stimulation with K562-CD19 cells.

Expansion of CAR-Transduced T Cells Following CD19-Specific Stimulation with K562-CD19 Cells The CAR-transduced T cells were stimulated in a CD19-specific manner using irradiated K562-CD19 cells. The T cells transduced with the 28-IL2RB-z (YXXQ) CAR showed superior proliferation in both CD4$^+$ and CD8$^+$ T cells regardless of cytokine supplementation. Fold expansion of CAR$^+$ T cells is shown in FIG. 8 (n=4; statistical significance was evaluated with the paired t test).

Expansion of CAR$^+$ T Cells Following Co-Culture with K562 Cells

Figure 9:
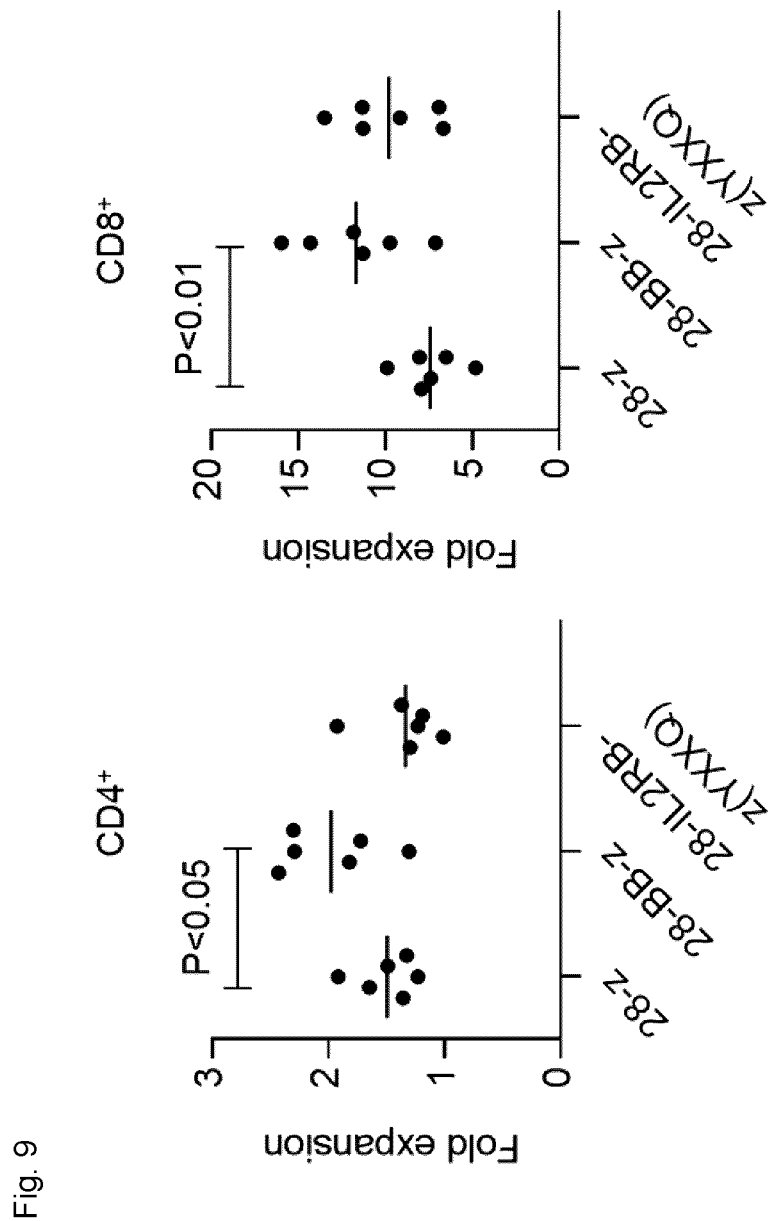
FIG. 9 is a series of graphs showing expansion of CAR-transduced T cells following co-culture with K562 cells (control).

The CAR-transduced T cells were stimulated with irradiated K562 cells (control). Fold expansion of CAR-transduced T cells is shown (n=4) in FIG. 9. As previously shown, the T cells transduced with the 28-BB-z promoted antigen-independent proliferation compared with the 28-z CAR-transduced T cells (Milone et al., 2009) (P<0.05 for CD8$^+$ T cells by the paired t test). In contrast, the 28-IL2RB-z (YXXQ) CAR$^+$ T cells did not confer proliferative advantage over the 28-z CAR T cells in the absence of antigen-specific CD19 stimulation.

Figure 10:
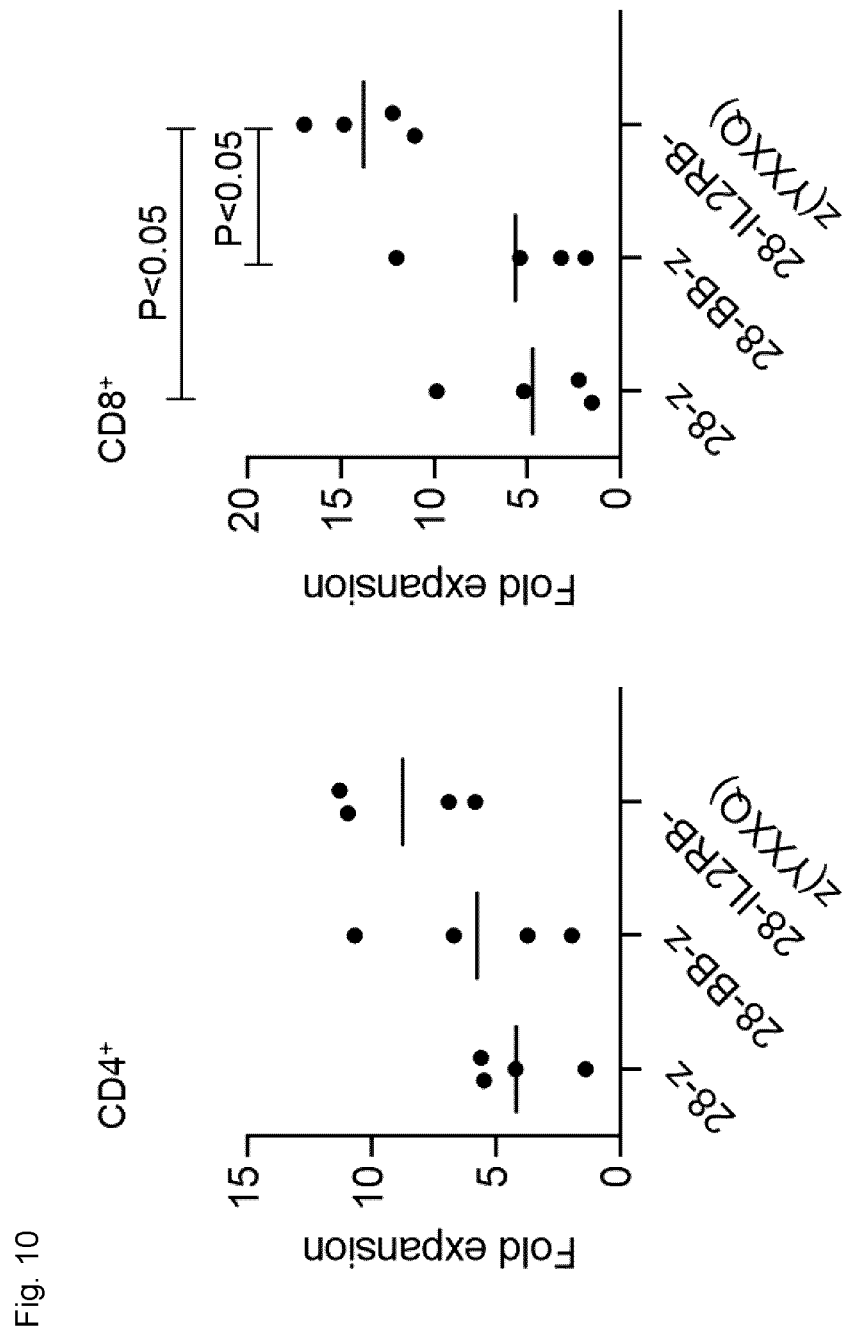
FIG. 10 is a series of graphs showing expansion of the CAR-transduced T cells after antigen-specific restimulation with K562-CD19 cells.

Expansion of the CAR$^+$ T Cells after Antigen-Specific Restimulation with K562-CD19 Cells The CAR-transduced T cells were weekly stimulated twice with irradiated K562-CD19 cells, as shown in FIG. 10. Fold expansion of the CAR$^+$ T cells is shown (n=4). The 28-IL2RB-z (YXXQ) CAR-engineered T cells showed improved proliferation compared to the other CAR-transduced T cells (P<0.05 for CD8$^+$ T cells; paired t test).

Cell Division Rate in CAR-Transduced T Cells

CAR-engineered T cells were labeled with carboxyfluorescein succinimidyl ester (CFSE), and stimulated with K562-CD19 cells at a ratio of 2:1. The average MFI of CFSE in the CAR-transduced CD4$^+$ or CD8$^+$ T cells 3 days following stimulation relative to that of the 28-z CAR-transduced T cells is shown in FIG. 11 (n=4). The intensity of CFSE in the 28-z CAR-transduced T cells were set to one in each donor. Error bars indicate S.D. Statistical significance was evaluated with the paired t test. The T cells transduced with the 28-IL2RB-z (YXXQ) CAR showed significantly enhanced cell division.

Example 3

Viability the CAR-Transduced T Cells

CAR-transduced T cells were stimulated with K562-CD19 cells at a ratio of 2:1. The frequency of dead cells was evaluated by flow cytometry 3 days following stimulation (n=4) (FIG. 12). Error bars depict S.D. The T cells transduced with the 28-IL2RB-z (YXXQ) CAR construct showed decreased apoptosis upon antigen stimulation. Significance of difference was evaluated by the paired t test. The data presented in FIGS. 11 and 12 demonstrate that the proliferative advantage of the 28-IL2RB-z (YXXQ) CAR$^+$ T cells upon CD19 stimulation resulted from both enhanced cell division and decreased apoptosis.

Surface Phenotype of CAR-Transduced T Cells

Figure 13:
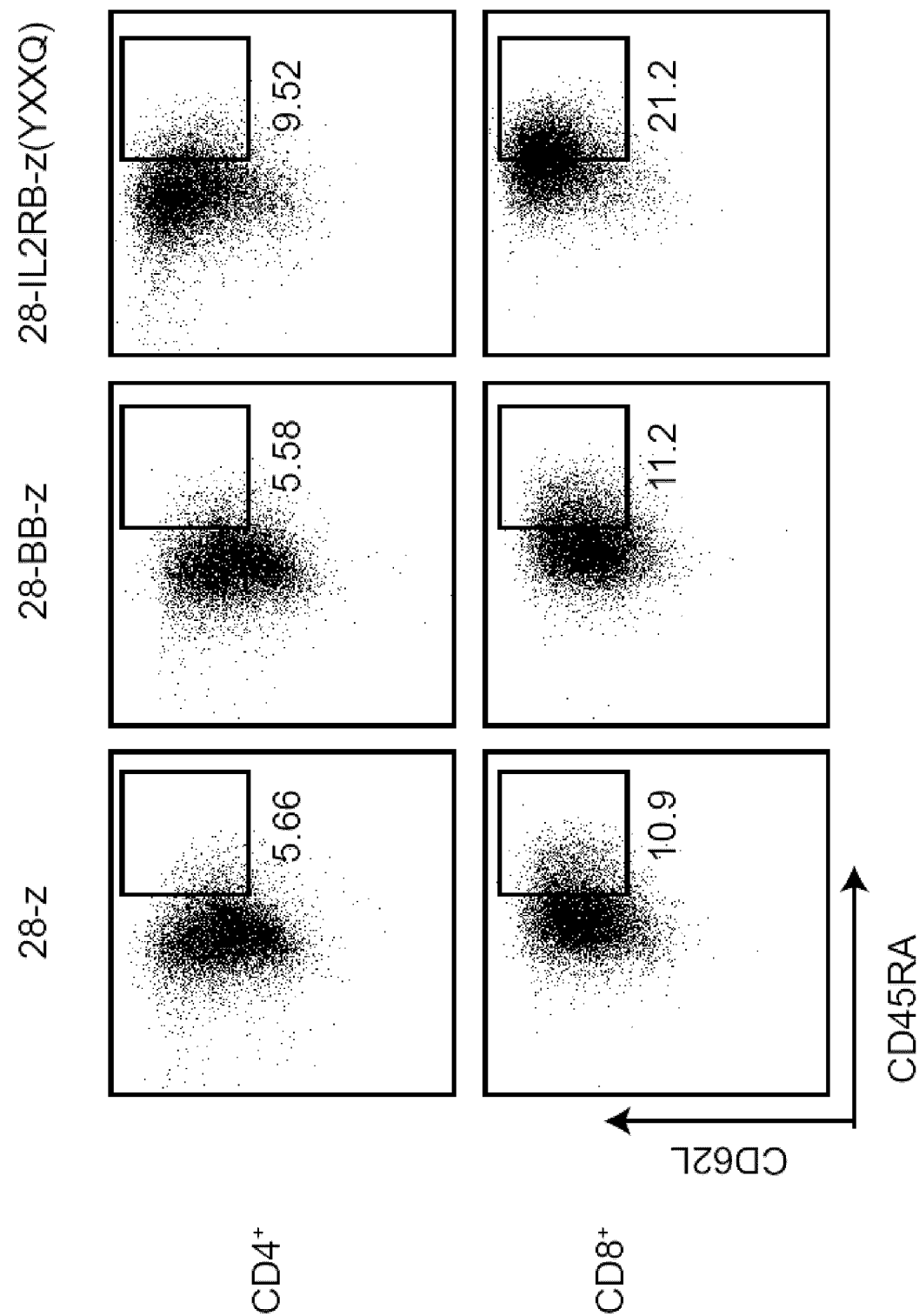
FIG. 13 is a series of plots of flow cytometry analysis showing surface phenotype and CD4+ and CD8+ expression levels of CAR-transduced T cells.

CAR-transduced T cells were stimulated with K562-CD19 at a ratio of 2:1. Surface CD45RA and CD62L on CD4$^+$ and CD8$^+$ T cells were stained by specific mAbs and subjected to flow cytometry analysis 7 days following stimulation (FIG. 13). Representative data of 4 independent experiments is shown. The T cells transduced with the 28-IL2RB-z (YXXQ) CAR maintained the CD45RA$^+$ CD62L$^+$ T-cell subset compared to the 28-z or 28-BB-z CAR$^+$ T cells.

The Frequency of CAR T Cells with a Stem Cell-Like Memory T Cell Marker Phenotype (CD45RA$^+$ CD62L$^+$ CD95$^+$)

CAR-transduced T cells were stimulated with K562-CD19 at a ratio of 2:1. CD45RA, CD62L, and CD95 surface expression was analyzed 7 days following stimulation (n=4) (FIG. 14). The 28-IL2RB-z (YXXQ) CAR-transduced T cells possessed significantly higher frequency of a CD45RA$^+$ CD62L$^+$ CD95$^+$ stem cell-like memory T cell subset. Statistical significance was evaluated with the paired t test.

Comparison of CD62L Expression in CAR-Transduced T Cells

CD62L expression in CAR-transduced T cells was analyzed as described for FIGS. 13 and 14. Relative MFI of CD62L expression in the CAR-transduced CD4$^+$ and CD8$^+$ T cells was calculated by dividing each MFI by the average MFI value of the 28-z CAR-transduced T cells (n=4). The 28-IL2RB-z (YXXQ) CAR-transduced T cells displayed significantly higher expression level of CD62L compared to the other CAR$^+$ T cells (P<0.05 by the paired t test).

IL-2 Secretion by CAR-Transduced T Cells

Figure 15:
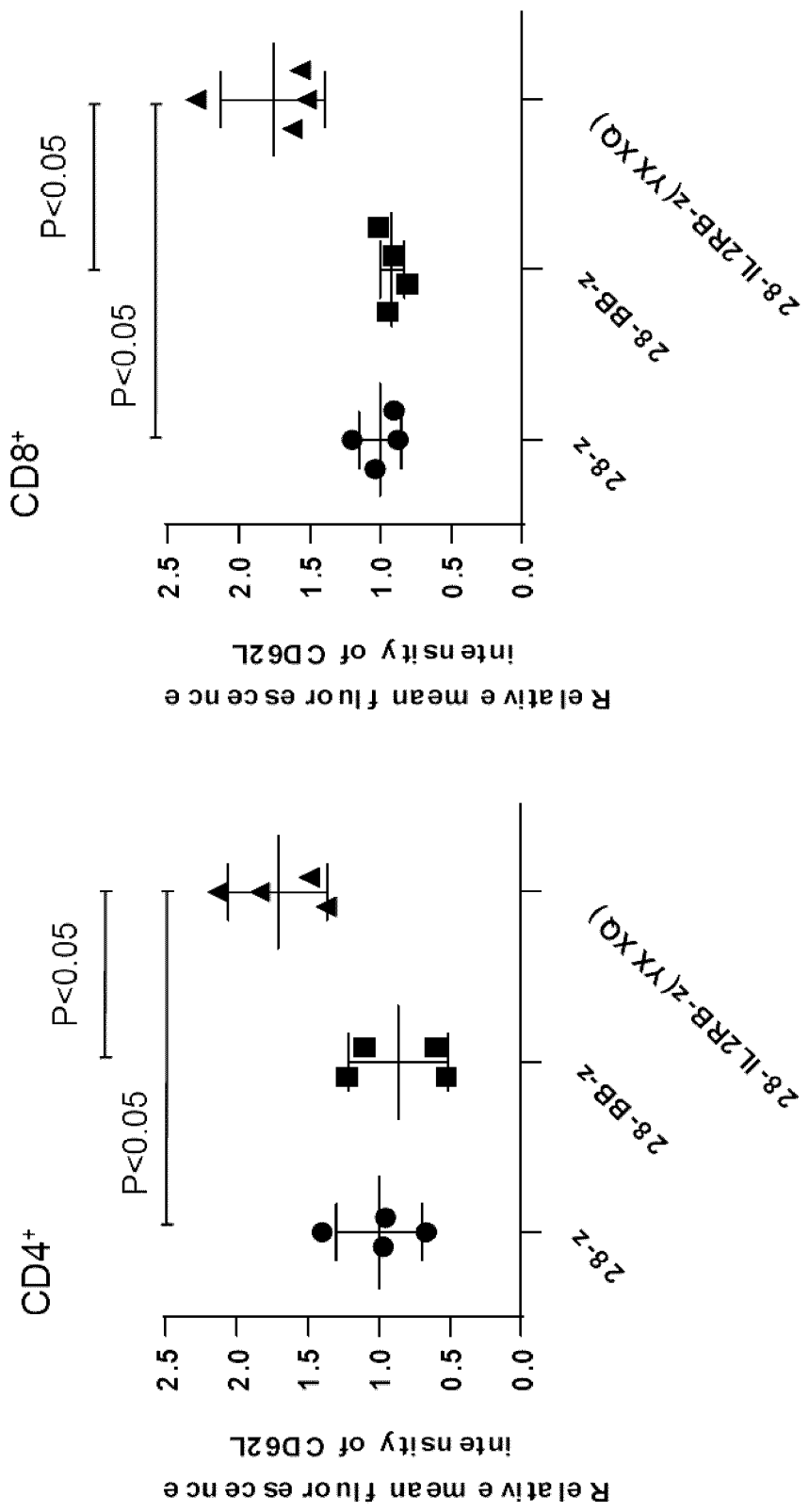
FIG. 15 is a series of graphs comparing CD62L expression in CAR-transduced T cells.
Figure 16:
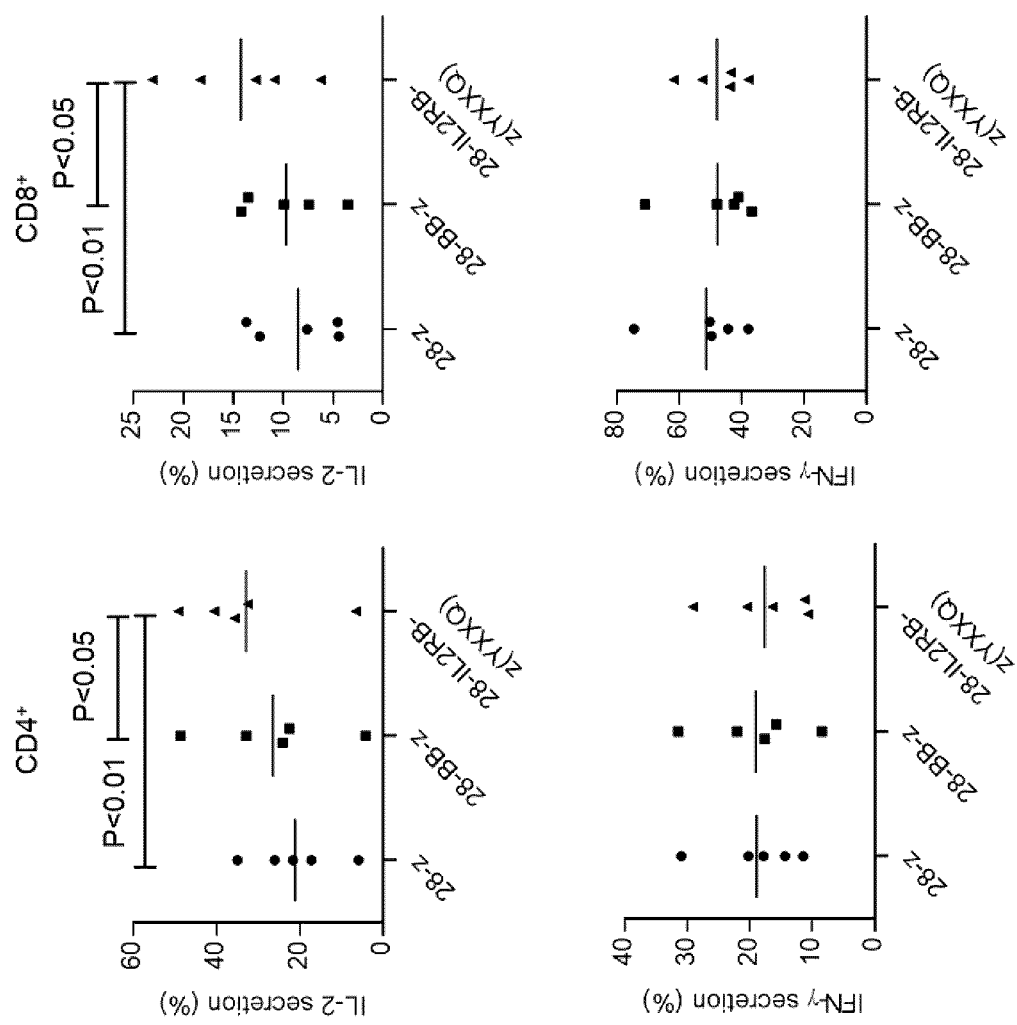
FIG. 16 is a series of graphs showing IL-2 and IFN-γ secretion by CAR-transduced T cells.
Figure 17:
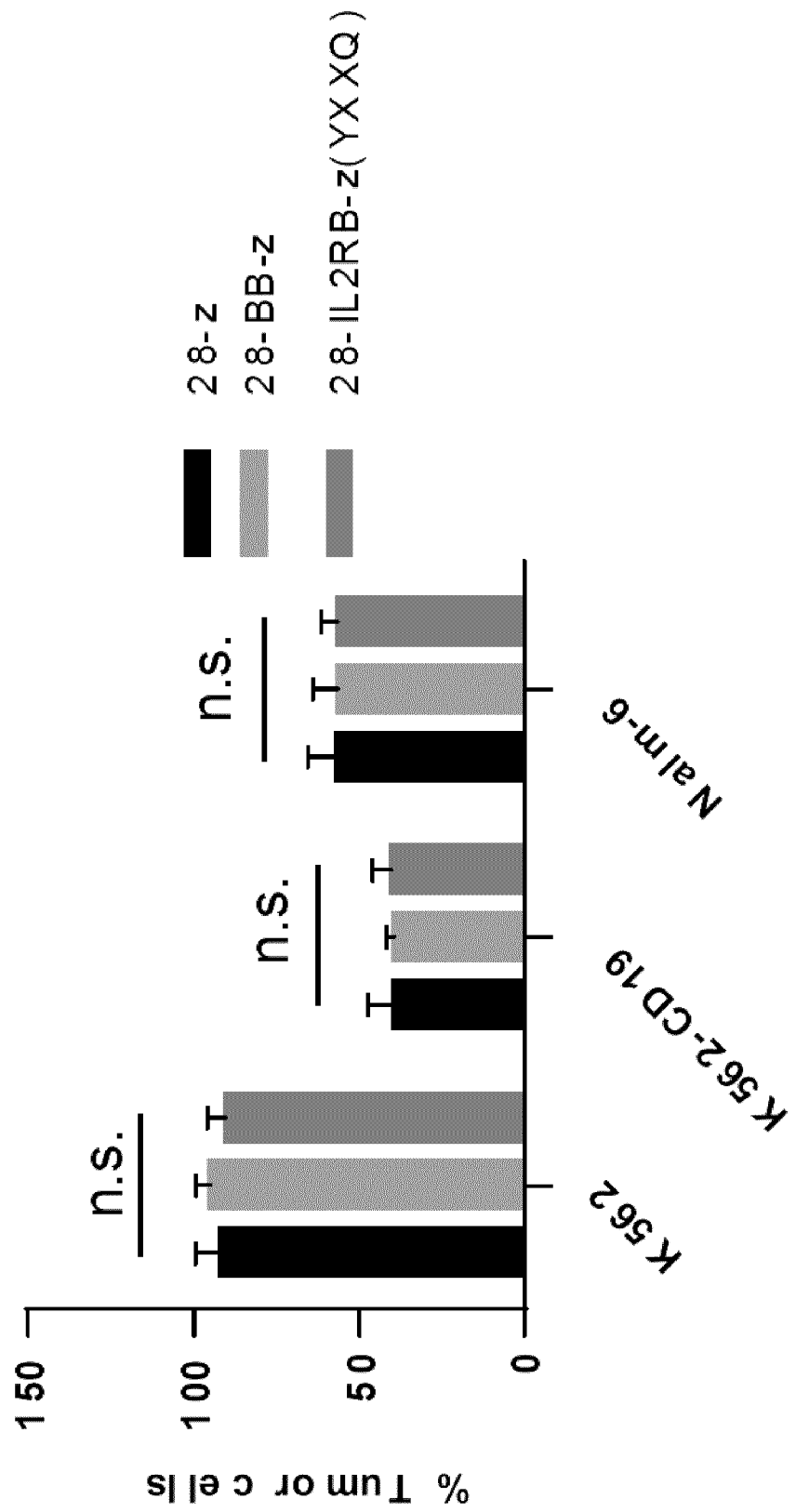
FIG. 17 is a graph showing in vitro target cell lysis by CAR-transduced T cells.

CAR-transduced T cells were stimulated with K562-CD19 at a ratio of 1:1. One week following stimulation, the T cells were restimulated with mOKT3/aAPC, and cytokine secretion was measured with intracellular flow cytometry following staining with specific mAbs. The 28-IL2RB-z (YXXQ) CAR$^+$ T cells secreted more IL-2 compared to 28-z and 28-BB-z CAR-transduced T cells. The significance was evaluated by the paired t test. These results are consistent with the data shown in FIG. 15; the 28-IL2RB-z (YXXQ) CAR$^+$ T cells preferentially maintained a CD45RA$^+$ CD62L$^+$ CD95$^+$ stem cell-like memory T cell subset compared to the other CAR T cells.

In Vitro Target Cell Lysis by CAR-Transduced T Cells

CAR-transduced T cells were cocultured with irradiated target cells (K562-CD19 and CD19$^+$ Nalm-6 cells) labeled with carboxyfluorescein succinimidyl ester (CFSE) at an E:T ratio of 3:1 for 6 hours. Percentage of residual CFSE-positive live cells in the culture was determined by flow cytometry analysis (n=3). Parental K562 cells were used as a control. Error bars depict S.D. Statistical significance was evaluated with repeated measures ANOVA. The 28-IL2RB-z (YXXQ) CAR-transduced T cells demonstrated lytic activity against CD19$^+$ cells comparable to the other CAR-transduced T cells.

Example 4

Vector Construction

Figure 21:
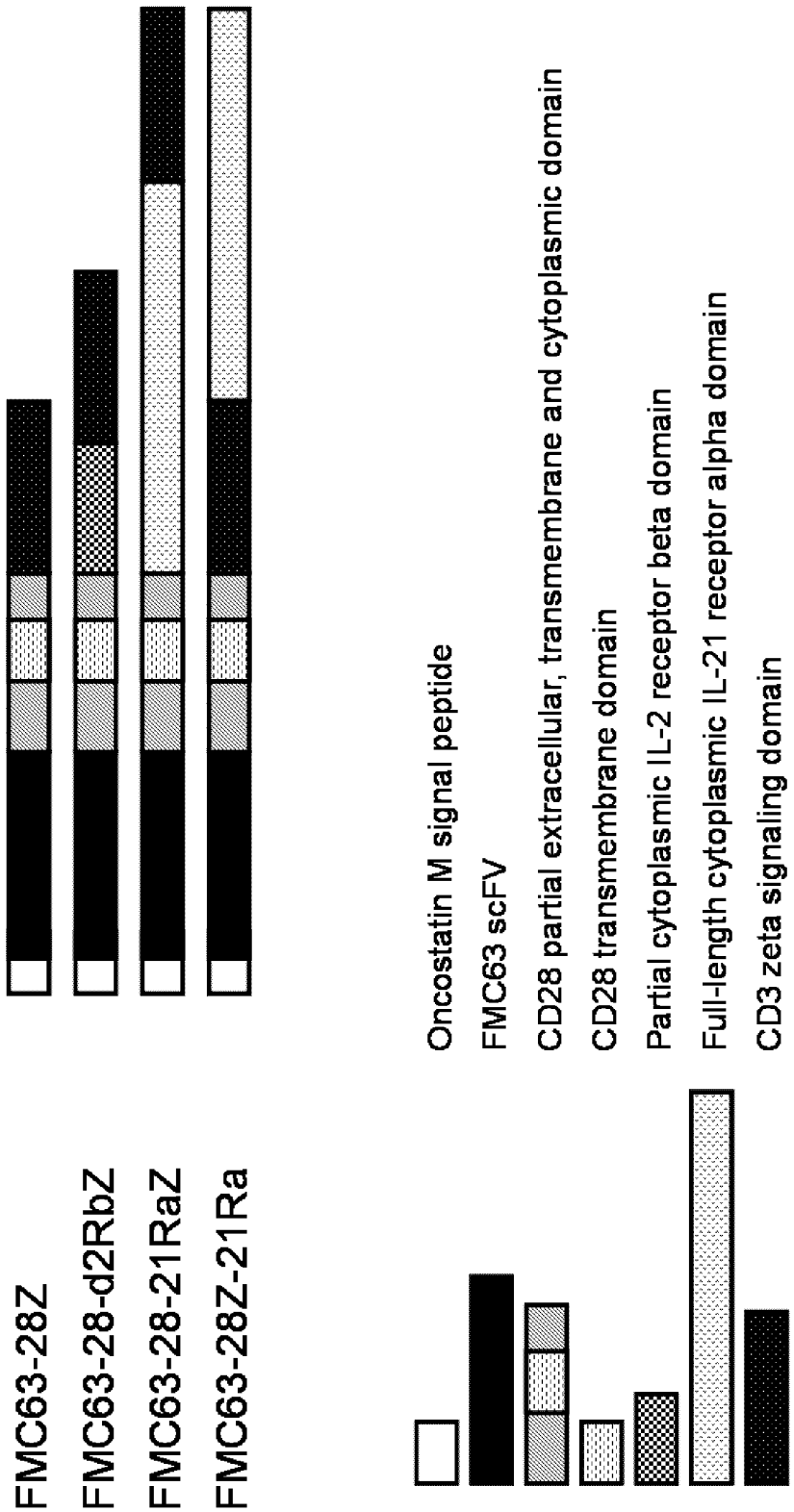
FIG. 21 shows the structure of CARs NFMC63-28Z, NFMC63-28-d2RbZ, NFMC63-28-21RaZ or NFMC63-28Z-21Ra used in the Examples.

NFMC63-28Z CAR, also referred to as 28-z CAR, is anti-CD19 chimeric antigen receptor created by replacing the signal sequence of FMC63-28Z CAR, which is originally constructed by Kochenderfer et al. (J Immunother. 2009 September; 32(7):689-702), with the Oncostatin M signal sequence (NCBI RefSeq:NP_065391.1, amino acid numbers 1 to 25 of SEQ ID No.: 1). Codon-optimized NFMC63-28Z CAR construct was synthesized by Geneart® and cloned into pMX retroviral vector (Int J Hematol. 1998, 67:351-9). An amino acid sequence of NFMC63-28Z CAR is shown in SEQ ID NO: 1. NFMC63-28-d2RbZ CAR is a chimeric antigen receptor having a truncated fragment of the cytoplasmic domain of human IL-2 receptor β chain including box-1 motif and flanking tyrosine residue-510 (e.g. amino acid numbers 266 to 337 and 530 to 551 of NCBI RefSeq: NP_000869.1, SEQ ID No.: 5), between the CD28 domain and the CD3ζ domain of NFMC63-28Z CAR. An amino acid sequence of NFMC63-28-d2RbZ CAR is shown in SEQ ID NO: 2. NFMC63-28-21RaZ CAR is a chimeric antigen receptor having full-length cytoplasmic domain of human IL-21 receptor α chain (amino acid numbers 256 to 538 of NCBI RefSeq:NP_068570.1, SEQ ID No.: 6) between the CD28 domain and CD3ζ domain of NFMC63-28Z CAR. An amino acid sequence of NFMC63-28-21RaZ CAR is shown in SEQ ID NO: 3. NFMC63-28Z-21Ra CAR is a chimeric antigen receptor having full-length cytoplasmic domain of human IL-21 receptor α chain with N-terminus to NFMC63-28Z CAR. An amino acid sequence of NFMC63-28Z-21Ra CAR is shown in SEQ ID NO: 4. The structures of CARs are shown in FIG. 21. The nucleic acids encoding NFMC63-28-d2RbZ CAR, NFMC63-28-21RaZ CAR and NFMC63-28Z-21Ra CAR were constructed by inserting DNAs encoding respective cytoplasmic domains into NFMC63-28Z CAR construct in pMX retroviral vector.

Ecotropic retroviral vectors were obtained by transient transfection of CAR construct retroviral plasmids with TransIT293 (Mirus Bio) to phoenix-eco cell line; subsequently, PG13 cell lines were transduced with the ecotropic retroviral vectors obtained from transduced phoenix-eco cell line. GaLV-pseudotyped retroviral vectors were obtained from bulk of transduced PG13 cell lines and used for gene transduction into Jurkat cells.

Cells

PG13 cell line and phoenix-eco cell line were cultured in DMEM medium supplemented with 10% fetal calf serum (FCS) and 50 μg/mL gentamicin (Gibco).

K562 cells or K562 cells transduced with human CD80 and CD83 expression constructs were additionally transduced with a human CD19 expression construct and used as artificial antigen-presenting cells (aAPC cells, Clin Cancer Res., 2007, 13:1857-67, Immunol Rev., 2014, 257:191-209). K562 and K562-derived cells and Jurkat and Jurkat-derived cells were cultured in RPMI 1640 medium supplemented with 10% FCS and 50 μg/mL gentamicin.

CAR Construct Transfer and Cell Sorting

The cells were transduced using the RetroNectin-bound virus infection method (J Biochem. 2001 September; 130 (3):331-4), in which retroviral solutions were preloaded onto RetroNectin (registered trademark, Takara Bio) coated plates, centrifuged at 2,000 g for 2 hours at 32° C., and then rinsed with phosphate-buffered saline including bovine serum albumin. Jurkat cells were applied to the virus-preloaded plate. This gene transfer was performed twice.

Following gene transfer of CAR constructs, cells were sorted with Biotin-Protein L (GenScript) and Anti-Biotin MicroBeads (Miltenyi Biotec). After sorting more than 95% positivity and equal level of mean fluorescent intensity of transferred CAR constructs were confirmed.

STAT Phosphorylation

CAR transduced Jurkat cells and aAPCs were counted and mixed on ice. Following spinning down at 4° C., cells were incubated in 37° C. waterbath. After incubation, cells were fixed in 1.5% paraformaldehyde and permeabilized with 100% methanol. Subsequently cells were stained with the following antibodies; Phospho-p44/42 MAP kinase (Cell signaling technology, clone E10), Phospho-STAT3 (pY705) (BD Phosflow, clone 4/P-STAT3), and Phospho-STAT5 (pY694) (BD Phosflow, clone 47/P-STAT5). Flow cytometry acquisition was performed with a BD FacsCanto II (BD Biosciences), and analysis was performed with FlowJo (Treestar).

Figure 22:
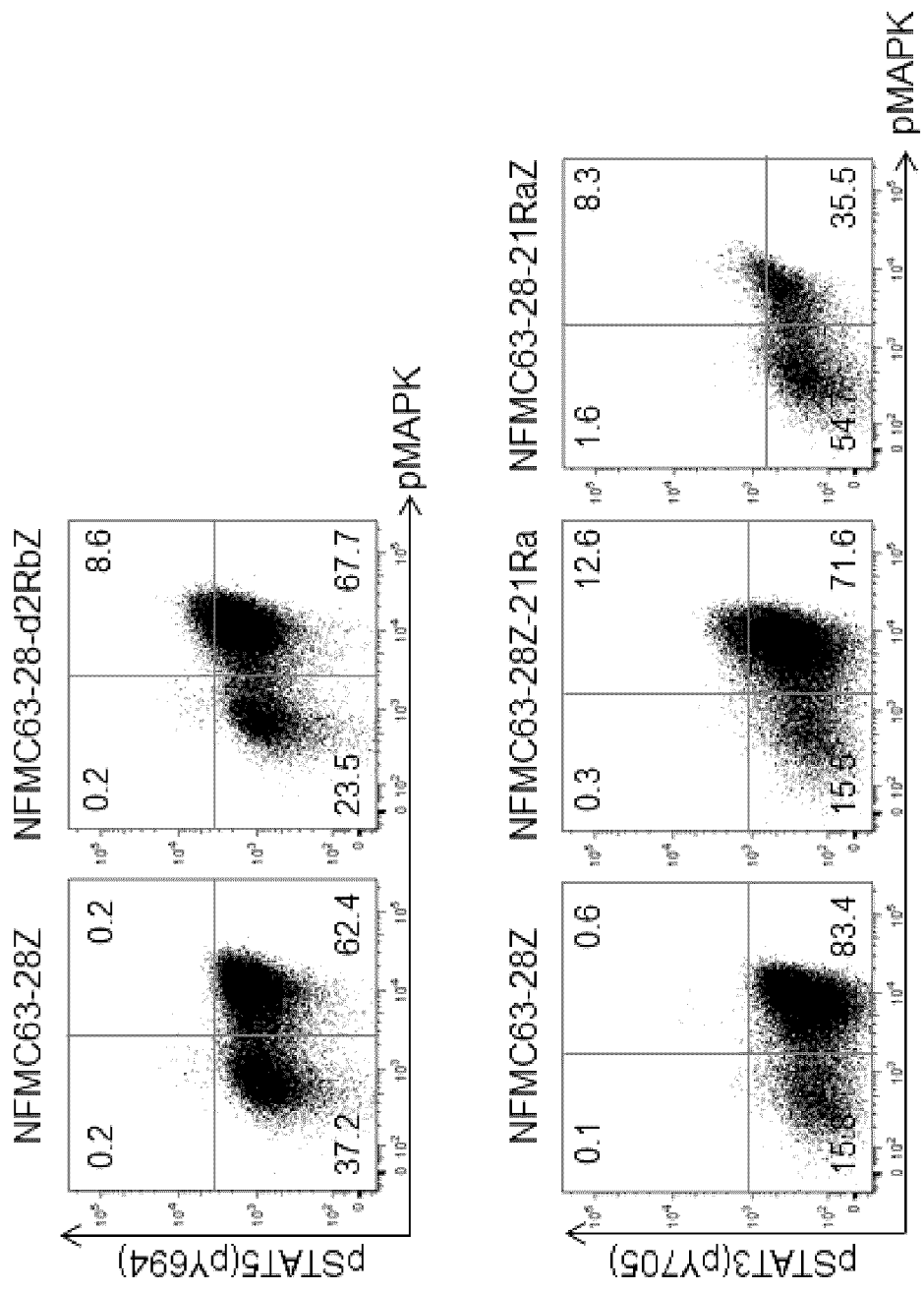
FIG. 22 shows STAT phosphorylation cells transduced with CARs of FIG. 21.

Results are shown in FIG. 22. As shown in upper figures of FIG. 2, NFMC63-28Z only shows MAP kinase phosphorylation which is a marker of CD3ζ signaling, whereas NFMC63-28-d2R5 shows STAT5 phosphorylation in a phospho-MAP kinase positive fraction. Also, as shown in lower figures of FIG. 2, both NFMC63-28-21RaZ and NFMC63-28Z-21Ra show STAT3 phosphorylation in a phospho-MAP kinase positive fraction. These results indicate that these CARs can activate STAT5 or STAT3 signaling which are the main targets of IL-2 and IL-21 signaling respectively in addition to MAP kinase signaling upon antigen stimulation.

Example 5

In Vivo Antileukemic Effects in Mice

Immunodeficient NSG mice harboring human CD19+ NALME B leukemic cells were treated with the 28-IL2RB-z (YXXQ) anti-CD19 CAR or with previous generation CAR T cells.

Figure 18:
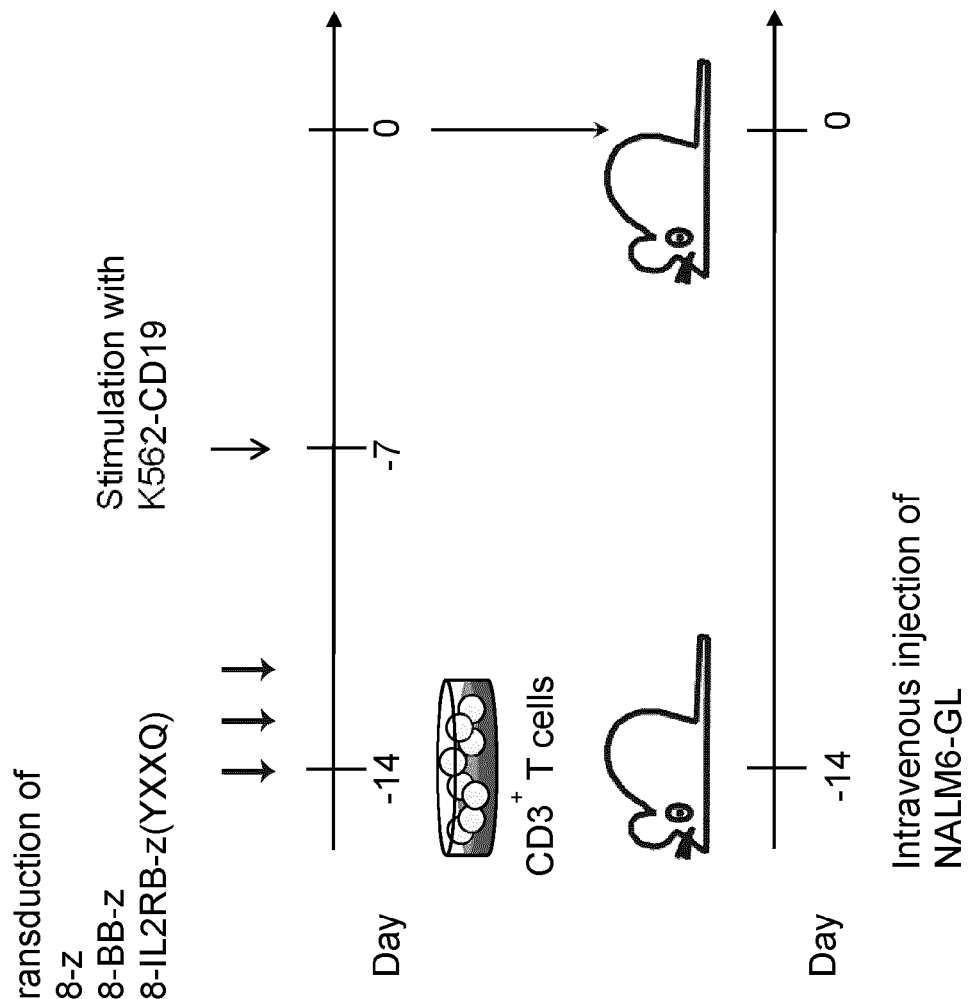
FIG. 18 is a schematic illustrating a protocol for injection of immunodeficient mice with CD19-positive acute lymphoblastic leukemia cell line NALM-6 which expresses EGFP-luciferase, followed by injection with CAR-transduced T cells.

CD3+ T cells were retrovirally transduced with either 28-z, 28-BB-z, or 28-IL2RB-z (YXXQ) anti-CD19 CAR, and stimulated with CD19-transduced K562 cells, as shown in FIG. 18. Immunodeficient NSG mice were intravenously injected with the CD19-positive acute lymphoblastic leukemia cell line NALM-6, which expresses EGFP-luciferase (NALM6-GL), and then they were injected with CAR-transduced T cells 14 days following tumor injection.

Figure 19:
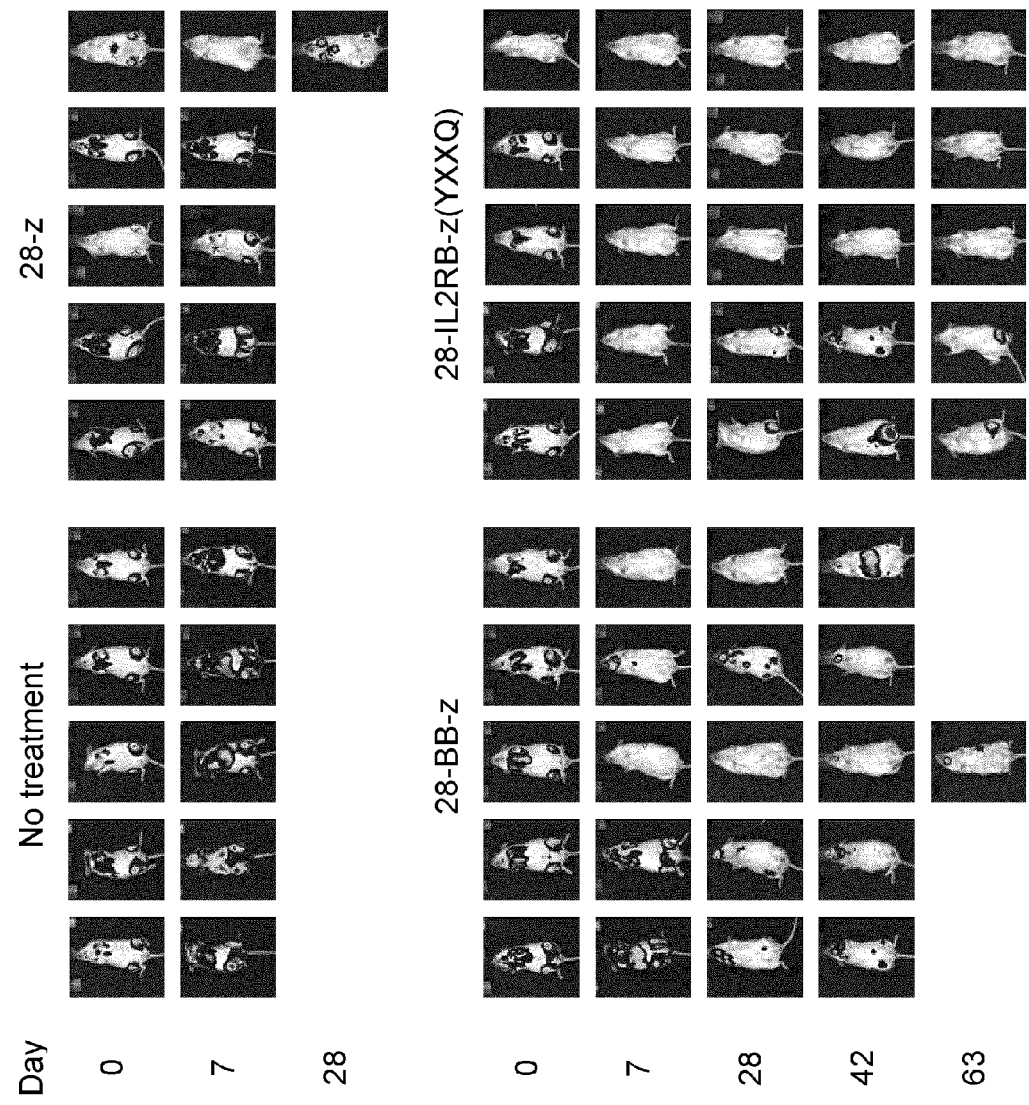
FIG. 19 is a series of bioluminescent imaging of luciferase activity at the indicated time points following infusion of the anti-CD19 CAR-transduced T cells.
Figure 20:
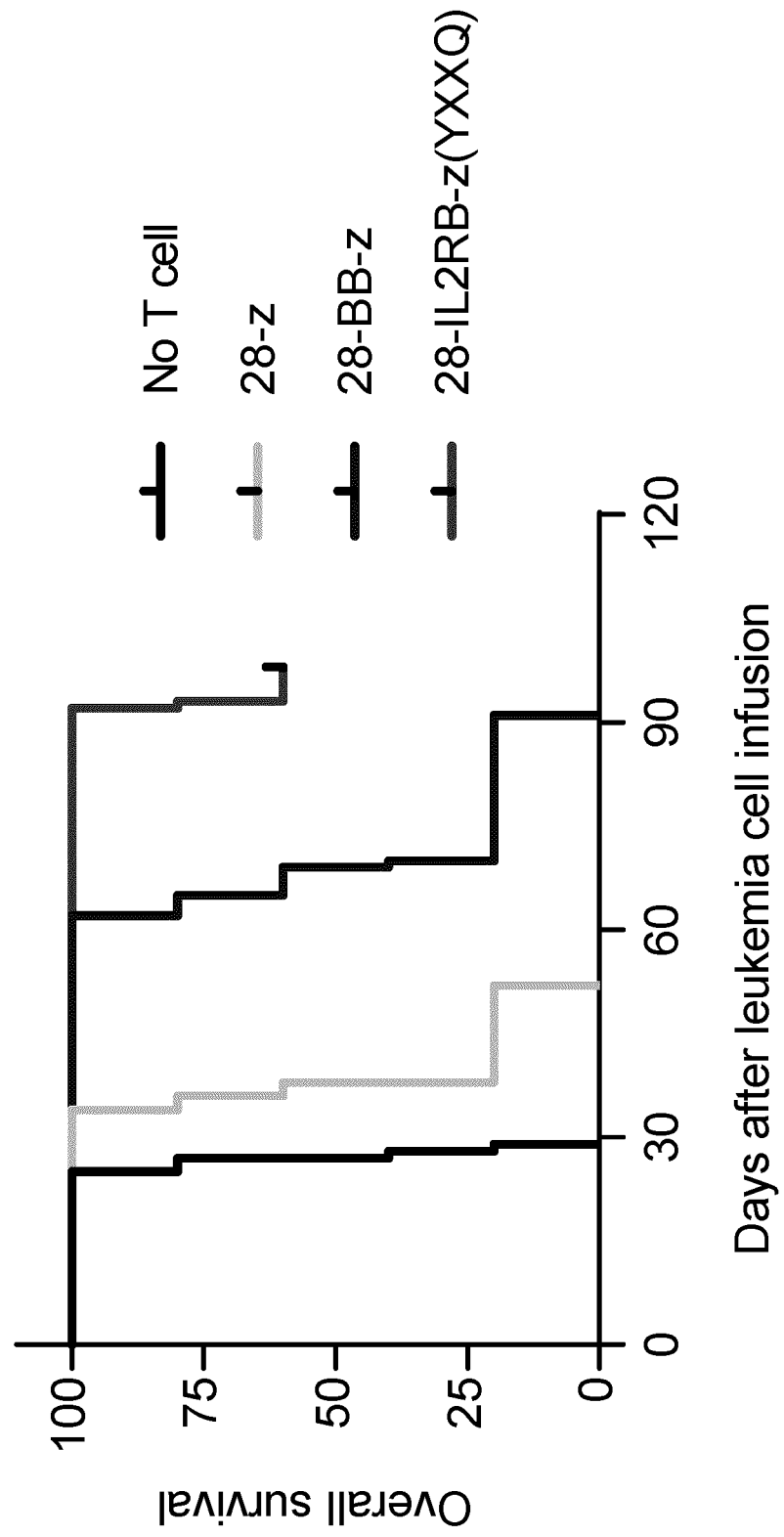
FIG. 20 is a graph showing Kaplan-Meier curve for overall survival of the mice treated with anti-CD19 CAR-transduced T cells (n=5 each).

In vivo bioluminescent imaging of luciferase activity is shown in FIG. 19 at day 0, 7, 28 for the no treatment and 28-z anti-CD19 CAR groups as well as day 0, 7, 28, 42 and 63 for the 28-BB-z and 28-IL2RB-z (YXXQ) anti-CD19 CARs groups following infusion of the anti-CD19 CAR-transduced T cells. Mice treated with 28-IL2RB-z (YXXQ) anti-CD19 CARs show a greater tumor activity decrease compared to the other groups.

Kaplan-Meier curve for overall survival of the mice treated with anti-CD19 CAR-transduced T cells (n=5 each) indicates that 28-IL2RB-z (YXXQ) anti-CD19 CAR treated mice had a better overall survival rate compared to the non-treated group as well as the previous generation 28-z and 28-BB-z anti-CD19 CARs.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

TABLE OF SEQUENCES

```
SEQ ID NO: 1: NFMC63-28Z
MGVLLTQRTLLSLVLALLFPSMASMDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFG
GGTKLEITGSTSGSGKPGSGEGSTKGEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYYCA
KHYYYGGSYAMDYWGQGTSVTVSSAAAIEVMYPPPYLDNEKSNGTIIHVKGKHLCPSPLFP
GPSKPFWVLVVVGGVLACYSLLVTVAFIIFWVRSKRSRLLHSDYMNMTPRRPGPTRKHYQP
YAPPRDFAAYRSRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHM
QALPPR 1-25: SIGNAL PEPTIDE 26-270: FMC63 SCFV 274-312: CD28 PARTIAL EXTRACELLULAR DOMAIN 313-339: CD28 TRANSMEMBRANE DOMAIN 340-380: CD28 CYTOPLASMIC DOMAIN 381-492: INTRACELLULAR DOMAIN OF CD3ζ

SEQ ID NO: 2: NFMC63-28-d2RbZ
QKPDGTVKLLIYHTSRLHSGVPSRFSGSGSGTDYSLTISNLEQEDIATYFCQQGNTLPYTFG
GGTKLEITGSTSGSGKPGSGEGSTKGEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYYCA
KHYYYGGSYAMDYWGQGTSVTVSSAAAIEVMYPPPYLDNEKSNGTIIHVKGKHLCPSPLFP
GPSKPFWVLVVVGGVLACYSLLVTVAFIIFWVRSKRSRLLHSDYMNMTPRRPGPTRKHYQP
YAPPRDFAAYRSIDGGGSGGGGSGGGGSNCRNTGPWLKKVLKCNTPDPSKFFSQLSSE
HGGDVQKWLSSPFPSSSFSPGGLAPEISPLEVLERDKVTQLLPLNTDAYLSLQELQGQDPT
HLVKLGGSGPRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDTYDALHMQA
LPPR 1-25: SIGNAL PEPTIDE 26-270: FMC63 SCFV 274-312: CD28 PARTIAL EXTRACELLULAR DOMAIN 313-339: CD28 TRANSMEMBRANE DOMAIN 340-380: CD28 CYTOPLASMIC DOMAIN 398-491: PARTIAL CYTOPLASMIC IL-2 RECEPTOR BETA DOMAIN 499-610: INTRACELLULAR DOMAIN OF CD3ζ

SEQ ID NO: 3: NFMC63-28-21RaZ
MGVLLTQRTLLSLVLALLFPSMASMDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFG
GGTKLEITGSTSGSGKPGSGEGSTKGEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYYCA
KHYYYGGSYAMDYWGQGTSVTVSSAAAIEVMYPPPYLDNEKSNGTIIHVKGKHLCPSPLFP
GPSKPFWVLVVVGGVLACYSLLVTVAFIIFWVRSKRSRLLHSDYMNMTPRRPGPTRKHYQP
YAPPRDFAAYRSKTHPLWRLWKKIWAVPSPERFFMPLYKGCSGDFKKWVGAPFTGSSLEL
GPWSPEVPSTLEVYSCHPPRSPAKRLQLTELQEPAELVESDGVPKPSFWPTAQNSGGSAY
SEERDRPYGLVSIDTVTVLDAEGPCTWPCSCEDDGYPALDLDAGLEPSPGLEDPLLDAGTT
VLSCGCVSAGSPGLGGPLGSLLDRLKPPLADGEDWAGGLPWGGRSPGGVSESEAGSPLA
GLDMDTFDSGFVGSDCSSPVECDFTSPGDEGPPRSYLRQWVVIPPPLSSPGPQASKLGGS
GPRVKFSRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR 1-25: SIGNAL PEPTIDE 26-270: FMC63 SCFV 274-312: CD28 PARTIAL EXTRACELLULAR DOMAIN 313-339: CD28 TRANSMEMBRANE DOMAIN 340-380: CD28 CYTOPLASMIC DOMAIN 381-663: FULL-LENGTH CYTOPLASMIC IL-21 RECEPTOR ALPHA DOMAIN 671-782: INTRACELLULAR DOMAIN OF CD3ζ
```

SEQ ID NO: 4: NFMC63-28Z-21Ra
MGVLLTQRTLLSLVLALLFPSMASMDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFG
GGTKLEITGSTSGSGKPGSGEGSTKGEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYYCA
KHYYYGGSYAMDYWGQGTSVTVSSAAAIEVMYPPPYLDNEKSNGTIIHVKGKHLCPSPLFP
GPSKPFWVLVVVGGVLACYSLLVTVAFIIWVRSKRSRLLHSDYMNMTPRRPGPTRKHYQP
YAPPRDFAAYRSRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHM
QALPPRGGGSGGGGSGGGGSKTHPLWRLWKKIWAVPSPERFFMPLYKGCSGDFKKVW
GAPFTGSSLELGPWSPEVPSTLEVYSCHPPRSPAKRLQLTELQEPAELVESDGVPKPSFW
PTAQNSGGSAYSEERDRPYGLVSIDTVTVLDAEGPCTWPCSCEDDGYPALDLDAGLEPSP
GLEDPLLDAGTTVLSCGCVSAGSPGLGGPLGSLLDRLKPPLADGEDWAGGLPWGGRSPG
GVSESEAGSPLAGLDMDTFDSGFVGSDCSSPVECDFTSPGDEGPPRSYLRQWVVIPPPLS
SPGPQAS 1-25: SIGNAL PEPTIDE 26-270: FMC63 SCFV 274-312: CD28 PARTIAL EXTRACELLULAR DOMAIN 313-339: CD28 TRANSMEMBRANE DOMAIN 340-380: CD28 CYTOPLASMIC DOMAIN 381-492: INTRACELLULAR DOMAIN OF CD3ζ

508-790: FULL-LENGTH CYTOPLASMIC IL-21 RECEPTOR ALPHA DOMAIN

SEQ ID NO: 5: Truncated fragment of the cytoplasmic domain of IL-2R β chain
NCRNTGPWLKKVLKCNTPDPSKFFSQLSSEHGGDVQKWLSSPFPSSSFSPGGLAPEISPL
EVLERDKVTQLLPLNTDAYLSLQELQGQDPTHLV SEQ ID NO: 6: cytoplasmic domain of human IL-21 receptor α chain
KTHPLWRLWKKIWAVPSPERFFMPLYKGCSGDFKKWVGAPFTGSSLELGPWSPEVPSTLE
VYSCHPPRSPAKRLQLTELQEPAELVESDGVPKPSFWPTAQNSGGSAYSEERDRPYGLVS
IDTVTVLDAEGPCTWPCSCEDDGYPALDLDAGLEPSPGLEDPLLDAGTTVLSCGCVSAGSP
GLGGPLGSLLDRLKPPLADGEDWAGGLPWGGRSPGGVSESEAGSPLAGLDMDTFDSGFV
GSDCSSPVECDFTSPGDEGPPRSYLRQWVVIPPPLSSPGPQAS 11-19: BOX 1 MOTIF

264: PHOSPHORYLATABLE TYROSINE RESIDUE 265-267-tyrosine flanking residues

SEQ ID NO: 7: intracellular domain of CD3ζ
RVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR SEQ ID NO: 8: intracellular domain of CD28
RSKRSRLLHSDYMNMTPRRPGPTRKHYQPYAPPRDFAAYRS SEQ ID NO: 9: transmembrane domain of CD28
FWVLVVVGGVLACYSLLVTVAFIIFWV SEQ ID NO: 10: partial extracellular domain of CD28
IEVMYPPPYLDNEKSNGTIIHVKGKHLCPSPLFPGPSKP SEQ ID NO: 11
NP_000869.1, 266-551:
NCRNTGPWLKKVLKCNTPDPSKFFSQLSSEHGGDVQKWLSSPFPSSSFSPGGLAPEISPL
EVLERDKVTQLLQQDKVPEPASLSSNHSLTSCFTNQGYFFFHLPDALEIEACQVYFTYDPY
SEEDPDEGVAGAPTGSSPQPLQPLSGEDDAYCTFPSRDDLLLFSPSLLGGPSPPSTAPGG
SGAGEERMPPSLQERVPRDWDPQPLGPPTPGVPDLVDFQPPPELVLREAGEEVPDAGPR
EGVSFPWSRPPGQGEFRALNARLPLNTDAYLSLQELQGQDPTHLV

SEQ ID NO: 12-YLSLQ

SEQ ID NO: 13-YXXQ

SEQ ID NO: 14-YLPSNID

SEQ ID NO: 15-YCTFP

SEQ ID NO: 16-YFFFH

SEQ ID NO: 17-YVTMS

SEQ ID NO: 18-YLPQE

SEQ ID NO: 19-KLGGSGP

SEQ ID NO: 20-YKAFS

SEQ ID NO: 21-YKPFQ

SEQ ID NO: 22-YRHQ

SEQ ID NO: 23-YXPQ

SEQ ID NO: 24: 28-IL2RB-z(YXXQ)WITH STAT3 ASSOCIATION MOTIF AT POSITIONS
104-107 OF THE INTRACELLULAR DOMAIN OF CD3ζ
MGVLLTQRTLLSLVLALLFPSMASMDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFG
GGTKLEITGSTSGSGKPGSGEGSTKGEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYYCA
KHYYYGGSYAMDYWGQGTSVTVSSAAAIEVMYPPPYLDNEKSNGTIIHVKGKHLCPSPLFP
GPSKPFWVLVVVGGVLACYSLLVTVAFIIFWVRSKRSRLLHSDYMNMTPRRPGPTRKHYQP
YAPPRDFAAYRSNCRNTGPWLKKVLKCNTPDPSKFFSQLSSEHGGDVQKWLSSPFPSSSF
SPGGLAPEISPLEVLERDKVTQLLPLNTDAYLSLQELQGQDPTHLVRVKFSRSADAPAYQQ
GQNQLYNELNLGRREEYDVLDKRRGRDPEMGGKPRRKNPQEGLYNELQKDKMAEAYSEI
GMKGERRRGKGHDGLYQGLSTATKDTYDAYXXQALPPR 1-25: SIGNAL PEPTIDE 26-270: FMC63 SCFV 274-312: CD28 PARTIAL EXTRACELLULAR DOMAIN 313-339: CD28 TRANSMEMBRANE DOMAIN 340-380: CD28 CYTOPLASMIC DOMAIN 381-474: PARTIAL CYTOPLASMIC IL-2 RECEPTOR BETA DOMAIN 475-586: INTRACELLULAR DOMAIN OF CD3ζ COMPRISING EXOGENOUS STAT3
ASSOCIATION MOTIF YXXQ

SEQ ID NO: 25: 28-IL2RB-z(YRHQ) WITH STAT3 ASSOCIATION MOTIF YRHQ (SEQ ID
NO: 22) AT POSITIONS 104-107 OF THE INTRACELLULAR DOMAIN OF CD3ζ
MGVLLTQRTLLSLVLALLFPSMASMDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFG
GGTKLEITGSTSGSGKPGSGEGSTKGEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYYCA
KHYYYGGSYAMDYWGQGTSVTVSSAAAIEVMYPPPYLDNEKSNGTIIHVKGKHLCPSPLFP
GPSKPFWVLVVVGGVLACYSLLVTVAFIIFWVRSKRSRLLHSDYMNMTPRRPGPTRKHYQP
YAPPRDFAAYRSNCRNTGPWLKKVLKCNTPDPSKFFSQLSSEHGGDVQKWLSSPFPSSSF
SPGGLAPEISPLEVLERDKVTQLLPLNTDAYLSLQELQGQDPTHLVRVKFSRSADAPAYQQ
GQNQLYNELNLGRREEYDVLDKRRGRDPEMGGKPRRKNPQEGLYNELQKDKMAEAYSEI
GMKGERRRGKGHDGLYQGLSTATKDTYDAYRHQALPPR 1-25: SIGNAL PEPTIDE 26-270: FMC63 SCFV 274-312: CD28 PARTIAL EXTRACELLULAR DOMAIN 313-339: CD28 TRANSMEMBRANE DOMAIN 340-380: CD28 CYTOPLASMIC DOMAIN 381-474: PARTIAL CYTOPLASMIC IL-2 RECEPTOR BETA DOMAIN 475-586: INTRACELLULAR DOMAIN OF CD3ζ COMPRISING EXOGENOUS STAT3
ASSOCIATION MOTIF YRHQ

SEQ ID NO: 26-ACGCCTATCGCCATCAGGCCCTGC

SEQ ID NO: 27-CTGATGGCGATAGGCGTCGTAGGTGT

SEQ ID NO: 28-YFFF

SEQ ID NO: 29-YCTF

SEQ ID NO: 30-YLRQ

SEQ ID NO: 31-YFKQ

SEQ ID NO: 32-YLPQ

SEQ ID NO: 33-YMPQ

SEQ ID NO: 34-YVLQ

SEQ ID NO: 35-YQPQ

SEQ ID NO: 36-YKPQ

SEQ ID NO: 37-YRPQ

SEQ ID NO: 38-YTHQ

SEQ ID NO: 39-YLKQ

SEQ ID NO: 40-YHNQ

SEQ ID NO: 41-YXXL

SEQ ID NO: 42-IDGGGGSGGGGSGGGGS

SEQ ID NO: 43-YLSL

CITATION LIST

Markley J C et al. IL-7 and IL-21 are superior to IL-2 and IL-15 in promoting human T cell-mediated rejection of systemic lymphoma in immunodeficient mice. Blood, vol. 29, pp. 3508-3519.
Zeng R et al. Synergy of IL-21 and IL-15 in regulating CD8+ T cell expansion and function. J Exp Med, vol. 201, pp. 139-148.
Sadelain M et al Current Opinion in Immunology, vol. 21, pp. 215-223 (2009)
Finney, H. M. et al J. Immunology, vol. 172, pp. 104-113 (2004)
Thimeli M et al. Nature Biotechnology Vol 31, pp. 928-935 (2013)
Kisseleva T et al. Gene Vol 285, pp. 1-24 (2002)
Cui et al. Immunity 35, 795-805, 2011
Siegel et al. Immunity 34, 806-818, 2011
Kochenderfer et al. (J Immunother. 2009 September; 32(7): 689-702
Themeli et al. Nat Biotechnol. Vol 31, pp. 928-933. (2013)
Nicholson et al. Mol Immunol. Vol 34, pp. 1157-1165 (1997)
Butler et al. PLoS One. Vol 7, e30229. (2012)
Milone et al. Mol Ther. Vol 17, pp. 1453-1464. (2009)
Love P E, Hayes S M. ITAM-mediated signaling by the T-cell antigen receptor. Cold Spring Harb Perspect Biol. 2010; 2(6):a002485.
Irving B A, Chan A C, Weiss A. Functional characterization of a signal transducing motif present in the T cell antigen receptor zeta chain. J Exp Med. 1993; 177(4):1093-103.
Shores E W, Tran T, Grinberg A, Sommers C L, Shen H, Love P E. Role of the multiple T cell receptor (TCR)-zeta chain signaling motifs in selection of the T cell repertoire. J Exp Med. 1997; 185(5):893-900.
Shao H, Xu X, Mastrangelo M A, Jing N, Cook R G, Legge G B, Tweardy D J. Structural requirements for signal transducer and activator of transcription 3 binding to phosphotyrosine ligands containing the YXXQ motif. J Biol Chem. 2004; 279(18):18967-73.
Friedmann M C, Migone T S, Russell S M, Leonard W J. Different interleukin 2 receptor beta-chain tyrosines couple to at least two signaling pathways and synergistically mediate interleukin 2-induced proliferation. Proc Natl Acad Sci USA. 1996; 93(5):2077-82.
Klingmüller U, Bergelson S, Hsiao J G, Lodish H F. Multiple tyrosine residues in the cytosolic domain of the erythropoietin receptor promote activation of STAT5. Proc Natl Acad Sci USA. 1996; 93(16):8324-8.
Klock H E, Koesema E J, Knuth M W, Lesley S A (2008) Combining the polymerase incomplete primer extension method for cloning and mutagenesis with microscreening to accelerate structural genomics efforts. Proteins 71: 982-994.
Li M Z, Elledge S J (2007) Harnessing homologous recombination in vitro to generate recombinant DNA via SLIC. Nat Methods 4: 251-256.
Bryksin A V, Matsumura I (2010) Overlap extension PCR cloning: a simple and reliable way to create recombinant plasmids. Biotechniques 48: 463-465.
Unger T, Jacobovitch Y, Dantes A, Bernheim R, Peleg Y (2010) Applications of the Restriction Free (RF) cloning procedure for molecular manipulations and protein expression. J Struct Biol 172: 34-44.
Schmitz J. et al. The cytoplasmic tyrosine motifs in full-length glycoprotein 130 have different roles in IL-6 signal transduction. J Immunol. 2000; 164:848-54.
Tomida M et al. 1999. Cytoplasmic domains of the leukemia inhibitory factor receptor required for STAT3 activation, differentiation, and growth arrest of myeloid leukemic cells. Blood. 1999; 93:1934-41.

The invention claimed is:

1. A chimeric antigen receptor (CAR) comprising i) an extracellular domain capable of binding to a predetermined antigen, ii) a transmembrane domain and iii) an intracellular segment comprising a) one or more intracellular signaling domains selected from a cytoplasmic domain of an interleukin receptor chain and a cytoplasmic co-stimulatory domain and b) a CD3ζ intracellular signaling domain comprising an exogenous Signal Transducer and Activator of Transcription (STAT) 3 association motif, wherein the intracellular segment comprises an endogenous or exogenous JAK-binding motif and a STAT5 association motif.

2. The CAR according to claim 1, wherein the exogenous STAT3 association motif is YXXQ (SEQ ID NO: 13), optionally YRHQ (SEQ ID NO: 22), and/or wherein the STAT5 association motif is YXXL (SEQ ID NO: 41).

3. The CAR according to claim 1, wherein the exogenous STAT3 association motif is located less than 100 amino acid residues from the C terminus of the CAR.

4. The CAR according to claim 1, wherein the one or more intracellular signaling domains is or comprises the cytoplasmic domain of an interleukin receptor chain.

5. The CAR according to claim 1, wherein the cytoplasmic domain of an interleukin receptor chain is a fragment comprising the endogenous or exogenous JAK-binding motif and the STAT5 association motif.

6. The CAR according to claim 1, wherein the one or more intracellular signaling domains is or comprises a cytoplasmic co-stimulatory domain, optionally wherein the cytoplasmic co-stimulatory domain is a cytoplasmic domain of CD28, CD2, CD4, CD5, CD8α, CD8β, CD134 or CD137.

7. The CAR according to claim 1, wherein the interleukin receptor chain is selected from the group consisting of interleukin 2 receptor (IL-2R) β chain and interleukin 21 receptor (IL-21 R) α chain.

8. The CAR according to claim 1, wherein the extracellular domain is an antigen binding region of an antibody, optionally wherein the antigen binding region is a single chain variable fragment.

9. A nucleic acid comprising a polynucleotide encoding a CAR of claim 1, optionally wherein the nucleic acid encodes a signal peptide at the N terminus of the CAR.

10. A vector comprising the nucleic acid of claim 9.

11. An immune cell which expresses the CAR of claim 1.

12. A composition comprising the CAR of claim 1, a nucleic acid comprising a polynucleotide encoding said CAR, a vector comprising said nucleic acid or a cell expressing said CAR, and optionally a pharmaceutically acceptable excipient.

13. A method of making a cell expressing a CAR, comprising:
   a) transfecting or transducing isolated immune cells, optionally T cells, with a nucleic acid comprising a polynucleotide encoding said CAR of claim 1, optionally wherein the immune cells are isolated from a mammal; and b) isolating and/or expanding the CAR-expressing cells, optionally CAR-expressing T cells, following transfection or transduction.

14. A method of providing an anti-tumor immunity in a subject, the method comprising administering to the subject in need thereof an effective amount of immune cells according to claim 11 or a composition comprising said cells, wherein said cells specifically bind to a predetermined antigen.

* * * * *